United States Patent
Luehrsen

(10) Patent No.: US 8,642,035 B2
(45) Date of Patent: Feb. 4, 2014

(54) ANTI-TRKB ANTIBODIES

(75) Inventor: Kenneth R. Luehrsen, Half Moon Bay, CA (US)

(73) Assignee: IRM LLC, Hamilton (BM)

( * ) Notice: Subject to any disclaimer, the term of this patent is extended or adjusted under 35 U.S.C. 154(b) by 488 days.

(21) Appl. No.: 12/864,636

(22) PCT Filed: Jan. 16, 2009

(86) PCT No.: PCT/US2009/031345
§ 371 (c)(1),
(2), (4) Date: Dec. 13, 2010

(87) PCT Pub. No.: WO2009/092049
PCT Pub. Date: Jul. 23, 2009

(65) Prior Publication Data
US 2011/0097326 A1    Apr. 28, 2011

Related U.S. Application Data

(60) Provisional application No. 61/021,820, filed on Jan. 17, 2008.

(51) Int. Cl.
  *A61K 39/395*     (2006.01)
  *C07K 16/18*      (2006.01)
  *C07K 16/22*      (2006.01)
  *C07K 16/28*      (2006.01)
  *A61P 3/04*       (2006.01)
  *A61P 3/10*       (2006.01)

(52) U.S. Cl.
  CPC ......... *C07K 16/2863* (2013.01); *C07K 2316/95* (2013.01)
  USPC .................. 424/133.1; 424/135.1; 424/146.1; 424/158.1; 530/387.3; 530/389.1; 530/389.2

(58) Field of Classification Search
  USPC ..................... 424/133.1, 135.1, 146.1, 158.1; 530/387.3, 389.1, 389.2
  See application file for complete search history.

(56) References Cited

FOREIGN PATENT DOCUMENTS

| EP | 2005996 |  | 12/2008 |
|---|---|---|---|
| WO | WO 2004/003019 | * | 1/2004 |
| WO | WO2008058127 |  | 5/2008 |
| WO | WO2009053442 |  | 4/2009 |

OTHER PUBLICATIONS

Rudikoff et al (Proc Natl Acad Sci USA 1982 vol. 79 p. 1979).*
MacCallum et al. (J. Mol. Biol. (1996) 262:732-745).*
De Pascalis et al. (The Journal of Immunology (2002) 169, 3076-3084).*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. (J. Mol. Bio. (1999) 293, 865-881).*
Wu et al. (J. Mol. Biol. (1999) 294, 151-162).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Tsao et al., "TrkB Agonists Ameliorate Obesity and Associated Metabolic Conditions in Mice", Endocrinology, Dec. 6, 2007, pp. 1038-1048, vol. 149, No. 3,Baltimore, Maryland, US.
Qian et al., "Novel Agonist Monoclonal Antibodies Activate TrkB Receptors and Demonstrate Potent Neurotrophic Activities", Journal of Neuroscience, Sep. 1, 2006, pp. 9349-9403, vol. 26, No. 37, New York, New York, US.
Hanyu et al., "Brain-Derived Neurotrophic Factor Modulates Glucagon Secretion From Pancreatic Alpha Cells: Its Contribution to Glucose Metabolism", Diabetes, Obesity and Metabolism, Jan. 1, 2003, pp. 27-37, vol. 5, No. 1, Blackwell Science, Oxford, United Kingdom.
Tonra et al., "Brain-Derived Neurotrophic Factor Improves Blood Glucose Control and Alleviates Fasting Hyperglycemia in C578LKS-Lep4db/leprdb Mice", Diabetes, Mar. 1, 1999, pp. 588-594, vol. 48, No. 3, American Diabetes Associates, US.
Ono et al., "Brain-Derived Neurotrophic Factor Reduces Blood Glucose Level in Obese Diabetic Mice but not in Normal Mice", Biochemical and Biophysical Research Communications, Jan. 1, 1997, pp. 633-637, vol. 238, No. 2, Academic Press Inc., Orlando, Florida, US.
Lin et al., "Appetite Enhancement and Weight Gain by Peripheral Administration of TrkB Agonists in Non-Human Primates", PLOS One, Apr. 2, 2008, pp. 1-8, vol. 3, No. 4, Public Library of Science, San Francisco, California, US.
Rudikoff et al., "Single Amino Acid Substitution Altering Antigen-Binding Specificity", Proceedings of the Natinoal Academy of Sciences of USA, Mar. 1, 1982, pp. 1979-1983, vol. 79, National Academy of Science, Washington, DC, US.

* cited by examiner

*Primary Examiner* — Lynn Bristol
(74) *Attorney, Agent, or Firm* — Kerri Pollard Schray; Genomics Institute of the Novartis Research Foundation

(57) ABSTRACT

The present invention provides improved antibodies or antigen-binding molecules that specifically recognize and agonize the tyrosine receptor kinase B (TrkB) receptor, and methods of their use. Also provided in the invention are polynucleotides and vectors that encode such molecules and host cells that harbor the polynucleotides or vectors.

31 Claims, 18 Drawing Sheets

*Figure 5*

Fabs

Vh sequence alignment

| | |
|---|---|
| VH1 1-02 | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCAR—— |
| TR134-4 | QVQLVQSGAEVKKPGASVKVSCKASGYTFTAYDMHWVRQAPGQGLEWMGWIDPNSGGTRYAQKFQGRVTMTRDTSISTAYMELSRLTSDDTAVYYCTGVTTWFAY |
| TR135-8 | QVQLVQSGAEVKKPGASVKVSCKASGYTFTAYDMHWVRQAPGQGLEWMGWIDPNSGGTRYAQKFQGRVTMTRDTSISTAYMELSRLTSDDTAVYYCTGVTTWFAY |
| TR139-2 | QVQLVQSGAEVKKPGASVKVSCKASGYTFTAYDMHWVRQAPGQGLEWMGWIDPNSGGTRYAQKFQGRVTMTRDTSISTAYMELSRLTSDDTAVYYCTGVTTWFAY |
| TR151-1 | QVQLVQSGAEVKKPGASVKVSCKASGYTFTAYDMHWVRQAPGQGLEWMGWIDPNSGGTRYAQKFQGRVTMTRDTSISTAYMELSRLTSDDTAVYYCAGVTSWFAY |
| TR144-1 | QVQLVQSGAEVKKPGASVKVSCKASGYTFTAYDMHWVRQAPGQGLEWMGWIDPRSGDTSYKQKFQGRVTMTRDTSISTAYMELHRLRSDDTAVYYCTGVTTWFAY |

Vk sequence alignment

| | |
|---|---|
| VKII A23 | DIVMTQTPLSSPVTLGQPASISCRSSQSLVHSDGNTYLSWLQQRPGQPPRLLIYKISNRFSGVPDRFSGSGAGTDFTLKISRVEAEDVGVYYCMQATQFP |
| TR134-4 | MDVVMTQSPLSLPVTLGQPASISCRSSQSLLHSNGNTYLNWYQQTPGQPPRLLIYKISNRFSGVPDRFSGSGAGTDFTLKISRVEAEDVGVYYCMQGTHEPYT |
| TR135-8 | MDVVMTQSPLSLPVTLGQPASISCRSSQSLVHSNGNTYLNWYQQKPGQPPRLLIYKISNRFSGVPDRFSGSGAGTDFTLKISRVEAEDVGVYYCMQGTHEPYT |
| TR139-2 | MDVVMTQSPLSLPVTLGQPASISCRSSQSLVHSNGNTYLSWLQQRPGQPPRLLIYKISNRFSGVPDRFSGSGAGTDFTLKISRVEAEDVGVYYCMQGTHEPYT |
| TR151-1 | MDVVMTQSPLSLPVTLGQPASISCRSSQSLVHSNGNTYLSWLQQRPGQPPRLLIYKISNRFSGVPDRFSGSGAGTDFTLKISRVEAEDVGVYYCMPGTHEPYT |
| TR144-1 | MDVVMTQSPLSLPVTLGQPASISCRSSQSLVHSNGNTYLNWYQQKPGQPPRLLIYKISNRFSGVPDRFSGSGAGTDFTLKISRVEAEDVGVYYCMQGTHEPYT |

Figure 6

IgG

Vh sequence alignment

```
VH1 1-02  QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCAR——
TR127-2   QVQLVQSGAEVKKPGASVKVSCKASGYTFTAYDMHWVRQAPGQGLEWMGWIDPNSGGTRYAQKFQGRVTMTRDTSISTAYMELSRLTSDDTAVYYCTGVTTWFAY
TR143-3   QVQLVQSGAEVKKPGASVKVSCKASGYTFTAYDMHWVRQAPGQGLEWMGWIDPRSGDTSYKQKFQGRVTMTRDTSISTAYMELHRLRSDDTAVYYCTGVTTWFAY
TR154-2   QVQLVQSGAEVKKPGASVKVSCKASGYTFTAYDMHWVRQAPGQGLEWMGWIDPNSGGTRYAQKFQGRVTMTRDTSISTAYMELSRLTSDDTAVYYCAGVTSWFAY
```

Vk sequence alignment

```
VKII A23  DIVMTQTPLSSPVTLGQPASISCRSSQSLVHSDGNTYLSWLQQRPGQPPRLLIYKISNRFSGVPDRFSGSGAGTDFTLKISRVEAEDVGVYYCMQATQFP
TR119-1   MDIVMTQTPLSLPVTLGQPASISCRSSQSLLHSNGNTYLNWYQQTPGQPPRLLIYKISNRFSGVPDRFSGSGAGTDFTLKISRVEAEDVGVYYCMQGTHVPYT
TR129-1   MDIVMTQSPLSLPVTLGQPASISCRSSQSLVHSNGNTYLNWYQQKPGQPPRLLIYKISNRFSGVPDRFSGSGAGTDFTLKISRVEAEDVGVYYCMQGTHEPYT
TR137-1   MDIVMTQTPLSLPVTLGQPASISCRSSQSLVHSNGNTYLSWLQQRPGQPPRLLIYKISNRFSGVPDRFSGSGAGTDFTLKISRVEAEDVGVYYCMQGTHEPYT
```

*Figure 7*
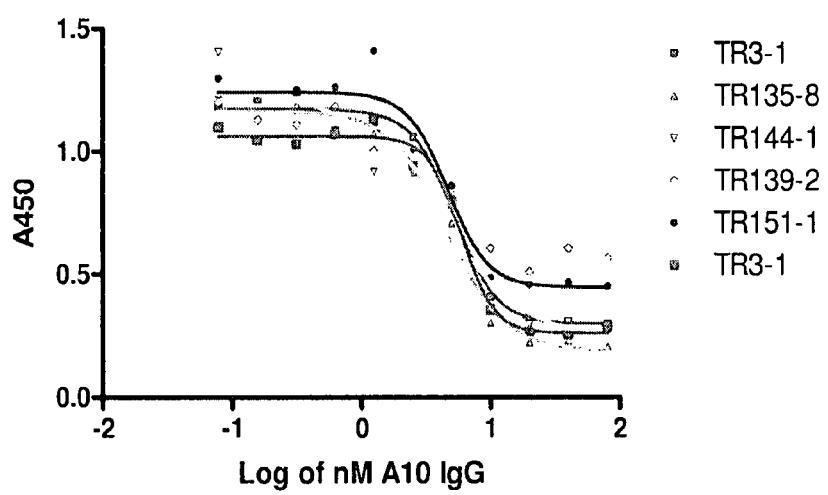
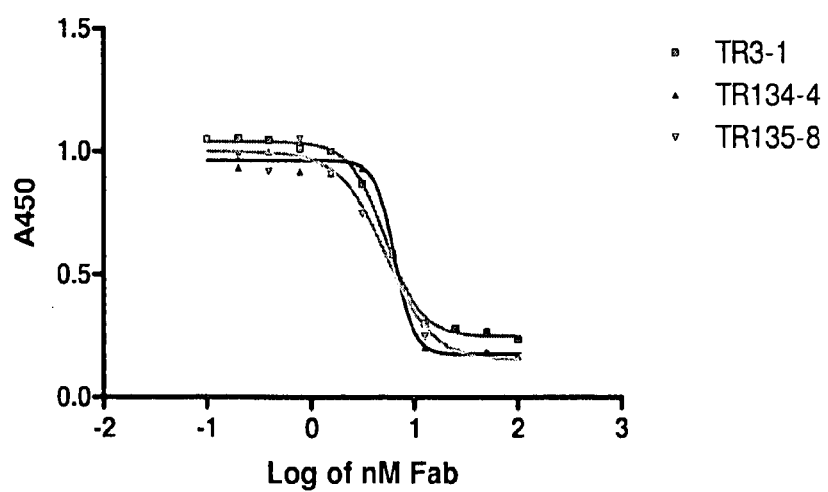

*Figure 8A-B*
A
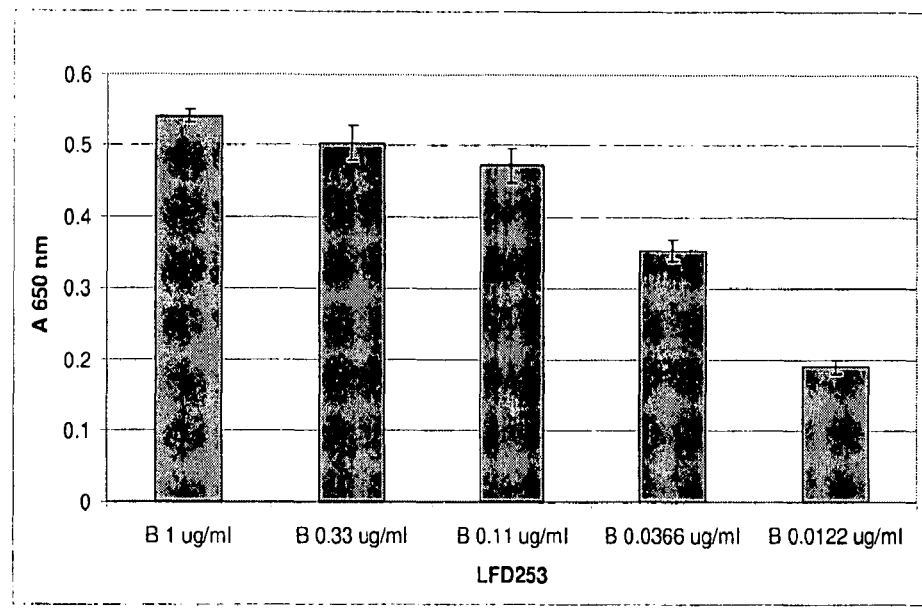
B
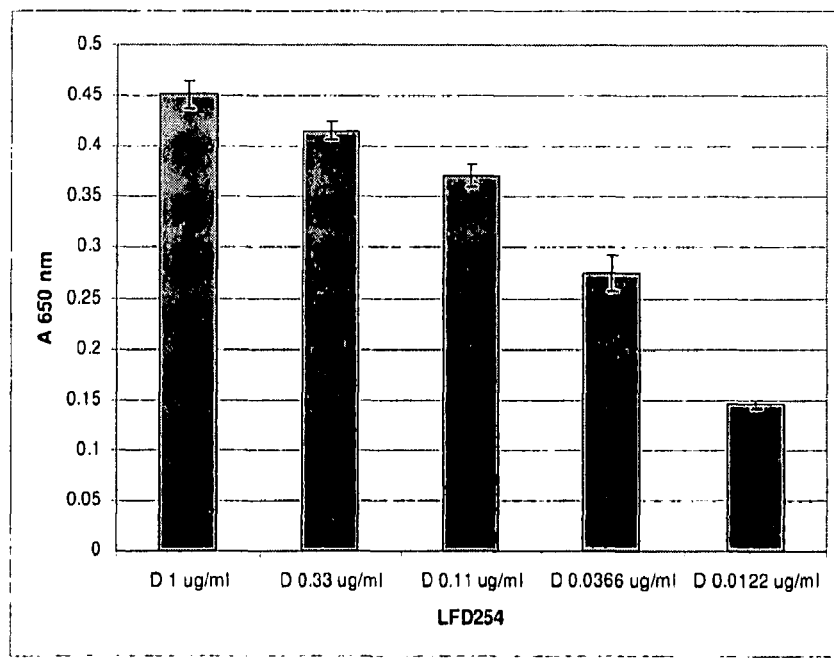

*Figure 8C-D*
C
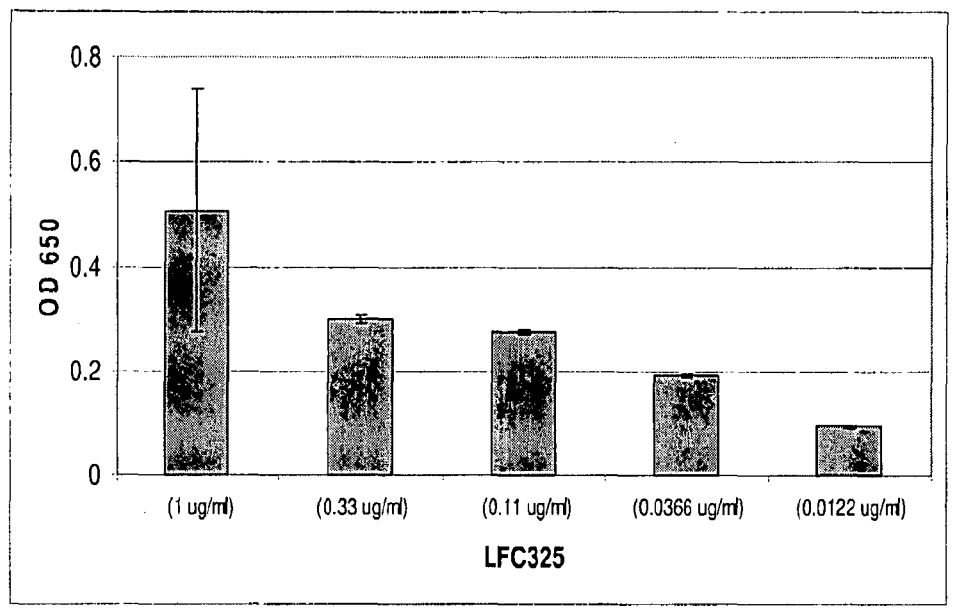
D
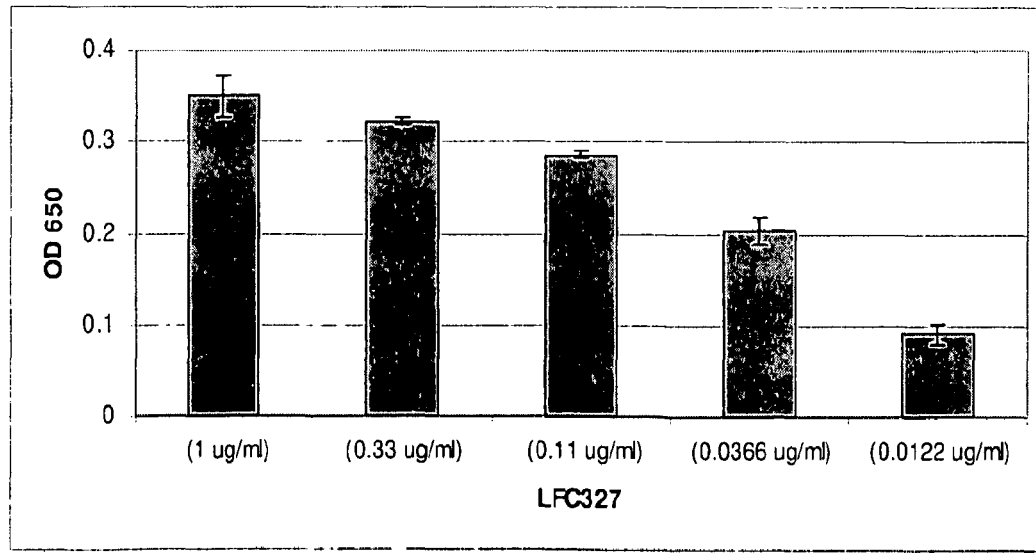

*Figure 9A-B*
A
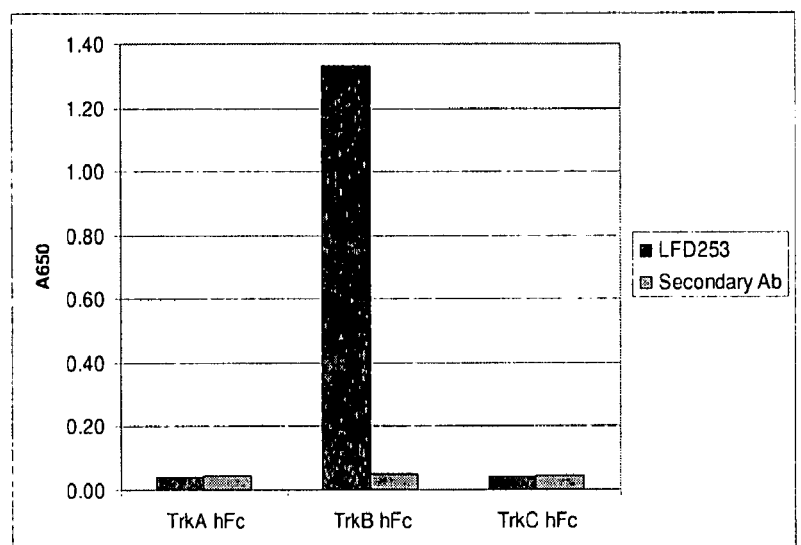
B
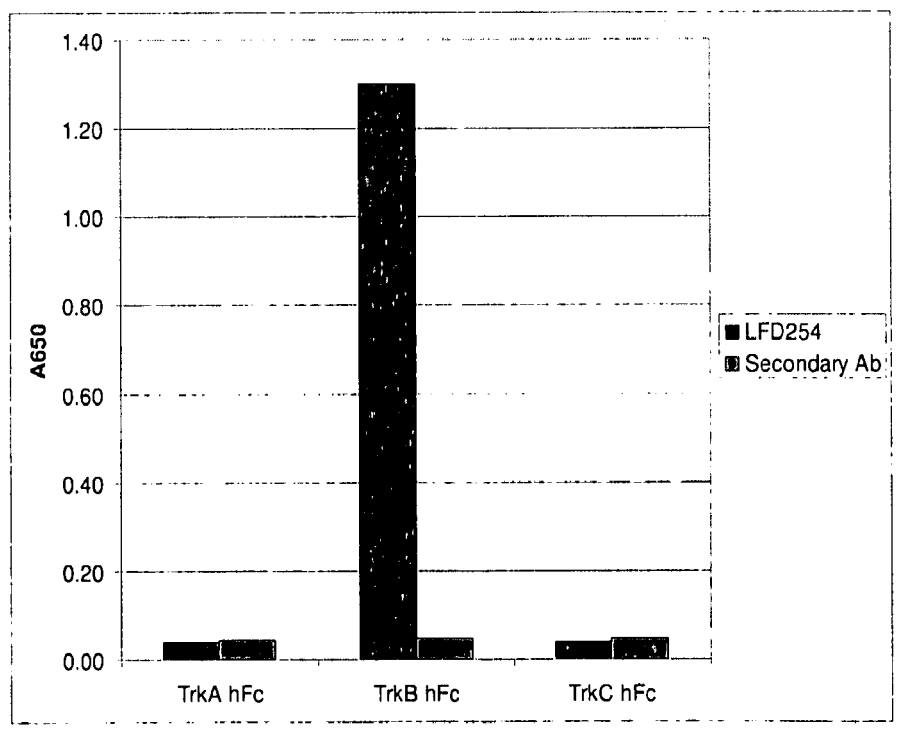

*Figure 9C-D*
C
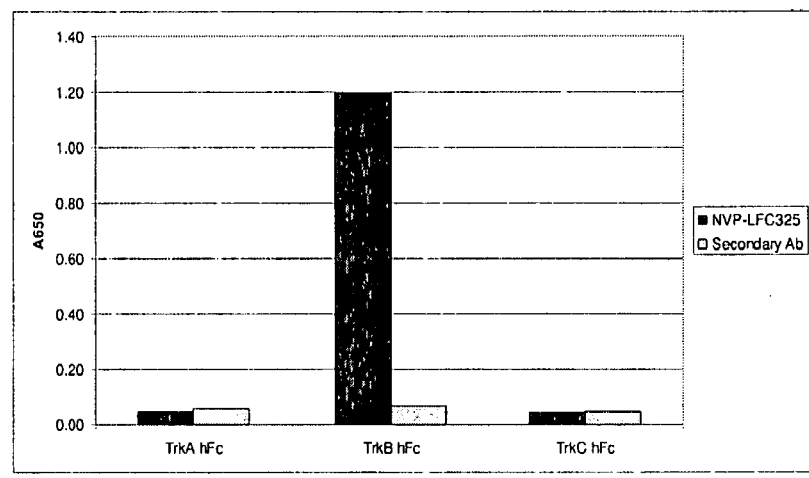
D
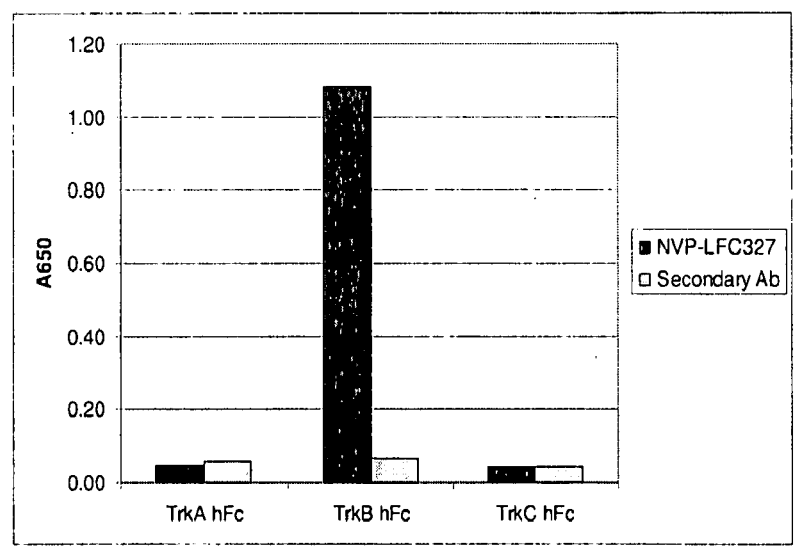

*Figure 10A-B*
A
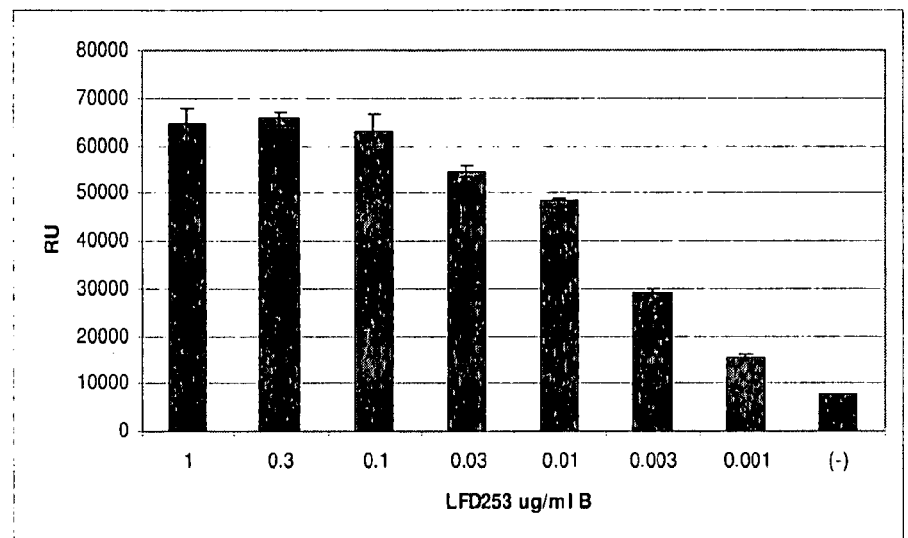
B
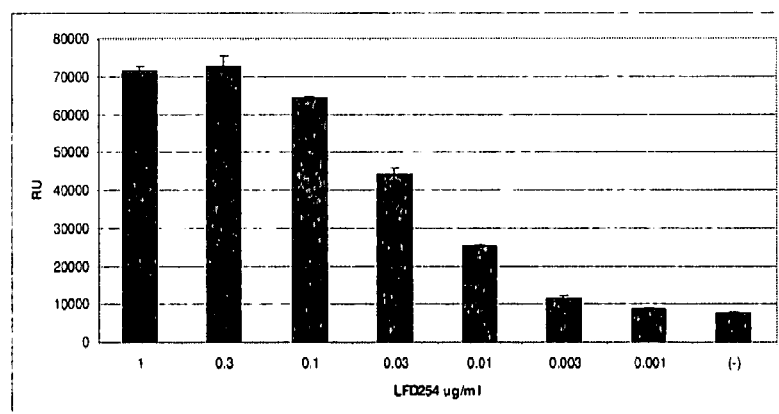

*Figure 10C-D*
C
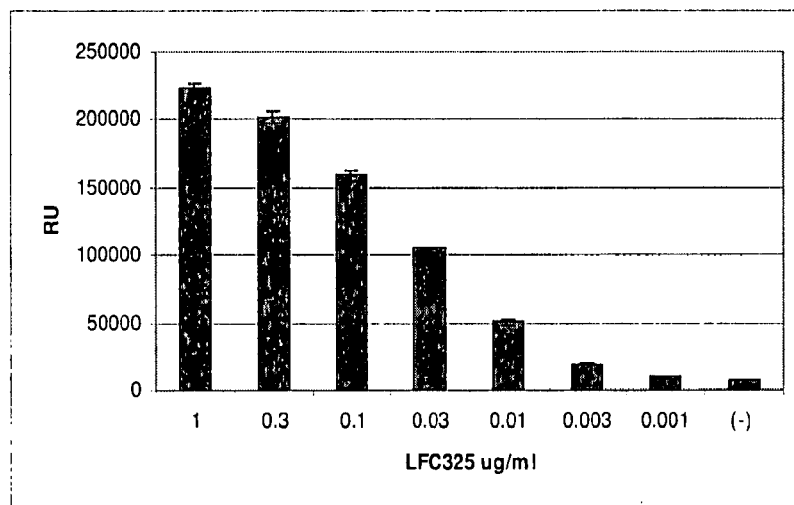
D
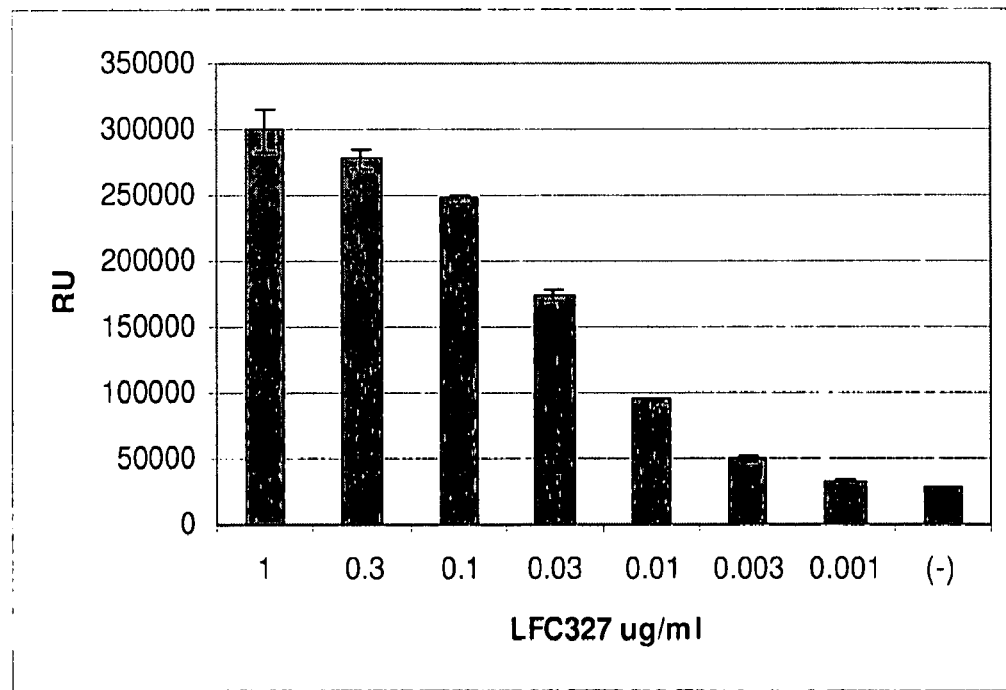

Figure 11A-B
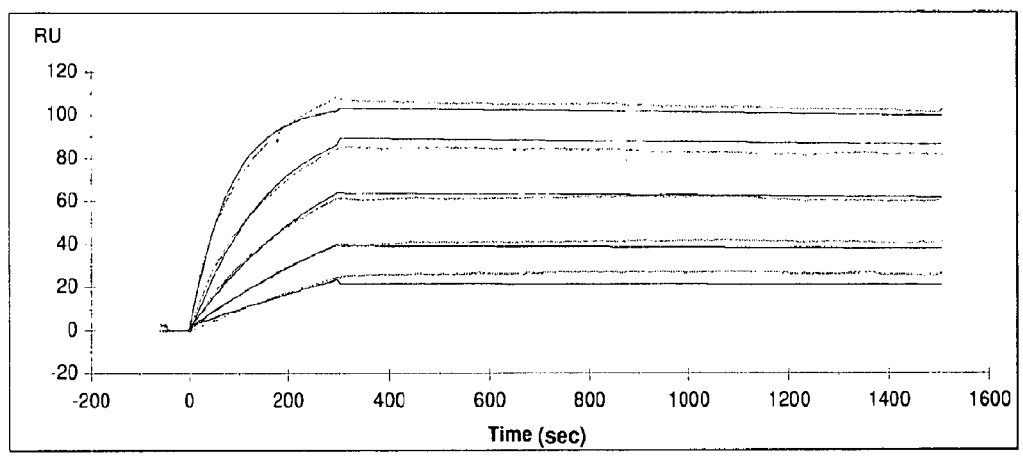
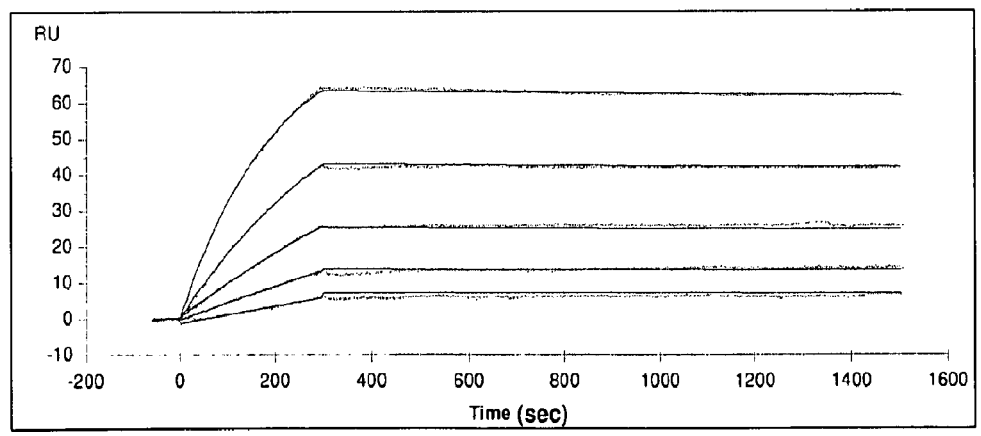

*Figure 11C-D*
C
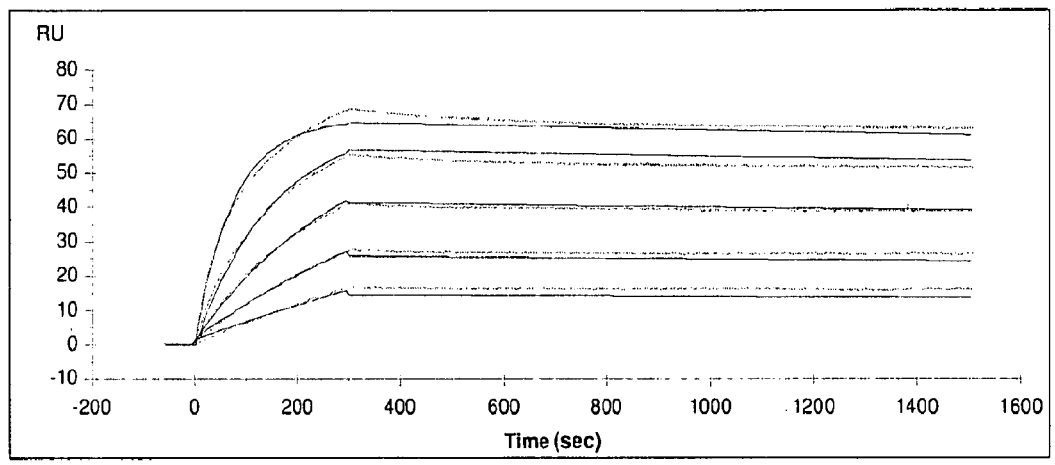
D
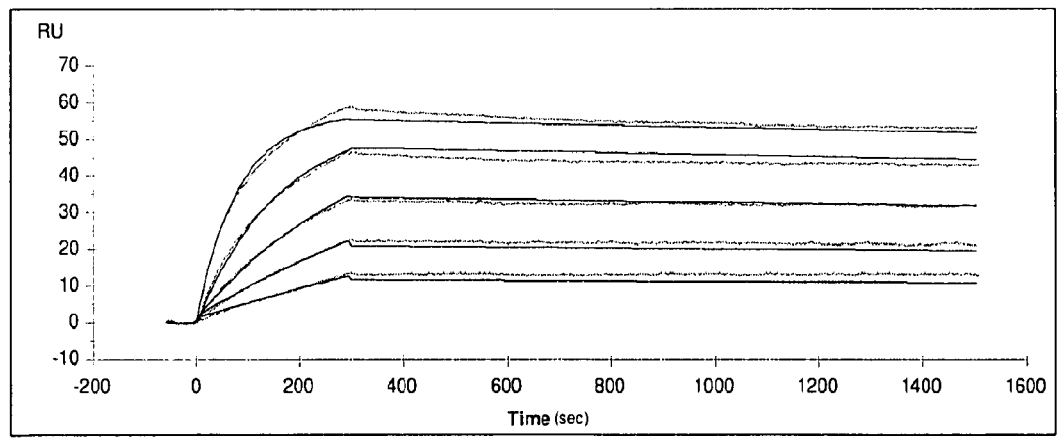

SEQUENCE LISTING

<160> NUMBER OF SEQ ID NOS: 86

<210> SEQ ID NO 1

```
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Syntheticpolypeptide"

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
                20                  25                  30

Asp Met His Trp Val Arg Gln Ala Pro Gly Gln Gly Leu Glu Trp Met
            35                  40                  45

Gly Trp Ile Asp Pro Asn Ser Gly Gly Thr Arg Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Thr Gly Val Thr Thr Trp Phe Ala Tyr Trp Gly Gln Gly Thr Leu Val
                100                 105                 110

Thr Val Ser Ser
        115

<210> SEQ ID NO 2
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
                20                  25                  30

Asp Met His Trp Val Arg Gln Ala Pro Gly Gln Gly Leu Glu Trp Met
            35                  40                  45

Gly Trp Ile Asp Pro Asn Ser Gly Gly Thr Arg Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Gly Val Thr Ser Trp Phe Ala Tyr Trp Gly Gln Gly Thr Leu Val
                100                 105                 110

Thr Val Ser Ser
        115

<210> SEQ ID NO 3
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

```
<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Asp Met His Trp Val Arg Gln Ala Pro Gly Gln Gly Leu Glu Trp Met
        35                  40                  45

Gly Trp Ile Asp Pro Arg Ser Gly Asp Thr Ser Tyr Gln Lys Phe
    50                  55                  60

Gln Gly Arg Val Thr Met Thr Arg Asp Thr Ser Ile Ser Thr Ala Tyr
65                  70                  75                  80

Met Glu Leu His Arg Leu Arg Ser Asp Asp Thr Ala Val Tyr Tyr Cys
                85                  90                  95

Thr Gly Val Thr Thr Trp Phe Ala Tyr Trp Gly Gln Gly Thr Leu Val
            100                 105                 110

Thr Val Ser Ser
        115

<210> SEQ ID NO 4
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (54)..(54)
<223> OTHER INFORMATION: /replace="Arg"
<220> FEATURE:
<221> NAME/KEY: misc_feature
<222> LOCATION: (54)..(54)
<223> OTHER INFORMATION: /note="Residue given in the sequence has no
      preference with respect to those in the annotations for said
      position"
<220> FEATURE:
<221> NAME/KEY: VARIANT
<222> LOCATION: (57)..(57)
<223> OTHER INFORMATION: /replace="Asp"
<220> FEATURE:
<221> NAME/KEY: misc_feature
<222> LOCATION: (57)..(57)
<223> OTHER INFORMATION: /note="Residue given in the sequence has no
      preference with respect to those in the annotations for said
      position"
<220> FEATURE:
<221> NAME/KEY: VARIANT
<222> LOCATION: (59)..(59)
<223> OTHER INFORMATION: /replace="Ser"
<220> FEATURE:
<221> NAME/KEY: misc_feature
<222> LOCATION: (59)..(59)
<223> OTHER INFORMATION: /note="Residue given in the sequence has no
      preference with respect to those in the annotations for said
      position"
<220> FEATURE:
<221> NAME/KEY: VARIANT
<222> LOCATION: (61)..(61)
<223> OTHER INFORMATION: /replace="Lys"
<220> FEATURE:
<221> NAME/KEY: misc_feature
<222> LOCATION: (61)..(61)
<223> OTHER INFORMATION: /note="Residue given in the sequence has no
      preference with respect to those in the annotations for said
      position"
<220> FEATURE:
<221> NAME/KEY: VARIANT
<222> LOCATION: (84)..(84)
<223> OTHER INFORMATION: /replace="Ser"
<220> FEATURE:
```

```
<221> NAME/KEY: misc_feature
<222> LOCATION: (84)..(84)
<223> OTHER INFORMATION: /note="Residue given in the sequence has no
      preference with respect to those in the annotations for said
      position"
<220> FEATURE:
<221> NAME/KEY: VARIANT
<222> LOCATION: (87)..(87)
<223> OTHER INFORMATION: /replace="Thr"
<220> FEATURE:
<221> NAME/KEY: misc_feature
<222> LOCATION: (87)..(87)
<223> OTHER INFORMATION: /note="Residue given in the sequence has no
      preference with respect to those in the annotations for said
      position"
<220> FEATURE:
<221> NAME/KEY: VARIANT
<222> LOCATION: (97)..(97)
<223> OTHER INFORMATION: /replace="Thr"
<220> FEATURE:
<221> NAME/KEY: misc_feature
<222> LOCATION: (97)..(97)
<223> OTHER INFORMATION: /note="Residue given in the sequence has no
      preference with respect to those in the annotations for said
      position"
<220> FEATURE:
<221> NAME/KEY: VARIANT
<222> LOCATION: (101)..(101)
<223> OTHER INFORMATION: /replace="Thr"
<220> FEATURE:
<221> NAME/KEY: misc_feature
<222> LOCATION: (101)..(101)
<223> OTHER INFORMATION: /note="Residue given in the sequence has no
      preference with respect to those in the annotations for said
      position"

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Asp Met His Trp Val Arg Gln Ala Pro Gly Gln Gly Leu Glu Trp Met
        35                  40                  45

Gly Trp Ile Asp Pro Asn Ser Gly Gly Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu His Arg Leu Arg Ser Asp Asp Thr Ala Val Tyr Tyr Cys
                85                  90                  95

Ala Gly Val Thr Ser Trp Phe Ala Tyr Trp Gly Gln Gly Thr Leu Val
            100                 105                 110

Thr Val Ser Ser
        115

<210> SEQ ID NO 5
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Met Asp Val Val Met Thr Gln Ser Pro Leu Ser Leu Pro Val Thr Leu
1               5                   10                  15

Gly Gln Pro Ala Ser Ile Ser Cys Arg Ser Ser Gln Ser Leu Leu His
            20                  25                  30
```

-continued

```
Ser Asn Gly Asn Thr Tyr Leu Asn Trp Tyr Gln Gln Thr Pro Gly Gln
            35                  40                  45

Pro Pro Arg Leu Leu Ile Tyr Lys Ile Ser Asn Arg Phe Ser Gly Val
    50                  55                  60

Pro Asp Arg Phe Ser Gly Ser Gly Ala Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Thr His Glu Pro Tyr Thr Phe Gly Gln Gly Lys Leu Glu Ile Lys
            100                 105                 110
```

<210> SEQ ID NO 6
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Met Asp Val Val Met Thr Gln Ser Pro Leu Ser Leu Pro Val Thr Leu
1               5                   10                  15

Gly Gln Pro Ala Ser Ile Ser Cys Arg Ser Ser Gln Ser Leu Val His
            20                  25                  30

Ser Asn Gly Asn Thr Tyr Leu Asn Trp Tyr Gln Gln Lys Pro Gly Gln
            35                  40                  45

Pro Pro Arg Leu Leu Ile Tyr Lys Ile Ser Asn Arg Phe Ser Gly Val
    50                  55                  60

Pro Asp Arg Phe Ser Gly Ser Gly Ala Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Thr His Glu Pro Tyr Thr Phe Gly Gln Gly Lys Leu Glu Ile Lys
            100                 105                 110
```

<210> SEQ ID NO 7
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Met Asp Val Val Met Thr Gln Ser Pro Leu Ser Leu Pro Val Thr Leu
1               5                   10                  15

Gly Gln Pro Ala Ser Ile Ser Cys Arg Ser Ser Gln Ser Leu Val His
            20                  25                  30

Ser Asn Gly Asn Thr Tyr Leu Ser Trp Leu Gln Gln Arg Pro Gly Gln
            35                  40                  45

Pro Pro Arg Leu Leu Ile Tyr Lys Ile Ser Asn Arg Phe Ser Gly Val
    50                  55                  60

Pro Asp Arg Phe Ser Gly Ser Gly Ala Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Thr His Glu Pro Tyr Thr Phe Gly Gln Gly Lys Leu Glu Ile Lys
            100                 105                 110
```

<210> SEQ ID NO 8
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Asp Ile Val Met Thr Gln Thr Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Asn Gly Asn Thr Tyr Leu Asn Trp Tyr Gln Gln Thr Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Val Pro Tyr Thr Phe Gly Gln Gly Lys Leu Glu Ile Lys
            100                 105                 110
```

<210> SEQ ID NO 9
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

```
Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu Asn Trp Tyr Gln Gln Lys Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Glu Pro Tyr Thr Phe Gly Gln Gly Lys Leu Glu Ile Lys
            100                 105                 110
```

<210> SEQ ID NO 10
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

```
Asp Ile Val Met Thr Gln Thr Pro Leu Ser Leu Pro Val Thr Leu Gly
```

```
                1               5                  10                 15
Gln Pro Ala Ser Ile Ser Cys Arg Ser Ser Gln Ser Leu Val His Ser
            20                  25                 30

Asn Gly Asn Thr Tyr Leu Ser Trp Leu Gln Gln Arg Pro Gly Gln Pro
            35                  40                 45

Pro Arg Leu Leu Ile Tyr Lys Ile Ser Asn Arg Phe Ser Gly Val Pro
            50                  55                 60

Asp Arg Phe Ser Gly Ser Gly Ala Gly Thr Asp Phe Thr Leu Lys Ile
65                  70                  75                     80

Ser Arg Val Glu Ala Glu Asp Val Gly Val Tyr Tyr Cys Met Gln Gly
                85                  90                 95

Thr His Glu Pro Tyr Thr Phe Gly Gln Gly Lys Leu Glu Ile Lys
            100                 105                110

<210> SEQ ID NO 11
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (2)..(2)
<223> OTHER INFORMATION: /replace="Val"
<220> FEATURE:
<221> NAME/KEY: misc_feature
<222> LOCATION: (2)..(2)
<223> OTHER INFORMATION: /note="Residue given in the sequence has no
      preference with respect to those in the annotations for said
      position"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: misc_feature
<222> LOCATION: (7)..(7)
<223> OTHER INFORMATION: /note="Residue given in the sequence has no
      preference with respect to those in the annotations for said
      position"
<220> FEATURE:
<221> NAME/KEY: VARIANT
<222> LOCATION: (30)..(30)
<223> OTHER INFORMATION: /replace="Val"
<220> FEATURE:
<221> NAME/KEY: misc_feature
<222> LOCATION: (30)..(30)
<223> OTHER INFORMATION: /note="Residue given in the sequence has no
      preference with respect to those in the annotations for said
      position"
<220> FEATURE:
<221> NAME/KEY: VARIANT
<222> LOCATION: (39)..(39)
<223> OTHER INFORMATION: /replace="Ser"
<220> FEATURE:
<221> NAME/KEY: misc_feature
<222> LOCATION: (39)..(39)
<223> OTHER INFORMATION: /note="Residue given in the sequence has no
      preference with respect to those in the annotations for said
      position"
<220> FEATURE:
<221> NAME/KEY: VARIANT
<222> LOCATION: (41)..(41)
<223> OTHER INFORMATION: /replace="Tyr"
<220> FEATURE:
<221> NAME/KEY: misc_feature
<222> LOCATION: (41)..(41)
<223> OTHER INFORMATION: /note="Residue given in the sequence has no
      preference with respect to those in the annotations for said
      position"
<220> FEATURE:
```

```
<221> NAME/KEY: VARIANT
<222> LOCATION: (44)..(44)
<223> OTHER INFORMATION: /replace="Arg" or "Thr"
<220> FEATURE:
<221> NAME/KEY: misc_feature
<222> LOCATION: (44)..(44)
<223> OTHER INFORMATION: /note="Residue given in the sequence has no
      preference with respect to those in the annotations for said
      position"
<220> FEATURE:
<221> NAME/KEY: VARIANT
<222> LOCATION: (99)..(99)
<223> OTHER INFORMATION: /replace="Val"
<220> FEATURE:
<221> NAME/KEY: misc_feature
<222> LOCATION: (99)..(99)
<223> OTHER INFORMATION: /note="Residue given in the sequence has no
      preference with respect to those in the annotations for said
      position"

<400> SEQUENCE: 11

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Asn Gly Asn Thr Tyr Leu Asn Trp Leu Gln Gln Lys Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Glu Pro Tyr Thr Phe Gly Gln Gly Leu Glu Ile Lys
            100                 105                 110

<210> SEQ ID NO 12
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Syntheticpeptide"

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Asp Met His Trp Val Arg Gln Ala Pro Gly Gln Gly Leu Glu Trp Met
        35                  40                  45

Gly Trp Ile Asp Pro Asn Ser Gly Gly Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Thr Gly

<210> SEQ ID NO 13
<211> LENGTH: 98
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Asp Met His Trp Val Arg Gln Ala Pro Gly Gln Gly Leu Glu Trp Met
        35                  40                  45

Gly Trp Ile Asp Pro Asn Ser Gly Gly Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Gly

<210> SEQ ID NO 14
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Syntheticpeptide"

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Asp Met His Trp Val Arg Gln Ala Pro Gly Gln Gly Leu Glu Trp Met
        35                  40                  45

Gly Trp Ile Asp Pro Arg Ser Gly Asp Thr Ser Tyr Lys Gln Lys Phe
    50                  55                  60

Gln Gly Arg Val Thr Met Thr Arg Asp Thr Ser Ile Ser Thr Ala Tyr
65                  70                  75                  80

Met Glu Leu His Arg Leu Arg Ser Asp Asp Thr Ala Val Tyr Tyr Cys
                85                  90                  95

Thr Gly

<210> SEQ ID NO 15
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Syntheticpeptide"

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45
```

```
Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg

<210> SEQ ID NO 16
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Syntheticpeptide"
<220> FEATURE:
<221> NAME/KEY: VARIANT
<222> LOCATION: (31)..(31)
<223> OTHER INFORMATION: /replace="Ala"
<220> FEATURE:
<221> NAME/KEY: misc_feature
<222> LOCATION: (31)..(31)
<223> OTHER INFORMATION: /note="Residue given in the sequence has no
      preference with respect to those in the annotations for said
      position"
<220> FEATURE:
<221> NAME/KEY: VARIANT
<222> LOCATION: (33)..(33)
<223> OTHER INFORMATION: /replace="Tyr"
<220> FEATURE:
<221> NAME/KEY: misc_feature
<222> LOCATION: (33)..(33)
<223> OTHER INFORMATION: /note="Residue given in the sequence has no
      preference with respect to those in the annotations for said
      position"
<220> FEATURE:
<221> NAME/KEY: VARIANT
<222> LOCATION: (52)..(52)
<223> OTHER INFORMATION: /replace="Asn"
<220> FEATURE:
<221> NAME/KEY: misc_feature
<222> LOCATION: (52)..(52)
<223> OTHER INFORMATION: /note="Residue given in the sequence has no
      preference with respect to those in the annotations for said
      position"
<220> FEATURE:
<221> NAME/KEY: VARIANT
<222> LOCATION: (54)..(54)
<223> OTHER INFORMATION: /replace="Arg"
<220> FEATURE:
<221> NAME/KEY: misc_feature
<222> LOCATION: (54)..(54)
<223> OTHER INFORMATION: /note="Residue given in the sequence has no
      preference with respect to those in the annotations for said
      position"
<220> FEATURE:
<221> NAME/KEY: VARIANT
<222> LOCATION: (57)..(57)
<223> OTHER INFORMATION: /replace="Asp"
<220> FEATURE:
<221> NAME/KEY: misc_feature
<222> LOCATION: (57)..(57)
<223> OTHER INFORMATION: /note="Residue given in the sequence has no
      preference with respect to those in the annotations for said
      position"
<220> FEATURE:
<221> NAME/KEY: VARIANT
<222> LOCATION: (59)..(59)
<223> OTHER INFORMATION: /replace="Arg" or "Ser"
<220> FEATURE:
<221> NAME/KEY: misc_feature
<222> LOCATION: (59)..(59)
<223> OTHER INFORMATION: /note="Residue given in the sequence has no
      preference with respect to those in the annotations for said
      position"
```

```
<220> FEATURE:
<221> NAME/KEY: VARIANT
<222> LOCATION: (61)..(61)
<223> OTHER INFORMATION: /replace="Lys"
<220> FEATURE:
<221> NAME/KEY: misc_feature
<222> LOCATION: (61)..(61)
<223> OTHER INFORMATION: /note="Residue given in the sequence has no
      preference with respect to those in the annotations for said
      position"
<220> FEATURE:
<221> NAME/KEY: VARIANT
<222> LOCATION: (84)..(84)
<223> OTHER INFORMATION: /replace="Ser"
<220> FEATURE:
<221> NAME/KEY: misc_feature
<222> LOCATION: (84)..(84)
<223> OTHER INFORMATION: /note="Residue given in the sequence has no
      preference with respect to those in the annotations for said
      position"
<220> FEATURE:
<221> NAME/KEY: VARIANT
<222> LOCATION: (87)..(87)
<223> OTHER INFORMATION: /replace="Thr"
<220> FEATURE:
<221> NAME/KEY: misc_feature
<222> LOCATION: (87)..(87)
<223> OTHER INFORMATION: /note="Residue given in the sequence has no
      preference with respect to those in the annotations for said
      position"
<220> FEATURE:
<221> NAME/KEY: VARIANT
<222> LOCATION: (97)..(97)
<223> OTHER INFORMATION: /replace="Thr"
<220> FEATURE:
<221> NAME/KEY: VARIANT
<222> LOCATION: (98)..(98)
<223> OTHER INFORMATION: /replace="Arg"
<220> FEATURE:
<221> NAME/KEY: misc_feature
<222> LOCATION: (97)..(98)
<223> OTHER INFORMATION: /note="Residues given in the sequence have no
      preference with respect to those in the annotations for said
      positions"

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Asp Met His Trp Val Arg Gln Ala Pro Gly Gln Gly Leu Glu Trp Met
            35                  40                  45

Gly Trp Ile Asp Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu His Arg Leu Arg Ser Asp Asp Thr Ala Val Tyr Tyr Cys
                85                  90                  95

Ala Gly

<210> SEQ ID NO 17
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Met Asp Val Val Met Thr Gln Ser Pro Leu Ser Leu Pro Val Thr Leu
```

```
1               5                   10                  15
Gly Gln Pro Ala Ser Ile Ser Cys Arg Ser Ser Gln Ser Leu Leu His
            20                  25                  30

Ser Asn Gly Asn Thr Tyr Leu Asn Trp Tyr Gln Gln Thr Pro Gly Gln
            35                  40                  45

Pro Pro Arg Leu Leu Ile Tyr Lys Ile Ser Asn Arg Phe Ser Gly Val
            50                  55                  60

Pro Asp Arg Phe Ser Gly Ser Gly Ala Gly Thr Asp Phe Thr Leu Lys
65                  70                  75                  80

Ile Ser Arg Val Glu Ala Glu Asp Val Gly Val Tyr Tyr Cys
                85                  90
```

<210> SEQ ID NO 18
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

```
Met Asp Val Val Met Thr Gln Ser Pro Leu Ser Leu Pro Val Thr Leu
1               5                   10                  15

Gly Gln Pro Ala Ser Ile Ser Cys Arg Ser Ser Gln Ser Leu Val His
            20                  25                  30

Ser Asn Gly Asn Thr Tyr Leu Asn Trp Tyr Gln Gln Lys Pro Gly Gln
            35                  40                  45

Pro Pro Arg Leu Leu Ile Tyr Lys Ile Ser Asn Arg Phe Ser Gly Val
            50                  55                  60

Pro Asp Arg Phe Ser Gly Ser Gly Ala Gly Thr Asp Phe Thr Leu Lys
65                  70                  75                  80

Ile Ser Arg Val Glu Ala Glu Asp Val Gly Val Tyr Tyr Cys
                85                  90
```

<210> SEQ ID NO 19
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Syntheticpeptide"

<400> SEQUENCE: 19

```
Met Asp Val Val Met Thr Gln Ser Pro Leu Ser Leu Pro Val Thr Leu
1               5                   10                  15

Gly Gln Pro Ala Ser Ile Ser Cys Arg Ser Ser Gln Ser Leu Val His
            20                  25                  30

Ser Asn Gly Asn Thr Tyr Leu Ser Trp Leu Gln Gln Arg Pro Gly Gln
            35                  40                  45

Pro Pro Arg Leu Leu Ile Tyr Lys Ile Ser Asn Arg Phe Ser Gly Val
            50                  55                  60

Pro Asp Arg Phe Ser Gly Ser Gly Ala Gly Thr Asp Phe Thr Leu Lys
65                  70                  75                  80

Ile Ser Arg Val Glu Ala Glu Asp Val Gly Val Tyr Tyr Cys
                85                  90
```

<210> SEQ ID NO 20
<211> LENGTH: 93

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Asp Ile Val Met Thr Gln Thr Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Asn Gly Asn Thr Tyr Leu Asn Trp Tyr Gln Gln Thr Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys
                85                  90

<210> SEQ ID NO 21
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Syntheticpeptide"

<400> SEQUENCE: 21

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu Asn Trp Tyr Gln Gln Lys Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys
                85                  90

<210> SEQ ID NO 22
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Asp Ile Val Met Thr Gln Thr Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60
```

```
Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys
                 85                  90

<210> SEQ ID NO 23
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Syntheticpeptide"

<400> SEQUENCE: 23

Asp Ile Val Met Thr Gln Thr Pro Leu Ser Pro Val Thr Leu Gly
 1               5                  10                  15

Gln Pro Ala Ser Ile Ser Cys Arg Ser Ser Gln Ser Leu Val His Ser
                20                  25                  30

Asp Gly Asn Thr Tyr Leu Ser Trp Leu Gln Gln Arg Pro Gly Gln Pro
             35                  40                  45

Pro Arg Leu Leu Ile Tyr Lys Ile Ser Asn Arg Phe Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys
                 85                  90

<210> SEQ ID NO 24
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Syntheticpolypeptide"
<220> FEATURE:
<221> NAME/KEY: VARIANT
<222> LOCATION: (2)..(2)
<223> OTHER INFORMATION: /replace="Val"
<220> FEATURE:
<221> NAME/KEY: misc_feature
<222> LOCATION: (2)..(2)
<223> OTHER INFORMATION: /note="Residue given in the sequence has no
      preference with respect to those in the annotations for said
      position"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: misc_feature
<222> LOCATION: (7)..(7)
<223> OTHER INFORMATION: /note="Residue given in the sequence has no
      preference with respect to those in the annotations for said
      position"
<220> FEATURE:
<221> NAME/KEY: VARIANT
<222> LOCATION: (11)..(11)
<223> OTHER INFORMATION: /replace="Ser"
<220> FEATURE:
<221> NAME/KEY: misc_feature
<222> LOCATION: (11)..(11)
<223> OTHER INFORMATION: /note="Residue given in the sequence has no
      preference with respect to those in the annotations for said
      position"
<220> FEATURE:
<221> NAME/KEY: VARIANT
<222> LOCATION: (30)..(30)
<223> OTHER INFORMATION: /replace="Val"
```

```
<220> FEATURE:
<221> NAME/KEY: misc_feature
<222> LOCATION: (30)..(30)
<223> OTHER INFORMATION: /note="Residue given in the sequence has no
      preference with respect to those in the annotations for said
      position"
<220> FEATURE:
<221> NAME/KEY: VARIANT
<222> LOCATION: (33)..(33)
<223> OTHER INFORMATION: /replace="Asn"
<220> FEATURE:
<221> NAME/KEY: misc_feature
<222> LOCATION: (33)..(33)
<223> OTHER INFORMATION: /note="Residue given in the sequence has no
      preference with respect to those in the annotations for said
      position"
<220> FEATURE:
<221> NAME/KEY: VARIANT
<222> LOCATION: (39)..(39)
<223> OTHER INFORMATION: /replace="Ser"
<220> FEATURE:
<221> NAME/KEY: misc_feature
<222> LOCATION: (39)..(39)
<223> OTHER INFORMATION: /note="Residue given in the sequence has no
      preference with respect to those in the annotations for said
      position"
<220> FEATURE:
<221> NAME/KEY: VARIANT
<222> LOCATION: (41)..(41)
<223> OTHER INFORMATION: /replace="Tyr"
<220> FEATURE:
<221> NAME/KEY: misc_feature
<222> LOCATION: (41)..(41)
<223> OTHER INFORMATION: /note="Residue given in the sequence has no
      preference with respect to those in the annotations for said
      position"
<220> FEATURE:
<221> NAME/KEY: VARIANT
<222> LOCATION: (44)..(44)
<223> OTHER INFORMATION: /replace="Arg" or "Thr"
<220> FEATURE:
<221> NAME/KEY: misc_feature
<222> LOCATION: (44)..(44)
<223> OTHER INFORMATION: /note="Residue given in the sequence has no
      preference with respect to those in the annotations for said
      position"

<400> SEQUENCE: 24

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Asp Gly Asn Thr Tyr Leu Asn Trp Leu Gln Gln Lys Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys
                85                  90

<210> SEQ ID NO 25
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Ala Tyr Asp Met His
```

<210> SEQ ID NO 26
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gly Tyr Tyr Met His
1               5

<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Gly"
<220> FEATURE:
<221> NAME/KEY: misc_feature
<222> LOCATION: (1)..(1)
<223> OTHER INFORMATION: /note="Residue given in the sequence has no
      preference with respect to those in the annotations for said
      position"
<220> FEATURE:
<221> NAME/KEY: VARIANT
<222> LOCATION: (3)..(3)
<223> OTHER INFORMATION: /replace="Tyr"
<220> FEATURE:
<221> NAME/KEY: misc_feature
<222> LOCATION: (3)..(3)
<223> OTHER INFORMATION: /note="Residue given in the sequence has no
      preference with respect to those in the annotations for said
      position"

<400> SEQUENCE: 27

Ala Tyr Asp Met His
1               5

<210> SEQ ID NO 28
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Trp Ile Asp Pro Asn Ser Gly Gly Thr Arg Tyr Ala Gln Lys Phe Gln
1               5                   10                  15

Gly

<210> SEQ ID NO 29
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Syntheticpeptide"

<400> SEQUENCE: 29

-continued

```
Trp Ile Asp Pro Arg Ser Gly Asp Thr Ser Tyr Lys Gln Lys Phe Gln
1               5                   10                  15

Gly

<210> SEQ ID NO 30
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Trp Ile Asn Pro Asn Ser Gly Gly Thr Asn Tyr Ala Gln Lys Phe Gln
1               5                   10                  15

Gly

<210> SEQ ID NO 31
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Asn"
<220> FEATURE:
<221> NAME/KEY: misc_feature
<222> LOCATION: (3)..(3)
<223> OTHER INFORMATION: /note="Residue given in the sequence has no
      preference with respect to those in the annotations for said
      position"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: misc_feature
<222> LOCATION: (5)..(5)
<223> OTHER INFORMATION: /note="Residue given in the sequence has no
      preference with respect to those in the annotations for said
      position"
<220> FEATURE:
<221> NAME/KEY: VARIANT
<222> LOCATION: (8)..(8)
<223> OTHER INFORMATION: /replace="Asp"
<220> FEATURE:
<221> NAME/KEY: misc_feature
<222> LOCATION: (8)..(8)
<223> OTHER INFORMATION: /note="Residue given in the sequence has no
      preference with respect to those in the annotations for said
      position"
<220> FEATURE:
<221> NAME/KEY: VARIANT
<222> LOCATION: (10)..(10)
<223> OTHER INFORMATION: /replace="Arg" or "Ser"
<220> FEATURE:
<221> NAME/KEY: misc_feature
<222> LOCATION: (10)..(10)
<223> OTHER INFORMATION: /note="Residue given in the sequence has no
      preference with respect to those in the annotations for said
      position"
<220> FEATURE:
<221> NAME/KEY: VARIANT
<222> LOCATION: (12)..(12)
<223> OTHER INFORMATION: /replace="Lys"
<220> FEATURE:
<221> NAME/KEY: misc_feature
<222> LOCATION: (12)..(12)
<223> OTHER INFORMATION: /note="Residue given in the sequence has no
``` preference with respect to those in the annotations for said
position"

<400> SEQUENCE: 31

Trp Ile Asp Pro Asn Ser Gly Gly Thr Asn Tyr Ala Gln Lys Phe Gln
1               5                   10                  15

Gly

<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Val Thr Thr Trp Phe Ala Tyr
1               5

<210> SEQ ID NO 33
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Val Thr Ser Trp Phe Ala Tyr
1               5

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Val"
<220> FEATURE:
<221> NAME/KEY: VARIANT
<222> LOCATION: (3)..(3)
<223> OTHER INFORMATION: /replace="Thr" or "Arg" or "Asn"
<220> FEATURE:
<221> NAME/KEY: misc_feature
<222> LOCATION: (2)..(3)
<223> OTHER INFORMATION: /note="Residues given in the sequence have no
      preference with respect to those in the annotations for said
      positions"

<400> SEQUENCE: 34

Val Thr Ser Trp Phe Ala Tyr
1               5

<210> SEQ ID NO 35
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Syntheticpeptide"

<400> SEQUENCE: 35

-continued

Arg Ser Ser Gln Ser Leu Leu His Ser Asn Gly Asn Thr Tyr Leu Asn
1               5                   10                  15

<210> SEQ ID NO 36
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Arg Ser Ser Gln Ser Leu Val His Ser Asn Gly Asn Thr Tyr Leu Asn
1               5                   10                  15

<210> SEQ ID NO 37
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Arg Ser Ser Gln Ser Leu Val His Ser Asn Gly Asn Thr Tyr Leu Ser
1               5                   10                  15

<210> SEQ ID NO 38
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (7)..(7)
<223> OTHER INFORMATION: /replace="Val"
<220> FEATURE:
<221> NAME/KEY: misc_feature
<222> LOCATION: (7)..(7)
<223> OTHER INFORMATION: /note="Residue given in the sequence has no
      preference with respect to those in the annotations for said
      position"
<220> FEATURE:
<221> NAME/KEY: VARIANT
<222> LOCATION: (16)..(16)
<223> OTHER INFORMATION: /replace="Ser"
<220> FEATURE:
<221> NAME/KEY: misc_feature
<222> LOCATION: (16)..(16)
<223> OTHER INFORMATION: /note="Residue given in the sequence has no
      preference with respect to those in the annotations for said
      position"

<400> SEQUENCE: 38

Arg Ser Ser Gln Ser Leu Leu His Ser Asn Gly Asn Thr Tyr Leu Asn
1               5                   10                  15

<210> SEQ ID NO 39
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

```
Lys Ile Ser Asn Arg Phe Ser
1               5

<210> SEQ ID NO 40
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Met Gln Gly Thr His Glu Pro Tyr Thr
1               5

<210> SEQ ID NO 41
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Met Gln Gly Thr His Val Pro Tyr Thr
1               5

<210> SEQ ID NO 42
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Met"
<220> FEATURE:
<221> NAME/KEY: misc_feature
<222> LOCATION: (1)..(1)
<223> OTHER INFORMATION: /note="Residue given in the sequence has no
      preference with respect to those in the annotations for said
      position"
<220> FEATURE:
<221> NAME/KEY: VARIANT
<222> LOCATION: (5)..(5)
<223> OTHER INFORMATION: /replace="Ala"
<220> FEATURE:
<221> NAME/KEY: VARIANT
<222> LOCATION: (6)..(6)
<223> OTHER INFORMATION: /replace="Val" or "Ile"
<220> FEATURE:
<221> NAME/KEY: misc_feature
<222> LOCATION: (5)..(6)
<223> OTHER INFORMATION: /note="Residues given in the sequence have no
      preference with respect to those in the annotations for said
      positions"

<400> SEQUENCE: 42

Ser Gln Gly Thr His Glu Pro Tyr Thr
1               5

<210> SEQ ID NO 43
<211> LENGTH: 30
<212> TYPE: PRT
<213> ORGANISM: Artificial Sequence
<220> FEATURE:
<221> NAME/KEY: source
```

-continued

<223> OTHER INFORMATION: /note="Description of Artificial Sequence:
      Synthetic peptide"

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 44
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Trp Val Arg Gln Ala Pro Gly Gln Gly Leu Glu Trp Met Gly
1               5                   10

<210> SEQ ID NO 45
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Arg Val Thr Met Thr Arg Asp Thr Ser Ile Ser Thr Ala Tyr Met Glu
1               5                   10                  15

Leu Ser Arg Leu Thr Ser Asp Asp Thr Ala Val Tyr Tyr Cys Thr Gly
            20                  25                  30

<210> SEQ ID NO 46
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Arg Val Thr Met Thr Arg Asp Thr Ser Ile Ser Thr Ala Tyr Met Glu
1               5                   10                  15

Leu His Arg Leu Arg Ser Asp Asp Thr Ala Val Tyr Tyr Cys Thr Gly
            20                  25                  30

<210> SEQ ID NO 47
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Arg Val Thr Met Thr Arg Asp Thr Ser Ile Ser Thr Ala Tyr Met Glu
1               5                   10                  15

Leu Ser Arg Leu Thr Ser Asp Asp Thr Ala Val Tyr Tyr Cys Ala Gly
            20                  25                  30

-continued

```
<210> SEQ ID NO 48
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 49
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (18)..(18)
<223> OTHER INFORMATION: /replace="Ser"
<220> FEATURE:
<221> NAME/KEY: misc_feature
<222> LOCATION: (18)..(18)
<223> OTHER INFORMATION: /note="Residue given in the sequence has no
      preference with respect to those in the annotations for said
      position"
<220> FEATURE:
<221> NAME/KEY: VARIANT
<222> LOCATION: (21)..(21)
<223> OTHER INFORMATION: /replace="Thr"
<220> FEATURE:
<221> NAME/KEY: misc_feature
<222> LOCATION: (21)..(21)
<223> OTHER INFORMATION: /note="Residue given in the sequence has no
      preference with respect to those in the annotations for said
      position"
<220> FEATURE:
<221> NAME/KEY: VARIANT
<222> LOCATION: (31)..(31)
<223> OTHER INFORMATION: /replace="Thr"
<220> FEATURE:
<221> NAME/KEY: VARIANT
<222> LOCATION: (32)..(32)
<223> OTHER INFORMATION: /replace="Arg"
<220> FEATURE:
<221> NAME/KEY: misc_feature
<222> LOCATION: (31)..(32)
<223> OTHER INFORMATION: /note="Residues given in the sequence have no
      preference with respect to those in the annotations for said
      positions"

<400> SEQUENCE: 49

Arg Val Thr Met Thr Arg Asp Thr Ser Ile Ser Thr Ala Tyr Met Glu
1               5                   10                  15

Leu His Arg Leu Arg Ser Asp Asp Thr Ala Val Tyr Tyr Cys Ala Gly
            20                  25                  30

<210> SEQ ID NO 50
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 50

Trp Gly Gln Gly Thr Leu Val Thr Val Ser Ser
1               5                   10

<210> SEQ ID NO 51
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Met Asp Val Val Met Thr Gln Ser Pro Leu Ser Leu Pro Val Thr Leu
1               5                   10                  15

Gly Gln Pro Ala Ser Ile Ser Cys
            20

<210> SEQ ID NO 52
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Asp Ile Val Met Thr Gln Thr Pro Leu Ser Leu Pro Val Thr Leu Gly
1               5                   10                  15

Gln Pro Ala Ser Ile Ser Cys
            20

<210> SEQ ID NO 53
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Asp Ile Val Met Thr Gln Ser Pro Leu Ser Leu Pro Val Thr Leu Gly
1               5                   10                  15

Gln Pro Ala Ser Ile Ser Cys
            20

<210> SEQ ID NO 54
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Asp Ile Val Met Thr Gln Thr Pro Leu Ser Ser Pro Val Thr Leu Gly
1               5                   10                  15

Gln Pro Ala Ser Ile Ser Cys
            20

<210> SEQ ID NO 55
<211> LENGTH: 23
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: misc_feature
<222> LOCATION: (7)..(7)
<223> OTHER INFORMATION: /note="Residue given in the sequence has no
      preference with respect to those in the annotations for said
      position"
<220> FEATURE:
<221> NAME/KEY: VARIANT
<222> LOCATION: (11)..(11)
<223> OTHER INFORMATION: /replace="Ser"
<220> FEATURE:
<221> NAME/KEY: misc_feature
<222> LOCATION: (11)..(11)
<223> OTHER INFORMATION: /note="Residue given in the sequence has no
      preference with respect to those in the annotations for said
      position"

<400> SEQUENCE: 55

Asp Ile Val Met Thr Gln Ser Pro Leu Ser Leu Pro Val Thr Leu Gly
1               5                   10                  15

Gln Pro Ala Ser Ile Ser Cys
            20

<210> SEQ ID NO 56
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Trp Tyr Gln Gln Thr Pro Gly Gln Pro Pro Arg Leu Leu Ile Tyr
1               5                   10                  15

<210> SEQ ID NO 57
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Trp Tyr Gln Gln Lys Pro Gly Gln Pro Pro Arg Leu Leu Ile Tyr
1               5                   10                  15

<210> SEQ ID NO 58
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Trp Leu Gln Gln Arg Pro Gly Gln Pro Pro Arg Leu Leu Ile Tyr
1               5                   10                  15
```

```
<210> SEQ ID NO 59
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Tyr"
<220> FEATURE:
<221> NAME/KEY: misc_feature
<222> LOCATION: (2)..(2)
<223> OTHER INFORMATION: /note="Residue given in the sequence has no
      preference with respect to those in the annotations for said
      position"
<220> FEATURE:
<221> NAME/KEY: VARIANT
<222> LOCATION: (5)..(5)
<223> OTHER INFORMATION: /replace="Arg" or "Thr"
<220> FEATURE:
<221> NAME/KEY: misc_feature
<222> LOCATION: (5)..(5)
<223> OTHER INFORMATION: /note="Residue given in the sequence has no
      preference with respect to those in the annotations for said
      position"

<400> SEQUENCE: 59

Trp Leu Gln Gln Lys Pro Gly Gln Pro Pro Arg Leu Leu Ile Tyr
1               5                   10                  15

<210> SEQ ID NO 60
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gly Val Pro Asp Arg Phe Ser Gly Ser Gly Ala Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 61
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Phe Gly Gln Gly Lys Leu Glu Ile Lys
1               5

<210> SEQ ID NO 62
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62
```

```
caggtgcagc tggtgcagtc tggggctgag gtgaagaagc ctggggcctc agtgaaggtc    60
tcctgcaagg cctctggata caccttcacc gcctacgata tgcactgggt gcgacaggcc   120
cctggacaag gcttgagtg atggggtgg atcgaccta acagtggtgg cacaaggtat     180
gcacagaagt tcagggcag ggtcaccatg accaggaca cgtccatcag tacagcctac    240
atggagctga gcaggctgac atctgacgac acggccgtgt actactgcac aggtgttacg   300
acctggtttg cgtactgggg tcaaggtacc ctggtgaccg tgagctcc              348

<210> SEQ ID NO 63
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 63
caggttcagc tggtgcagtc tggggctgag gtgaagaagc ctggggcctc agtgaaggtc    60
tcctgcaagg cctctggata caccttcacc gcctacgata tgcactgggt gcggcaggcc   120
cctggacaag gcttgagtg atgggctgg atcgacccta gaagtggtga cacaagctat    180
aaacagaagt tcagggcag ggtcaccatg accaggaca cgtccatcag cacagcctac    240
atggagctgc acaggctgag atctgacgac acagctgtgt actactgcac aggtgttacg   300
acctggtttg cgtactgggg tcaaggtacc ctggtgaccg tgagctcc              348

<210> SEQ ID NO 64
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 64
caggtgcagc tggtgcagtc tggggctgag gtgaagaagc ctggggcctc agtgaaggtc    60
tcctgcaagg cctctggata caccttcacc gcctacgata tgcactgggt gcgacaggcc   120
cctggacaag gcttgagtg atgggatgg atcgacccta acagtggtgg cacaaggtat    180
gcacagaagt tcagggcag ggtcaccatg accaggaca cgtccatcag tacagcctac    240
atggagctga gcaggctgac atctgacgac acggccgtgt actactgcgc aggtgttacg   300
agctggtttg cgtactgggg tcaaggtacc ctggtgaccg tgagctccgc tagc        354

<210> SEQ ID NO 65
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65
atggatgttg tgatgactca gtctccactc tccctgcccg tcacccttgg acagccggcc    60
tccatctcct gcaggtccag tcaaagcctc ctacatagta tggaaacac ctacttgaat    120 tggtatcagc agacgccagg ccagcctcca gactcctga tttataagat ttctaaccgg   180
ttctctgggg tcccggacag attcagtggc agtggggcag ggacagattt cacactgaaa   240
```

| | |
|---|---|
| atcagcaggg tggaagctga ggatgttgga gtttactact gcatgcaagg tacacatgag | 300 |
| ccgtacacgt ttggccaagg tacgaaactg gaaattaaa | 339 |

<210> SEQ ID NO 66
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 66

| | |
|---|---|
| atggatgttg tgatgactca gtctccactc tccctgcccg tcacccttgg acagccggcc | 60 |
| tccatctcct gcaggtctag tcaaagcctc gtacacagta atggaaacac ctacttgaat | 120 |
| tggtatcagc agaagccagg ccagcctcca agactcctga tttataagat ttctaaccgg | 180 |
| ttctctgggg tcccggacag attcagtggc agtggggcag ggacagattt cacactgaaa | 240 |
| atcagcaggg tggaagctga ggatgttgga gtttactact gcatgcaagg tacacatgag | 300 |
| ccgtacacgt ttggccaagg tacgaaactg gaaattaaa | 339 |

<210> SEQ ID NO 67
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 67

| | |
|---|---|
| atggatgttg tgatgactca gtctccactc tccctgcccg tcacccttgg acagccggcc | 60 |
| tccatctcct gcaggtctag tcaaagcctc gtacacagta atggaaacac ctacttgagt | 120 |
| tggcttcagc agaggccagg ccagcctcca agactcctga tttataagat ttctaaccgg | 180 |
| ttctctgggg tcccggacag attcagtggc agtggggcag ggacagattt cacactgaaa | 240 |
| atcagcaggg tggaagctga ggatgttgga gtttactact gcatgcaagg tacacatgag | 300 |
| ccgtacacgt ttggccaagg tacgaaactg gaaattaaa | 339 |

<210> SEQ ID NO 68
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 68

| | |
|---|---|
| caggtgcagc tggtgcagtc tggggctgag gtgaagaagc ctggggcctc agtgaaggtc | 60 |
| tcctgcaagg cctctggata caccttcacc gcctacgata tgcactgggt gcgacaggcc | 120 |
| cctggacaag gcttgagtg gatgggatgg atcgaccccta acagtggtgg cacaaggtat | 180 |
| gcacagaagt tcagggcag ggtcaccatg accagggaca cgtccatcag tacagcctac | 240 |
| atggagctga gcaggctgac atctgacgac acagctgtgt actactgcac aggtgttacg | 300 |
| acctggtttg cgtactgggg tcaaggtacc ctggtcactg tctcttct | 348 |

<210> SEQ ID NO 69
<211> LENGTH: 348
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 69

```
caggtgcagc tggtgcagtc tggggctgag gtgaagaagc ctggggcctc agtgaaggtc     60
tcctgcaagg cctctggata caccttcacc gcctacgata tgcactgggt gcggcaggcc    120
cctggacaag ggcttgagtg gatgggctgg atcgaccctg aagtggtga cacaagctat    180 aaacagaagt tcagggcag ggtcaccatg accaggaca cgtccatcag cacagcctac     240
atggagctgc acaggctgag atctgacgac acagccgtgt actactgcac aggtgttacg    300
acctggtttg cgtactgggg tcaaggtacc ctggtcactg tctcttct                348
```

<210> SEQ ID NO 70
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 70

```
caggtgcagc tggtgcagtc tggggctgag gtgaagaagc ctggggcctc agtgaaggtc     60
tcctgcaagg cctctggata caccttcacc gcctacgata tgcactgggt gcgacaggcc    120
cctggacaag ggcttgagtg gatgggatgg atcgaccctg acagtggtgg cacaaggtat    180
gcacagaagt tcagggcag ggtcaccatg accaggaca cgtccatcag tacagcctac     240
atggagctga gcaggctgac atctgacgac acggccgtgt actactgcgc aggtgttacg    300
agctggtttg cgtactgggg tcaaggtacc ctggtgaccg tgagctcc                348
```

<210> SEQ ID NO 71
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 71

```
gatattgtga tgactcagac tccactctcc ctgcccgtca cccttggaca gccggcctcc     60
atctcctgca ggtccagtca agcctccta catagtaatg aaacaccta cttgaattgg    120 tatcagcaga cgccaggcca gcctccaaga ctcctgattt ataagatttc taaccggttc    180
tctggggtcc cggacagatt cagtggcagt ggggcaggga cagatttcac actgaaaatc    240
agcagggtgg aagctgagga tgttggagtt tactactgca tgcaaggtac acatgtgccg    300
tacacgtttg gccaaggtac gaaactggaa attaaa                              336
```

<210> SEQ ID NO 72
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 72

```
gatattgtga tgactcagtc tccactctcc ctgcccgtca cccttggaca gccggcctcc    60
atctcctgca ggtctagtca aagcctcgta cacagtaatg gaaacaccta cttgaattgg   120
tatcagcaga agccaggcca gcctccaaga ctcctgattt ataagatttc taaccggttc   180
tctggggtcc cggacagatt cagtggcagt ggggcaggga cagatttcac actgaaaatc   240
agcagggtgg aagctgagga tgttggagtt tactactgca tgcaaggtac acatgagccg   300
tacacgtttg gccaaggtac gaaactggaa attaaa                             336
```

<210> SEQ ID NO 73
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73

```
gatattgtga tgactcagac tccactctcc ctgcccgtca cccttggaca gccggcctcc    60
atctcctgca ggtctagtca aagcctcgta cacagtaatg gaaacaccta cttgagttgg   120
cttcagcaga ggccaggcca gcctccaaga ctcctgattt ataagatttc taaccggttc   180
tctggggtcc cggacagatt cagtggcagt ggggcaggga cagatttcac actgaaaatc   240
agcagggtgg aagctgagga tgttggagtt tactactgca tgcaaggtac acatgagccg   300
tacacgtttg gccaaggtac gaaactggaa attaaa                             336
```

<210> SEQ ID NO 74
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

```
Tyr Phe Asp Tyr Trp Gly Gln Gly Thr Leu Val Thr Val Ser Ser
1               5                   10                  15
```

<210> SEQ ID NO 75
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

```
Tyr Thr Phe Gly Gln Gly Thr Lys Leu Glu Ile Lys
1               5                   10
```

<210> SEQ ID NO 76
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ala Tyr
            20                  25                  30

Asp Met His Trp Val Arg Gln Ala Pro Gly Gln Gly Leu Glu Trp Met
        35                  40                  45

Gly Trp Ile Asp Pro Asn Ser Gly Gly Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Thr Ala Val Tyr Tyr Cys
            85                  90                  95

Thr Gly Val Thr Thr Trp Phe Ala Tyr
            100                 105

<210> SEQ ID NO 77
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Asp Met His Trp Val Arg Gln Ala Pro Gly Gln Gly Leu Glu Trp Met
        35                  40                  45

Gly Trp Ile Asp Pro Asn Ser Gly Gly Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Thr Ala Val Tyr Tyr Cys
            85                  90                  95

Ala Gly Val Thr Ser Trp Phe Ala Tyr
            100                 105

<210> SEQ ID NO 78
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Asp Met His Trp Val Arg Gln Ala Pro Gly Gln Gly Leu Glu Trp Met
        35                  40                  45

Gly Trp Ile Asp Pro Arg Ser Gly Asp Thr Ser Tyr Lys Gln Lys Phe
    50                  55                  60

Gln Gly Arg Val Thr Met Thr Arg Asp Thr Ser Ile Ser Thr Ala Tyr
65                  70                  75                  80

Met Glu Leu His Arg Leu Arg Ser Asp Asp Thr Ala Val Tyr Tyr Cys
```

```
                    85                  90                  95

Thr Gly Val Thr Thr Trp Phe Ala Tyr
                100                 105
```

<210> SEQ ID NO 79
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro
            100
```

<210> SEQ ID NO 80
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

```
Met Asp Val Val Met Thr Gln Ser Pro Leu Ser Leu Pro Val Thr Leu
1               5                   10                  15

Gly Gln Pro Ala Ser Ile Ser Cys Arg Ser Ser Gln Ser Leu Leu His
            20                  25                  30

Ser Asn Gly Asn Thr Tyr Leu Asn Trp Tyr Gln Gln Thr Pro Gly Gln
        35                  40                  45

Pro Pro Arg Leu Leu Ile Tyr Lys Ile Ser Asn Arg Phe Ser Gly Val
    50                  55                  60

Pro Asp Arg Phe Ser Gly Ser Gly Ala Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Thr His Glu Pro Tyr Thr
            100
```

<210> SEQ ID NO 81
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

```
Met Asp Val Val Met Thr Gln Ser Pro Leu Ser Leu Pro Val Thr Leu
1               5                   10                  15
Gly Gln Pro Ala Ser Ile Ser Cys Arg Ser Ser Gln Ser Leu Val His
            20                  25                  30
Ser Asn Gly Asn Thr Tyr Leu Asn Trp Tyr Gln Gln Lys Pro Gly Gln
        35                  40                  45
Pro Pro Arg Leu Leu Ile Tyr Lys Ile Ser Asn Arg Phe Ser Gly Val
    50                  55                  60
Pro Asp Arg Phe Ser Gly Ser Gly Ala Gly Thr Asp Phe Thr Leu Lys
65                  70                  75                  80
Ile Ser Arg Val Glu Ala Glu Asp Val Gly Val Tyr Tyr Cys Met Gln
                85                  90                  95
Gly Thr His Glu Pro Tyr Thr
            100
```

<210> SEQ ID NO 82
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 82

```
Met Asp Val Val Met Thr Gln Ser Pro Leu Ser Leu Pro Val Thr Leu
1               5                   10                  15
Gly Gln Pro Ala Ser Ile Ser Cys Arg Ser Ser Gln Ser Leu Val His
            20                  25                  30
Ser Asn Gly Asn Thr Tyr Leu Ser Trp Leu Gln Gln Arg Pro Gly Gln
        35                  40                  45
Pro Pro Arg Leu Leu Ile Tyr Lys Ile Ser Asn Arg Phe Ser Gly Val
    50                  55                  60
Pro Asp Arg Phe Ser Gly Ser Gly Ala Gly Thr Asp Phe Thr Leu Lys
65                  70                  75                  80
Ile Ser Arg Val Glu Ala Glu Asp Val Gly Val Tyr Tyr Cys Met Gln
                85                  90                  95
Gly Thr His Glu Pro Tyr Thr
            100
```

<210> SEQ ID NO 83
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 83

```
Asp Ile Val Met Thr Gln Thr Pro Leu Ser Ser Pro Val Thr Leu Gly
1               5                   10                  15
Gln Pro Ala Ser Ile Ser Cys Arg Ser Ser Gln Ser Leu Val His Ser
            20                  25                  30
Asp Gly Asn Thr Tyr Leu Ser Trp Leu Gln Gln Arg Pro Gly Gln Pro
        35                  40                  45
Pro Arg Leu Leu Ile Tyr Lys Ile Ser Asn Arg Phe Ser Gly Val Pro
    50                  55                  60
```

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln

<210> SEQ ID NO 84
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Met Asp Ile Val Met Thr Gln Thr Pro Leu Ser Leu Pro Val Thr Leu
1               5                   10                  15

Gly Gln Pro Ala Ser Ile Ser Cys Arg Ser Ser Gln Ser Leu Leu His
                20                  25                  30

Ser Asn Gly Asn Thr Tyr Leu Asn Trp Tyr Gln Gln Thr Pro Gly Gln
            35                  40                  45

Pro Pro Arg Leu Leu Ile Tyr Lys Ile Ser Asn Arg Phe Ser Gly Val
        50                  55                  60

Pro Asp Arg Phe Ser Gly Ser Gly Ala Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Thr His Val Pro Tyr Thr
            100

<210> SEQ ID NO 85
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Met Asp Ile Val Met Thr Gln Ser Pro Leu Ser Leu Pro Val Thr Leu
1               5                   10                  15

Gly Gln Pro Ala Ser Ile Ser Cys Arg Ser Ser Gln Ser Leu Val His
                20                  25                  30

Ser Asn Gly Asn Thr Tyr Leu Asn Trp Tyr Gln Gln Lys Pro Gly Gln
            35                  40                  45

Pro Pro Arg Leu Leu Ile Tyr Lys Ile Ser Asn Arg Phe Ser Gly Val
        50                  55                  60

Pro Asp Arg Phe Ser Gly Ser Gly Ala Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Thr His Glu Pro Tyr Thr
            100

<210> SEQ ID NO 86
<211> LENGTH: 103
<212> TYPE: PRT
<213> ORGANISM: Artificial Sequence -continued

```
<220> FEATURE:
<221> NAME/KEY: source
<223> OTHER INFORMATION: /note="Description of Artificial Sequence:
      Synthetic polypeptide"

<400> SEQUENCE: 86

Met Asp Ile Val Met Thr Gln Thr Pro Leu Ser Leu Pro Val Thr Leu
1               5                   10                  15

Gly Gln Pro Ala Ser Ile Ser Cys Arg Ser Ser Gln Ser Leu Val His
            20                  25                  30

Ser Asn Gly Asn Thr Tyr Leu Ser Trp Leu Gln Gln Arg Pro Gly Gln
        35                  40                  45

Pro Pro Arg Leu Leu Ile Tyr Lys Ile Ser Asn Arg Phe Ser Gly Val
    50                  55                  60

Pro Asp Arg Phe Ser Gly Ser Gly Ala Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Thr His Glu Pro Tyr Thr
            100
```

ANTI-TRKB ANTIBODIES

CROSS REFERENCE TO RELATED APPLICATIONS

This application is a 371 U.S. national phase application of international application number PCT/US2009/031345 filed 16 Jan. 2009, which claims priority to U.S. provisional patent application No. 61/021,820, filed 17 Jan. 2008. The full disclosure of these applications is incorporated herein by reference in its entirety and for all purposes.

FIELD OF THE INVENTION

The present invention relates to antibody and antigen binding molecule agonists of tyrosine receptor kinase B (TrkB).

BACKGROUND OF THE INVENTION

I. TrkB

Tyrosine receptor kinase B (TrkB) belongs to a family of single transmembrane receptor tyrosine kinases that includes TrkA and TrkC. These tyrosine receptor kinases (trks) mediate the activity of neurotrophins Neurotrophins are required for neuronal survival and development and regulate synaptic transmission via modulation of neuronal architecture and synaptic plasticity. Neurotrophins include, but are not limited to, nerve growth factor (NGF), brain derived neurotrophic factor (BDNF), neurotrophin-3 (NT-3), and neurotrophin-4/5 (NT-4/5). (Lo, K Y et al., *J. Biol. Chem.*, 280:41744-52 (2005)). TrkB is a high affinity receptor of BDNF (Minichiello, et al., *Neuron* 21:335-45 (1998)). Neurotrophin binding to trk activates the receptor which dimerizes and auto-phosphorylates specific tyrosine residues on the intracellular domain of the receptor (Jing, et al. *Neuron* 9:1067-1079 (1992); Barbacid, *J. Neurobiol.* 25:1386-1403 (1994); Bothwell, *Ann. Rev. Neurosci.* 18:223 253 (1995); Segal and Greenberg, *Ann. Rev. Neurosci.* 19:463 489 (1996); Kaplan and Miller, *Curr. Opinion Neurobiol.* 10:381 391 (2000)). These phospho-tyrosine residues serve as docking sites for elements of intracellular signaling cascades that lead to the suppression of neuron death and other effects of the neurotrophins For example, Shc, FRS-2, SH2B, rAPS and PLCγ interact with TrkB via phosphorylated tyrosine residues. Association of these adaptor molecules with activated TrkB results in the initiation of signaling pathways, including the mitogen-activated protein kinase, phosphatidylinositol 3-kinase, and PLCγ pathways, thereby mediating the actions of neurotrophins (Lo, K Y et al., *J. Biol. Chem.*, 280:41744-52 (2005)).

II. Diabetes

The concentration of glucose in the human bloodstream must be controlled within a relatively tight range (60-120 milligrams per deciliter of blood) to maintain normal health. If blood glucose drops too low, a condition known as hypoglycemia results, with symptoms such as faintness, weakness, headache, confusion and personality changes. Excessive blood glucose, or hyperglycemia, may cause tissue damage due to the chemical reactions between the excess glucose and proteins in cells, tissues, and organs. This damage is thought to cause the diabetic complications of blindness, kidney failure, impotence, atherosclerosis, and increased vulnerability to infection.

Diabetes mellitus is associated with continuous and pathologically elevated blood glucose concentration; it is one of the leading causes of death in the United States and is responsible for about 5% of all mortality. Diabetes is divided into two major sub-classes: Type I, also known as juvenile diabetes, or Insulin-Dependent Diabetes Mellitus (IDDM), and Type II, also known as adult onset diabetes, or Non-Insulin-Dependent Diabetes Mellitus (NIDDM).

The diagnosis of Type II diabetes mellitus includes assessment of symptoms and measurement of glucose in the urine and blood. Blood glucose level determination is necessary for an accurate diagnosis. More specifically, fasting blood glucose level determination is a standard approach used. However, the oral glucose tolerance test (OGTT) is considered to be more sensitive than fasted blood glucose level. Type II diabetes mellitus is associated with impaired oral glucose tolerance (OGT). The OGTT thus can aid in the diagnosis of Type II diabetes mellitus, although generally not necessary for the diagnosis of diabetes (Emancipator K, *Am J Clin Pathol* 1997 November; 112(5):665 74; Type 2 Diabetes Mellitus, Decision Resources Inc., March 2000).

Thus, impaired glucose tolerance is diagnosed in individuals that have fasting blood glucose levels less than those required for a diagnosis of Type II diabetes mellitus, but have a plasma glucose response during the OGTT between normal and diabetics Impaired glucose tolerance is considered a pre-diabetic condition, and impaired glucose tolerance (as defined by the OGTT) is a strong predictor for the development of Type II diabetes mellitus (Haffner S M, *Diabet Med* 1997 August; 14 Suppl 3:S12 8).

Type II diabetes mellitus is a progressive disease associated with the reduction of pancreatic function and/or other insulin-related processes, aggravated by increased plasma glucose levels. Thus, Type II diabetes mellitus usually has a prolonged prediabetic phase and various pathophysiological mechanisms can lead to pathological hyperglycemia and impaired glucose tolerance, for instance, abnormalities in glucose utilization and effectiveness, insulin action and/or insulin production in the prediabetic state (Goldberg R B, *Med Clin North Am* 1998 July; 82(4):805 21).

The prediabetic state associated with glucose intolerance can also be associated with a predisposition to abdominal obesity, insulin resistance, hyperlipidemia, and high blood pressure (Groop L, Forsblom C, Lehtovirta M, *Am J Hypertens* 1997 September; 10(9 Pt 2):172S 180S; Haffner S M, *J Diabetes Complications* 1997 March-April, 11(2):69 76; Beck-Nielsen H, Henriksen J E, Alford F, Hother-Nielson O, *Diabet Med* 1996 September; 13 (9 Suppl 6):578 84).

Early intervention in individuals at risk to develop Type II diabetes mellitus, focusing on reducing the pathological hyperglycemia or impaired glucose tolerance may prevent or delay the progression towards Type II diabetes mellitus and associated complications. Therefore, by effectively treating impaired oral glucose tolerance and/or elevated blood glucose levels, one can prevent or inhibit the progression of the disorder to Type II diabetes mellitus. See, e.g., U.S. Pat. No. 7,109,174.

Insulin and sulfonylureas (oral hypoglycemia therapeutic agents) are the two major classes of diabetes medicines prescribed today in the United States. Insulin is prescribed for both Type I and Type II diabetes, while sulfonylureas are usually prescribed for Type II diabetics only. Sulfonylureas stimulate natural insulin secretion and reduce insulin resistance; these compounds do not replace the function of insulin in metabolism. Approximately one-third of patients who receive sulfonylurea become resistant to it. Some Type II diabetics do not respond to sulonylurea therapy. Of patients who do respond to initial treatment with sulfonylureas, 5-10% are likely to experience a loss of sulfonylurea effectiveness after about ten years. See, e.g., U.S. Pat. No. 7,115,284.

Many anti-diabetic agents typically prescribed for the treatment of Type II diabetes mellitus, for example, sulfonylureas and thiazolidinediones, have an undesired side effect of increasing body weight. Increased body weight in patients with prediabetic conditions or with diagnosed Type II diabetes mellitus results in deleterious effects due to accentuation of the metabolic and endocrine dysregulation, and obesity per se is a pivotal risk factor for the development and progressive worsening of Type II diabetes mellitus. Thus it is desirable to have an anti-diabetic agent which maintains or lowers body weight. See, e.g., U.S. Pat. No. 7,199,174.

Obesity is a common and very serious public health problem as it increases a person's risk for a number of serious conditions, including diabetes, heart disease, stroke, high blood pressure, and some types of cancers. Considerable increase in the number of obese individuals over the past two decades has created profound public health implications. Although studies have demonstrated that reduction in obesity by diet and exercise reduces the associated risk factors dramatically, these treatments are largely unsuccessful considering obesity is strongly associated with genetically inherited factors that contribute to increased appetite, preferences for highly caloric foods, reduced physical activity, and increased lipogenic metabolism. See, e.g., U.S. Pat. No. 7,115,767.

III. Rett Syndrome

First identified by Dr. Andreas Rett in 1966, Rett Syndrome (RTT) is a devastating CNS disorder that originates from late-neurodevelopmental defects. It almost exclusively affects young girls of all ethnicities at a rate of 1/10,000-15,000 live births. Some individuals with RTT die at a young age; many, however, can live into adulthood and are profoundly disabled. Up to 25% of patients die of cardiac/respiratory failures. There is so far no effective treatment for the disease.

Following a period of apparent normal development, affected girls develop RTT symptoms at the age of 6-18 months, which progressively worsen over the next few years. Symptoms include normal head circumference at birth followed by deceleration of head growth; loss of acquired speech, communication dysfunction, cognitive impairment; purposeful hand skills replaced by stereotypical hand movements (tortuous hand wringing, hand washing, clapping, patting, etc.); impaired or deteriorating locomotion (gait ataxia, stiffness, etc.); breathing difficulties while awake; impaired sleeping pattern from early infancy; abnormal muscle tone accompanied by muscle wasting and dystonia; peripheral vasomotor disturbances; progressive scoliosis or kyphosis; and growth retardation.

The disorder is also characterized by central autonomic dysfunctions, and Rett patients exhibit some or all of the following symptoms: multiple respiratory dysrhythmias consisting of periods of breath holding, shallow breathing, hyperventilation, prolonged apneas; cardiac arrhythmias with reduction in baseline cardiac vagal tone; and cardiac sensitivity to baroreflex. These symptoms are life-threatening and render Rett patients at risk of sudden death. They indicate brainstem immaturity and a lack of integrative inhibition within the cardiorespiratory network and from the hypothalamus or limbic cortex during wakefulness. Furthermore, alteration in brain stem neurotrophin signaling (NGF and BDNF) is reported in Rett patients, as is reduction in monoamine (serotonin, norepinephrine) and neuropeptide (Substance P) levels.

RTT is a monogenic disease, caused in the vast majority of cases by mutations in the X chromosome-linked gene mecp2, which encodes the transcriptional repressor MeCP2 (methyl-CpG cytosine binding protein 2). MeCP2 binds preferentially to methylated DNA.

The neurotrophin factor BDNF is a known direct target of MeCP2, and is an important trophic factor for norepinephrine and serotonin neurons. Surprisingly, Mecp2-KO mice are deficient in brain BDNF, and a genetic overexpression of brain BDNF can increase their lifespan and rescue some of their locomotor defects. BDNF deficiency disorders identified in humans include Rett Syndrome, Wilms' tumor, aniridia, genitourinary anomalies and mental retardation (WAGR) syndrome (Han, et al., N Engl J Med (2008) 359(9):918-27), obesity resulting from melanocortin receptor MC4R deficiency (Farooqi and O'Rahilly, Endocrine Rev (2006) 27(7): 710-18), cachexia/muscle wasting syndromes (Lin, et al., PloS, 3(4):e1900; WO 2007/088476).

BRIEF SUMMARY OF THE INVENTION

In one aspect, the present invention provides antibodies that bind tyrosine receptor kinase B (TrkB). In some embodiments, the antibodies comprise:

(a) a heavy chain variable region comprising a human heavy chain V-segment, a heavy chain complementary determining region 3 (CDR3), and a heavy chain framework region 4 (FR4), and (b) a light chain variable region comprising a human light chain V segment, a light chain CDR3, and a light chain FR4, wherein i) the heavy chain CDR3 comprises the amino acid sequence V(T/V)(S/T/R/N)WFAY (SEQ ID NO:34); and ii) the light chain CDR3 variable region comprises the amino acid sequence (S/M)QGT(H/A)(E/V/I)PYT (SEQ ID NO:42); and wherein the antibody is a TrkB agonist.

In another aspect, the present invention provides antibodies that specifically bind TrkB. In some embodiments, the antibodies comprise a heavy chain variable region and a light chain variable region, wherein the heavy chain variable region and the light chain variable region each comprise the following three complementary determining regions (CDRs): CDR1, CDR2 and CDR3; wherein:

i) the CDR1 of the heavy chain variable region comprises an amino acid sequence of SEQ ID NO:25;

ii) the CDR2 of the heavy chain variable region comprises an amino acid sequence selected from the group consisting of SEQ ID NO:28, SEQ ID NO:29 and SEQ ID NO:30;

iii) the CDR3 of the heavy chain variable region comprises an amino acid sequence selected from the group consisting of SEQ ID NO:32 and SEQ ID NO:33;

iv) the CDR1 of the light chain variable region comprises an amino acid sequence selected from the group consisting of SEQ ID NO:35, SEQ ID NO:36 and SEQ ID NO:37;

v) the CDR2 of the light chain variable region comprises an amino acid sequence of SEQ ID NO:39;

vi) the CDR3 of the light chain variable region comprises an amino acid sequence selected from the group consisting of SEQ ID NO:40 and SEQ ID NO:41.

With respect to the embodiments of the antibodies, in some embodiments, the heavy chain V-segment shares at least 90% sequence identity to SEQ ID NO:16, and wherein the light chain V segment shares at least 90% sequence identity to SEQ ID NO:24.

In some embodiments, the heavy chain V-segment shares at least 90% sequence identity to an amino acid selected from the group consisting of SEQ ID NO:12, SEQ ID NO:13, SEQ ID NO:14 and SEQ ID NO:15, and the light chain V segment shares at least 90% sequence identity to an amino acid selected from the group consisting of SEQ ID NO:17, SEQ ID NO:18, SEQ ID NO:19, SEQ ID NO:20, SEQ ID NO:21, SEQ ID NO:22 and SEQ ID NO:23.

In some embodiments, the heavy chain CDR3 comprises an amino acid sequence selected from the group consisting of SEQ ID NO:32 and SEQ ID NO:33; and the light chain CDR3 comprises an amino acid sequence selected from the group consisting of SEQ ID NO:40 and SEQ ID NO:41.

In some embodiments, the heavy chain FR4 is a human germline FR4. In some embodiments, the heavy chain FR4 is SEQ ID NO:50. In some embodiments, the heavy chain J-segment comprises the human germline JH4 partial sequence WGQGTLVTVSS (SEQ ID NO:50).

In some embodiments, the light chain FR4 is a human germline FR4. In some embodiments, the light chain FR4 is the human germline J1(2 partial sequence FGQGKLEIK (SEQ ID NO:61).

In some embodiments, the heavy chain V-segment and the light chain V-segment each comprise a complementary determining region 1 (CDR1) and a complementary determining region 2 (CDR2); wherein:
 i) the CDR1 of the heavy chain V-segment comprises an amino acid sequence of SEQ ID NO:27;
 ii) the CDR2 of the heavy chain V-segment comprises an amino acid sequence of SEQ ID NO:31;
 iii) the CDR1 of the light chain V-segment comprises an amino acid sequence of SEQ ID NO:38; and
 iv) the CDR2 of the light chain V-segment comprises an amino acid sequence of SEQ ID NO:39.

In some embodiments,
 i) the CDR1 of the heavy chain V-segment comprises SEQ ID NO:25;
 ii) the CDR2 of the heavy chain V-segment comprises SEQ ID NO:28;
 iii) the heavy chain CDR3 comprises SEQ ID NO:32;
 iv) the CDR1 of the light chain V-segment comprises SEQ ID NO:35;
 v) the CDR2 of the light chain V-segment comprises SEQ ID NO:38; and
 vi) the light chain CDR3 comprises SEQ ID NO:41.

In some embodiments,
 i) the CDR1 of the heavy chain V-segment comprises SEQ ID NO:25;
 ii) the CDR2 of the heavy chain V-segment comprises SEQ ID NO:28;
 iii) the heavy chain CDR3 comprises SEQ ID NO:32;
 iv) the CDR1 of the light chain V-segment comprises SEQ ID NO:36;
 v) the CDR2 of the light chain V-segment comprises SEQ ID NO:38; and
 vi) the light chain CDR3 comprises SEQ ID NO:40.

In some embodiments,
 i) the CDR1 of the heavy chain V-segment comprises SEQ ID NO:25;
 ii) the CDR2 of the heavy chain V-segment comprises SEQ ID NO:28;
 iii) the heavy chain CDR3 comprises SEQ ID NO:32;
 iv) the CDR1 of the light chain V-segment comprises SEQ ID NO:37;
 v) the CDR2 of the light chain V-segment comprises SEQ ID NO:38; and
 vi) the light chain CDR3 comprises SEQ ID NO:40.

In some embodiments,
 i) the CDR1 of the heavy chain V-segment comprises SEQ ID NO:25;
 ii) the CDR2 of the heavy chain V-segment comprises SEQ ID NO:29;
 iii) the heavy chain CDR3 comprises SEQ ID NO:32;
 iv) the CDR1 of the light chain V-segment comprises SEQ ID NO:35;
 v) the CDR2 of the light chain V-segment comprises SEQ ID NO:38; and
 vi) the light chain CDR3 comprises SEQ ID NO:41.

In some embodiments, the heavy chain variable region shares at least 90% amino acid sequence identity to the variable region of SEQ ID NO:4 and the light chain variable region shares at least 90% amino acid sequence identity to the variable region of SEQ ID NO:11.

In some embodiments, the heavy chain variable region shares at least 90% amino acid sequence identity to the variable region selected from the group consisting of SEQ ID NO:1, SEQ ID NO:2 and SEQ ID NO:3 and the light chain variable region shares at least 90% amino acid sequence identity to the variable region selected from the group consisting of SEQ ID NO:5, SEQ ID NO:6, SEQ ID NO:7, SEQ ID NO:8, SEQ ID NO:9 and SEQ ID NO:10.

In some embodiments, the heavy chain variable region shares at least 95% amino acid sequence identity to the variable region selected from the group consisting of SEQ ID NO:1, SEQ ID NO:2 and SEQ ID NO:3 and the light chain variable region shares at least 95% amino acid sequence identity to the variable region selected from the group consisting of SEQ ID NO:5, SEQ ID NO:6, SEQ ID NO:7, SEQ ID NO:8, SEQ ID NO:9 and SEQ ID NO:10.

In some embodiments, the heavy chain variable region comprises an amino acid sequence selected from the group consisting of SEQ ID NO:1, SEQ ID NO:2 and SEQ ID NO:3 and the light chain variable region comprises an amino acid sequence selected from the group consisting of SEQ ID NO:5, SEQ ID NO:6, SEQ ID NO:7, SEQ ID NO:8, SEQ ID NO:9 and SEQ ID NO:10.

In some embodiments, the antibody binds to TrkB with an equilibrium dissociation constant (KD) of less than $5 \times 10^{-8}$ M.

In some embodiments, the antibody is a FAb' fragment. In some embodiments, the antibody is an IgG. In some embodiments, the antibody is a single chain antibody (scFv). In some embodiments, the antibody comprises human constant regions.

In some embodiments, the antibody does not bind to Tyrosine Kinase Receptor A or Tyrosine Kinase Receptor C. In some embodiments, the antibody binds to the Ligand Binding Domain (LBD) of TrkB. In some embodiments, the antibody competes with the binding of Brain Derived Neurotrophic Factor (BDNF) to TrkB.

In some embodiments, the antibody comprises a heavy chain comprising SEQ ID NO:1 and a light chain comprising SEQ ID NO:8.

In some embodiments, the antibody comprises a heavy chain comprising SEQ ID NO:1 and a light chain comprising SEQ ID NO:9.

In some embodiments, the antibody comprises a heavy chain comprising SEQ ID NO:1 and a light chain comprising SEQ ID NO:10.

In some embodiments, the antibody comprises a heavy chain comprising SEQ ID NO:3 and a light chain comprising SEQ ID NO:8.

In a further aspect, the invention provides a pharmaceutically acceptable composition comprising an antibody of the invention and a physiologically compatible excipient. Embodiments of the pharmaceutically acceptable compositions are as described above for the antibodies.

In some embodiments, the pharmaceutical composition further comprises an agent for use in reducing or inhibiting respiratory distress, e.g., an activator of the norepinephrine and/or serotonin pathways. The second agent can be a tricyclic antidepressant, e.g., desipramine (DMI). In some embodiments, the second agent is a serotonin 1A receptor partial agonist, e.g., buspirone, Fluoxetine and Reboxetine. In some embodiments, the second agent is an activator of glutamatergic AMPA receptors, e.g., AMPAkine CX54. In some embodiments, the second agent is a prostaglandin, a progesterone, or a potentiator of TrkB activity (e.g., protein tyrosine phosphatase inhibitors).

In some embodiments, the pharmaceutical composition further comprises an agent that reduces blood glucose levels in an individual. In some embodiments, the pharmaceutical composition further comprises an agent that reduces body weight in an individual.

In a related aspect, the invention provides methods of treating, reducing, inhibiting, ameliorating and/or preventing a disorder resulting from a BDNF insufficiency in an individual in need thereof by administering an antibody of the invention to the individual. Embodiments of the methods of treatment are as described above and herein for the antibodies. In some embodiments, the antibody is administered systemically or peripherally, e.g., orally, inhalationally, intravenously, or intraperitoneally. In some embodiments, the disorder resulting from a BDNF insufficiency is selected from the group consisting of Rett Syndrome, WAGR Syndrome, obesity resulting MC4R deficiency, and cachexia (e.g., due to cancer, aging, eating disorders or drugs, including opioid-induced emesis).

In a further aspect, the invention provides methods of reducing blood glucose levels and/or body weight in an individual in need thereof, the method comprising administering a therapeutically effective amount of an antibody of the invention to the individual. Embodiments of the methods of treatment are as described above and herein for the antibodies. With respect to further embodiments of the methods, in some embodiments, the individual is pre-diabetic. In some embodiments, the individual has type I diabetes. In some embodiments, the individual has type II diabetes. In some embodiments, the individual is overweight. In some embodiments, the individual is obese.

In some embodiments, the methods further comprise the step of administering a therapeutically effective amount of a second agent effective in reducing blood glucose to the individual. In some embodiments, the second agent is selected from the group consisting of: insulin, sulfonylureas, insulinotropic agents, metformin, PPARγ agonists PPARα agonists, PPARδ agonists, PPARα/γ dual agonists, PPARα/γ/δ pan agonists, alpha-glucosidase inhibitors, DPP-IV inhibitors, and GLP-1/GLP-1 analogs.

In some embodiments, the methods further comprise the step of administering a therapeutically effective amount of a second agent effective in reducing weight or obesity is administered to the individual. In some embodiments, the second agent is selected from the group consisting of lipase inhibitors, sibutramine, CB-1 inhibitors, topiramate, amylin, amylin analogs, leptin, PYY/PYY analogs, and GLP-1/GLP-1 analogs.

In some embodiments, the second agent and the antibody are administered as a mixture. In some embodiments, the second agent and the antibody are administered separately.

DEFINITIONS

An "antibody" refers to a polypeptide of the immunoglobulin family or a polypeptide comprising fragments of an immunoglobulin that is capable of noncovalently, reversibly, and in a specific manner binding a corresponding antigen. An exemplary antibody structural unit comprises a tetramer. Each tetramer is composed of two identical pairs of polypeptide chains, each pair having one "light" (about 25 kD) and one "heavy" chain (about 50-70 kD), connected through a disulfide bond. The recognized immunoglobulin genes include the κ, λ, α, γ, δ, ε, and μ constant region genes, as well as the myriad immunoglobulin variable region genes. Light chains are classified as either κ or λ. Heavy chains are classified as γ, μ, α, δ, or ε, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain ($V_L$) and variable heavy chain ($V_H$) refer to these regions of light and heavy chains respectively. As used in this application, an "antibody" encompasses all variations of antibody and fragments thereof that possess a particular binding specifically, e.g., for TrkB. Thus, within the scope of this concept are full length antibodies, chimeric antibodies, single chain antibodies (ScFv), Fab, Fab', and multimeric versions of these fragments (e.g., $F(ab')_2$) with the same binding specificity.

"Complementarity-determining domains" or "complementary-determining regions" ("CDRs") interchangeably refer to the hypervariable regions of $V_L$ and $V_H$. The CDRs are the target protein-binding site of the antibody chains that harbors specificity for such target protein. There are three CDRs (CDR1-3, numbered sequentially from the N-terminus) in each human $V_L$ or $V_H$, constituting about 15-20% of the variable domains. The CDRs are structurally complementary to the epitope of the target protein and are thus directly responsible for the binding specificity. The remaining stretches of the $V_L$ or $V_H$, the so-called framework regions, exhibit less variation in amino acid sequence (Kuby, Immunology, 4th ed., Chapter 4. W.H. Freeman & Co., New York, 2000).

The positions of the CDRs and framework regions are determined using various well known definitions in the art, e.g., Kabat, Chothia, international ImMunoGeneTics database (IMGT) (on the worldwide web at imgt.cines.fr/), and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

The term "binding specificity determinant" or "BSD" interchangeably refer to the minimum contiguous or non-contiguous amino acid sequence within a complementary determining region necessary for determining the binding specificity of an antibody. A minimum binding specificity determinant can be within one or more CDR sequences. In some embodiments, the minimum binding specificity determinants reside within (i.e., are determined solely by) a portion or the full-length of the CDR3 sequences of the heavy and light chains of the antibody.

An "antibody light chain" or an "antibody heavy chain" as used herein refers to a polypeptide comprising the $V_L$ or $V_H$, respectively. The endogenous $V_L$ is encoded by the gene segments V (variable) and J (junctional), and the endogenous $V_H$ by V, D (diversity), and J. Each of $V_L$ or $V_H$ includes the CDRs as well as the framework regions. In this application, antibody light chains and/or antibody heavy chains may, from time to time, be collectively referred to as "antibody chains." These terms encompass antibody chains containing mutations that do not disrupt the basic structure of $V_L$ or $V_H$, as one skilled in the art will readily recognize.

Antibodies exist as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab' which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. Paul, *Fundamental Immunology* 3d ed. (1993). While various antibody fragments are defined in terms of the digestion of an intact antibody, one of skill will appreciate that such fragments may be synthesized de novo either chemically or by using recombinant DNA methodology. Thus, the term "antibody," as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4:72 (1983); Cole et al., Monoclonal Antibodies and Cancer Therapy, pp. 77-96. Alan R. Liss, Inc. 1985). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., supra; Marks et al., *Biotechnology*, 10:779-783, (1992)).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some complementary determining region ("CDR") residues and possibly some framework ("FR") residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, and drug; or (b) the variable region, or a portion thereof, is altered, replaced or exchanged with a variable region having a different or altered antigen specificity.

The term "variable region" or "V-region" interchangeably refer to a heavy or light chain comprising FR1-CDR1-FR2-CDR2-FR3-CDR3-FR4. See, FIG. 1. An endogenous variable region is encoded by immunoglobulin heavy chain V-D-J genes or light chain V-J genes. A V-region can be naturally occurring, recombinant or synthetic.

As used herein, the term "variable segment" or "V-segment" interchangeably refer to a subsequence of the variable region including FR1-CDR1-FR2-CDR2-FR3. See, FIG. 1. An endogenous V-segment is encoded by an immunoglobulin V-gene. A V-segment can be naturally occurring, recombinant or synthetic.

As used herein, the term "J-segment" refers to a subsequence of the variable region encoded comprising a C-terminal portion of a CDR3 and the FR4. An endogenous J-segment is encoded by an immunoglobulin J-gene. See, FIG. 1. A J-segment can be naturally occurring, recombinant or synthetic.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., *Proc. Natl. Acad. Sci. USA*, 81:6851-6855 (1984); Morrison and Oi, Adv. Immunol., 44:65-92 (1988); Verhoeyen et al., *Science*, 239:1534-1536 (1988); Padlan, *Molec. Immun.*, 28:489-498 (1991); Padlan, *Molec. Immun.*, 31(3):169-217 (1994).

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other evaluated variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementary determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 92%, 94%, 96%, 98%, 99% sequence identity with the reference variable region nucleic acid or amino acid sequence. Corresponding human germline sequences can be determined, for example, through the publicly available international ImMunoGeneTics database (IMGT) (on the worldwide web at imgt.cines.fr/) and V-base (on the worldwide web at vbase.mrc-cpe.cam.ac.uk).

The phrase "specifically (or selectively) bind," when used in the context of describing the interaction between an antigen, e.g., a protein, to an antibody or antibody-derived binding agent, refers to a binding reaction that is determinative of the presence of the antigen in a heterogeneous population of proteins and other biologics. Thus, under designated immunoassay conditions, the antibodies or binding agents with a particular binding specificity bind to a particular antigen at least two times the background and do not substantially bind in a significant amount to other antigens present in the sample. Specific binding to an antibody or binding agent under such conditions may require the antibody or agent to have been selected for its specificity for a particular protein. This selection may be achieved by subtracting out antibodies that cross-react with, e.g., TrkB molecules from other species (e.g., mouse) or other Trk subtypes (e.g., TrkA, TrkC, etc.). A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

The term "equilibrium dissociation constant ($K_D$, M)" refers to the dissociation rate constant ($k_d$, time$^{-1}$) divided by the association rate constant ($k_a$, time$^{-1}$, M$^{-1}$). Equilibrium dissociation constants can be measured using any known method in the art. The antibodies of the present invention generally will have an equilibrium dissociation constant of less than about $10^{-7}$ or $10^{-8}$ M, for example, less than about $10^{-9}$ M or $10^{-10}$ M, in some embodiments, less than about $10^{-11}$ M, $10^{-12}$ M or $10^{-13}$ M.

As used herein, the term "antigen-binding region" refers to a domain of the TrkB-binding molecule of this invention that is responsible for the specific binding between the molecule and TrkB. An antigen-binding region includes at least one antibody heavy chain variable region and at least one antibody light chain variable region. There are at least one such antigen-binding regions present in each TrkB-binding molecule of this invention, and each of the antigen-binding regions may be identical or different from the others. In some embodiments, at least one of the antigen-binding regions of a TrkB-binding molecule of this invention acts as an agonist of TrkB.

The term "antibody agonist" or "agonist" interchangeably refer to an antibody capable of activating a receptor to induce a full or partial (e.g. 9 at least 60%) receptor-mediated response. For example, an agonist of TrkB binds to TrkB and induces TrkB-mediated signaling. In some embodiments, a TrkB antibody agonist can be identified by its ability to bind TrkB and induce neurite outgrowth when contacted to SH-SY5Y cells or as otherwise described herein. In other embodiments, a TrkB antibody agonist can be identified by its ability to rescue cells from detachment-dependent apoptosis as measured in an anoikis assay, described herein. An anti-TrkB antibody with an EC50 of less than 5 nM, for example, less than 1 nM, 500 pM, 250 pM, 100 pM, 50 pM or 30 pM, in an anoikis assay as described herein, is considered a TrkB antibody agonist.

The term "TrkB" or "tyrosine receptor kinase B" interchangeably refer to one of the three members of the tropomyosin-related kinase (Trk) family of receptor tyrosine kinases, the other members being TrkA and TrkC. TrkB is a member of the neurotrophic tyrosine receptor kinase (NTRK) family, and is also known as neurotrophic tyrosine kinase receptor, type 2 (NTRK2). TrkB is a membrane-bound receptor that, upon neurotrophin binding, phosphorylates itself and members of the MAPK pathway. Ligand for TrkB include brain-derived neurotrophic factor (BDNF) and neurotrophin-3. See, e.g., Haniu, et al., *Arch Biochem Biophys* (1995) 322(1):256-264; Squinto, et al., *Cell* (1991) 65(5) 885-893; and Soppet, et al., *Cell* (1991) 65(5) 895-903. Signalling through TrkB leads to cell differentiation. Mutations in this gene have been associated with obesity and mood disorders. Alternate transcriptional splice variants encoding different isoforms of TrkB exist. The nucleic acid and amino acid sequences of TrkB are known, and have been published in GenBank Accession No. NM_001018064 (gi:65506744, PRI Nov. 18, 2007). See also, GenBank Accession Nos. BC075804.1, U12140.1, BC031835.1 and AF410899.1. As used herein, a TrkB polypeptide is functionally a tyrosine kinase receptor that is activated by binding of BDNF or neurotrophin-3 and elicits intracellular signaling by phosphorylating itself and members of the MAPK pathway. Structurally, a TrkB amino acid sequence shares at least about 90%, 91%, 92%, 93%, 94%, 95%, 96%, 97%, 98%, 99% or 100% sequence identity with the amino acid sequence of GenBank accession numbers NP_001018074.1, AAB33109, AAL67968, AAL67964, AAC51371.1, AAH31835.1 or AAL67965.1. Structurally, a TrkB nucleic acid sequence shares at least about 90%, 91%, 92%, 93%, 94%, 95%, 96%, 97%, 98%, 99% or 100% sequence identity with the nucleic acid sequence of GenBank accession numbers NM_001018064, 576473, BC075804.1, U12140.1, BC031835.1 or AF410899.1.

"Activity" of a polypeptide of the invention refers to structural, regulatory, or biochemical functions of a polypeptide in its native cell or tissue. Examples of activity of a polypeptide include both direct activities and indirect activities. Exemplary direct activities are the result of direct interaction with the polypeptide, including ligand binding, such as binding of BDNF to the Ligand Binding Domain (LBD) (see, e.g., Naylor et al., *Biochem Biophys Res Commun.* 291(3):501-7 (2002)) of TrkB, production or depletion of second messengers (e.g., cAMP, cGMP, IP$_3$, DAG, or Ca$^{2+}$), ion flux, and changes in the level of phosphorylation or transcription. Exemplary indirect activities in the context of TrkB are observed as a change in phenotype or response in a cell or tissue to a polypeptide's directed activity, e.g., reducing overall blood glucose levels as a result of the interaction of the polypeptide with other cellular or tissue components.

The term "obese," when used in reference to adult humans, refers to an individual with a body mass index (BMI) of 30 or more. "Overweight," when used in reference to adult humans, refers to an individual with a BMI of 25 or more. For children, the charts of Body-Mass-Index for Age are used, where a BMI greater than the 85$^{th}$ percentile is considered "overweight" and a BMI greater than the 95$^{th}$ percentile is considered "obese". See, e.g., *Clinical Guidelines on the Identification, Evaluation, and Treatment of Overweight and Obesity in Adult* (National Heart, Lung and Blood Institute, Jun. 17, 1998) and *Preventing and Managing the Global Epidemic of Obesity* in Report of the World Health Organization Consultation of Obesity (WHO, Geneva, June 1997).

A "pre-diabetic individual" refers to an adult with a fasting blood glucose level greater than 110 mg/dl but less than 126 mg/dl or a 2 hour PG reading of greater than 140 mg/dl but less than 200 mg/dl. A "diabetic individual," when used to compare with a sample from a patient, refers to an adult with a fasting blood glucose level greater than 126 mg/dl or a 2 hour PG reading of greater than 200 mg/dl. "Fasting" refers to no caloric intake for at least 8 hours. A "2 hour PG" refers to the level of blood glucose after challenging a patient to a glucose load containing the equivalent of 75 g anhydrous glucose dissolved in water. The overall test is generally referred to as an oral glucose tolerance test (OGTT). See, e.g., *Diabetes Care,* 2003, 26(11): 3160-3167 (2003).

The term "isolated," when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., 70%, 75%, 80%, 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. The invention provides polypeptides or polynucleotides that are substantially identical to the polypeptides or polynucleotides, respectively, exemplified herein (e.g., the variable regions exemplified in any one of SEQ ID NOs: 1-11; the variable segments exemplified in any one of SEQ ID NOs: 12-24; the CDRs exemplified in any one of SEQ ID NOs: 25-42; the FRs exemplified in any one of SEQ ID NOs: 43-61; and the nucleic acid sequences exemplified in any on of SEQ ID NOs; 62-73). Optionally, the identity exists over a region that is at least about 15, 25 or 50 nucleotides in length, or more preferably over a region that is 100 to 500 or 1000 or more nucleotides in length, or over the full length of the reference sequence. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, substantial identity exists when one or two amino acid residues are conservatively substituted, according to the conservative substitutions defined herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "link," when used in the context of describing how the antigen-binding regions are connected within a TrkB-binding molecule of this invention, encompasses all possible means for physically joining the regions. The multitude of antigen-binding regions are frequently joined by chemical bonds such as a covalent bond (e.g., a peptide bond or a disulfide bond) or a non-covalent bond, which can be either a direct bond (i.e., without a linker between two antigen-binding regions) or indirect bond (i.e., with the aid of at least one linker molecule between two or more antigen-binding regions).

The terms "subject," "patient," and "individual" interchangeably refer to a mammal, for example, a human or a non-human primate mammal. The mammal can also be a laboratory mammal, e.g., mouse, rat, rabbit, hamster. In some embodiments, the mammal can be an agricultural mammal (e.g., equine, ovine, bovine, porcine, camelid) or domestic mammal (e.g., canine, feline).

The term "therapeutically acceptable amount" or "therapeutically effective dose" interchangeably refer to an amount sufficient to effect the desired result (i.e., apoptosis of a target cell). In some embodiments, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of a TrkB agonizing antibody of the invention can prevent the onset of, or result in a decrease in severity of, respectively, disease symptoms (e.g., symptoms of disorders associated with aberrantly low levels of TrkB signalling, e.g., due to deficiency of TrkB ligands including BDNF). Said terms can also promote or increase, respectively, frequency and duration of periods free from disease symptoms. A "prophylactically effective dosage," and a "therapeutically effective dosage," can also prevent or ameliorate, respectively, impairment or disability due to the disorders and diseases resulting from inadequate activation of TrkB.

As used herein, the term "respiratory disorders" includes but is not limited to, atelectasis, cystic fibrosis, Rett syndrome (RTT), asthma, apneas (e.g., sleep apnea), acute respiratory distress syndrome (ARDS), chronic obstructive pulmonary disease (COPD), emphysema, acute dyspnea, tachypnea, orthopnea, rheumatoid lung disease, pulmonary congestion or edema, chronic obstructive airway disease (e.g., emphysema, chronic bronchitis, bronchial asthma, and bronchiectasis), hypoventilation, Pickwickian Syndrome, obesity-hypoventilation syndrome, sudden infant death syndrome (SIDS), and hypercapnea. Furthermore, "respiratory disorders" also include conditions in humans known to be linked to genetic defects, such as Charcot-Marie-Tooth disease, Cheyne-Stokes breathing disorder, Willi-Prader syndrome, sudden infant death syndrome, congenital central hypoventilation, diffuse interstitial diseases (e.g., sarcoidosis, pneumoconiosis, hypersensitivity pneumonitis, bronchiolitis, Goodpasture's syndrome, idiopathic pulmonary fibrosis, idiopathic pulmonary hemosiderosis, pulmonary alveolar proteinosis, desquamative interstitial pneumonitis, chronic interstitial pneumonia, fibrosing alveolitis, hamman-rich syndrome, pulmonary eosinophilia, diffuse interstitial fibrosis, Wegener's granulomatosis, lymphomatoid granulomatosis, and lipid pneumonia), or tumors (e.g., bronchogenic carcinoma, bronchiolovlveolar carcinoma, bronchial carcinoid, hamartoma, and mesenchymal tumors).

BRIEF DESCRIPTION OF THE DRAWINGS

FIG. 5 illustrates aligned variable region amino acid sequences (FR1 through CDR3) of Fab clones TR134-4 (SEQ ID NOS:76 and 80), TR135-8 (SEQ ID NOS:76 and 81), TR139-2 (SEQ ID NOS:76 and 82), TR151-1 (SEQ ID NOS: 77 and 82) and TR144-1 (SEQ ID NOS:78 and 81) and comparison with the closest single human variable region translations of germline Vhf-02 (SEQ ID NO:15) or VkII A23 (SEQ ID NO:79). The FR4 (not shown) for all Fab Vh-regions is from human germ-line JH4 and has the sequence WGQGTLVTVSS (SEQ ID NO:50). The FR4 (not shown) for all Fab Vk-regions is from human germ-line Jk2 and has the sequence FGQGKLEIK (SEQ ID NO:61). CDRs are boxed and residues that differ from the corresponding position in the germline sequence (excluding the CDR3 "BSD" sequence) are in bold. Affinity maturation changes to the CDR3s are underlined and the germ-line replacement residue in the Vk CDR3 is italicized.

FIG. 6 illustrates aligned variable region amino acid sequences (FR1 through CDR3) of IgG clones TR127-2 (SEQ ID NO:76), TR143-3 (SEQ ID NO:78), TR154-2 (SEQ ID NO:77), TR119-1 (SEQ ID NO:84), TR129-1 (SEQ ID NO:85) and TR137-1 (SEQ ID NO:86) and comparison with the closest single human variable region translations of germline, Vh1-02 (SEQ ID NO:15) or VkII A23 (SEQ ID NO:83). The FR4 (not shown) for all IgG Vh-regions is from human germ-line JH4 and has the sequence WGQGTLVTVSS (SEQ ID NO:50). The FR4 (not shown) for all IgG Vk-regions is from human germ-line Jk2 and has the sequence FGQGKLEIK (SEQ ID NO:61). CDRs are boxed and residues that differ from the corresponding position in the germline sequence (excluding the CDR3 "BSD" sequence) are in bold. Affinity maturation changes to the CDR3s are underlined and the germ-line replacement residue in the Vk CDR3 is italicized.

FIG. 7 illustrates that binding of Fab with human V-segments is blocked by increasing concentrations of A10F18.2 IgG in an ELISA assay.

FIG. 8A-D illustrate binding of NVP-LFD253 (A), NVP-LFD254 (B), NVP-LFC325 (C) or NVP-LFC327 (D) to the human Fc-TrkB.

FIG. 9A-D illustrate ELISA assays showing specific binding of NVP-LFD253, NVP-LFD254, NVP-LFC325 and NVP-LFC327 to human TrkB-Fc fusion protein but not to human TrkB-Fc or TrkC-Fc fusion proteins. Purified IgG at 2 µg/ml was evaluated for specificity by examining its interaction with three different Trk family members (TrkA, TrkB and TrkC). Secondary Ab are replicates that were blocked and treated with only the goat-anti-human Fab-HRP detection Ab.

FIG. 10A-D illustrate evaluation of NVP-LFD253, NVP-LFD254, NVP-LFC325 and NVP-LFC327 for agonist activity in an anoikis assay. Purified IgG were evaluated on RIE-TrkB cells for 48 h. (−) are cells that were not treated with antibody.

FIG. 11A-D illustrate representative Biacore kinetic traces for IgG antibodies NVP-LFD253, NVP-LFD254, NVP-LFC325 and NVP-LFC327. Fc-TrkB was immobilized to the Biacore chip surface. A serial dilution of IgG was flowed over the chip at 30 µL/min The association phase was 300 seconds, followed by the dissociation phase in free buffer flow for 1200 seconds.

DETAILED DESCRIPTION

1. Introduction

Figure 1:
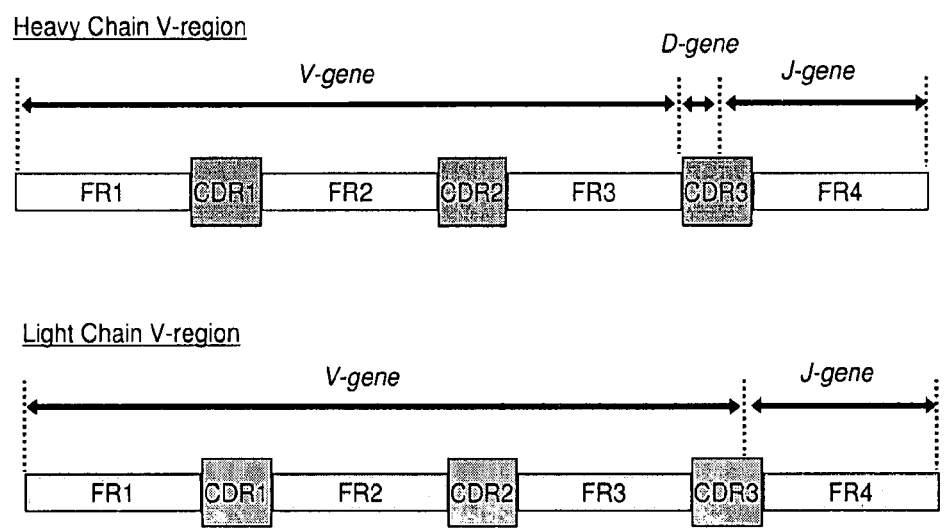
FIG. 1 illustrates a schematic depiction of the structural units that comprise the V-regions of an antibody. The heavy chain is encoded by three gene families (Heavy-V, D and J) and the light chain is encoded by two gene families (Kappa or Lambda V and J). The recombination of these genes results in the intact V-region. The CDR3 sequences are at the recombination sites of the heavy V, D and J genes, in the case of the heavy chain, and the kappa or lambda V and J genes in the case of the light chain.
Figure 2:
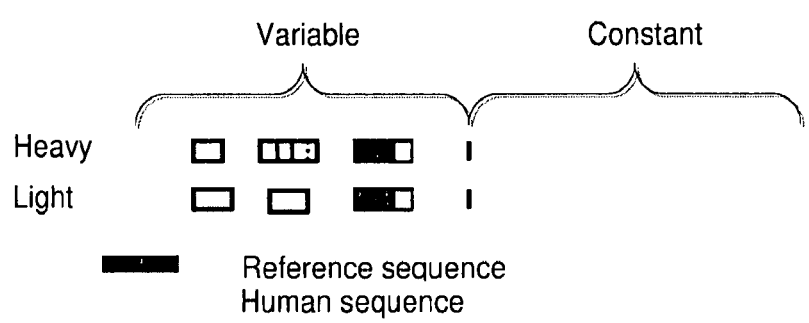
FIG. 2 illustrates a schematic of the replacement of reference antibody amino acid sequence with human amino acid sequence.

The present invention provides improved TrkB agonist antibodies. The improved TrkB agonist antibodies of the invention bind specifically to TrkB and activate TrkB. The TrkB agonist antibodies of the invention find use in reducing, inhibiting and preventing symptoms of disorders and diseases resulting from TrkB agonist ligand deficiency, e.g., BDNF deficiency. Exemplary diseases treatable using the anti-TrkB agonist antibodies of the invention include Rett Syndrome, WAGR Syndrome, obesity resulting from MC4R mutations and cachexia/wasting syndromes (e.g., due to cancer, aging, eating disorders or drugs). The anti-TrkB agonist antibodies also find use in reducing blood glucose levels in a subject in need thereof. Further, the TrkB agonist antibodies of the invention find use in preventing weight gain. TrkB activation is useful in preventing hyperglycemia and its associated conditions, obesity, pre-diabetes, and type-II diabetes.

2. Improved Anti-TrkB Antibodies Generally

The antibodies of the present invention specifically bind to tropomyosin-related kinase (Trk) receptor tyrosine kinase B (TrkB). In doing so, the antibodies may bind to a ligand binding site and block the binding of a native ligand (e.g., brain-derived neurotrophic factor (BDNF) or neurotrophin-3), act as an antagonist or act as an agonist. In some embodiments, the anti-TrkB antibodies of the present invention act as agonists of a TrkB receptor. A TrkB antibody agonist is an antibody that specifically binds TrkB and activates or increases TrkB-mediated intracellular signaling. The anti-TrkB antibodies optionally can be multimerized and used according to the methods of this invention. The anti-TrkB antibodies can be a full-length tetrameric antibody (i.e., having two light chains and two heavy chains), a single chain antibody (e.g., a ScFv), or a molecule comprising antibody fragments that form one or more antigen-binding sites and confer TrkB-binding specificity, e.g., comprising heavy and light chain variable regions (for instance, Fab' or other similar fragments).

Anti-TrkB antibody fragments can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc. When present, the constant regions of the anti-TrkB antibodies can be any type or subtype, as appropriate, and can be selected to be from the species of the subject to be treated by the present methods (e.g., human, non-human primate or other mammal, for example, agricultural mammal (e.g., equine, ovine, bovine, porcine, camelid), domestic mammal (e.g., canine, feline) or rodent (e.g., rat, mouse, hamster, rabbit).

Anti-TrkB antibodies or antigen-binding molecules of the invention also include single domain antigen-binding units which have a camelid scaffold. Animals in the camelid family include camels, llamas, and alpacas. Camelids produce functional antibodies devoid of light chains. The heavy chain variable (VH) domain folds autonomously and functions independently as an antigen-binding unit. Its binding surface involves only three CDRs as compared to the six CDRs in classical antigen-binding molecules (Fabs) or single chain variable fragments (scFvs). Camelid antibodies are capable of attaining binding affinities comparable to those of conventional antibodies. Camelid scaffold-based anti-TrkB molecules with binding specificities of the anti-TrkB antibodies exemplified herein can be produced using methods well known in the art, e.g., Dumoulin et al., Nature Struct. Biol. 11:500-515, 2002; Ghahroudi et al., FEBS Letters 414:521-526, 1997; and Bond et al., J Mol. Biol. 332:643-55, 2003.

The improved anti-TrkB antibodies of the invention are engineered human antibodies with V-region sequences having substantial amino acid sequence identity to human germ-line V-region sequences while retaining the specificity and affinity of a reference antibody. See, U.S. Patent Publication No. 2005/0255552 and U.S. Patent Publication No. 2006/0134098, both of which are hereby incorporated herein by reference. The process of improvement identifies minimal sequence information required to determine antigen-binding specificity from the variable region of a reference antibody, and transfers that information to a library of human partial V-region gene sequences to generate an epitope-focused library of human antibody V-regions. A microbial-based secretion system can be used to express members of the library as antibody Fab fragments and the library is screened for antigen-binding Fabs, for example, using a colony-lift binding assay. See, e.g., U.S. Patent Publication No. 2007/0020685. Positive clones can be further characterized to identify those with the highest affinity. The resultant engineered human Fabs retain the binding specificity of the parent, reference anti-TrkB antibody, typically have equivalent or higher affinity for antigen in comparison to the parent antibody, and have V-regions with a high degree of sequence identity compared with human germ-line antibody V-regions.

The minimum binding specificity determinant (BSD) required to generate the epitope-focused library is typically represented by a sequence within the heavy chain CDR3 ("CDRH3") and a sequence within the light chain of CDR3 ("CDRL3"). The BSD can comprise a portion or the entire length of a CDR3. The BSD can be comprised of contiguous or non-contiguous amino acid residues. In some cases, the epitope-focused library is constructed from human V-segment sequences linked to the unique CDR3-FR4 region from the reference antibody containing the BSD and human germ-line J-segment sequences (see, FIG. 1 and U.S. Patent Publication No. 2005/0255552). Alternatively, the human V-segment libraries can be generated by sequential cassette replacement in which only part of the reference antibody V-segment is initially replaced by a library of human sequences. The identified human "cassettes" supporting binding in the context of residual reference antibody amino acid sequences are then recombined in a second library screen to generate completely human V-segments (see, U.S. Patent Publication No. 2006/0134098).

In each case, paired heavy and light chain CDR3 segments, CDR3-FR4 segments, or J-segments, containing specificity determinants from the reference antibody, are used to constrain the binding specificity so that antigen-binders obtained from the library retain the epitope-specificity of the reference antibody. Additional maturational changes can be introduced in the CDR3 regions of each chain during the library construction in order to identify antibodies with optimal binding kinetics. The resulting engineered human antibodies have V-segment sequences derived from the human germ-line libraries, retain the short BSD sequence from within the CDR3 regions and have human germ-line framework 4 (FR4) regions.

Accordingly, in some embodiments, the anti-TrkB antibodies contain a minimum binding sequence determinant (BSD) within the CDR3 of the heavy and light chains derived from the originating or reference monoclonal antibody. The remaining sequences of the heavy chain and light chain variable regions (CDR and FR), e.g., V-segment and J-segment, are from corresponding human germline and affinity matured amino acid sequences. The V-segments can be selected from a human V-segment library. Further sequence refinement can be accomplished by affinity maturation.

In another embodiment, the heavy and light chains of the anti-TrkB antibodies contain a human V-segment from the corresponding human germline sequence (FR1-CDR1-FR2-CDR2-FR3), e.g., selected from a human V-segment library, and a CDR3-FR4 sequence segment from the originating monoclonal antibody. The CDR3-FR4 sequence segment can be further refined by replacing sequence segments with corresponding human germline sequences and/or by affinity maturation. For example, the FR4 and/or the CDR3 sequence surrounding the BSD can be replaced with the corresponding human germline sequence, while the BSD from the CDR3 of the originating monoclonal antibody is retained.

In some embodiments, the corresponding human germline sequence for the heavy chain V-segment is Vh1-02. In some embodiments, the corresponding human germline sequence for the heavy chain is J-segment is JH4. In some embodiments, the heavy chain J-segment comprises the human germline JH4 partial sequence WGQGTLVTVSS (SEQ ID NO:50). The full-length J-segment from human germline JH4 is YFDYWGQGTLVTVSS (SEQ ID NO:74). The variable region genes are referenced in accordance with the standard nomenclature for immunoglobulin variable region genes. Current immunoglobulin gene information is available through the worldwide web, for example, on the ImMunoGeneTics (IMGT), V-base and PubMed databases. See also, Lefranc, *Exp Clin Immunogenet.* 2001; 18(2):100-16; Lefranc, *Exp Clin Immunogenet.* 2001; 18(3):161-74; *Exp Clin Immunogenet.* 2001; 18(4):242-54; and Giudicelli, et al., *Nucleic Acids Res.* 2005 Jan. 1; 33(Database issue):D256-61.

In some embodiments, the corresponding human germline sequence for the light chain V-segment is VKII A23. In some embodiments, the corresponding human germline sequence for the light chain J-segment is Jk2. In some embodiments, the light chain J-segment comprises the human germline Jk2 partial sequence FGQGTKLEIK (SEQ ID NO:61). The full-length J-segment from human germline Jk2 is YTFGQGTKLEIK (SEQ ID NO:75).

In some embodiments, the heavy chain V-segment shares at least 90%, 93%, 95%, 96%, 97%, 98%, 99% or 100% sequence identity to the amino acid sequence QVQLVQSGAEVKKPGASVKVSCKASGYTFT(G/A)Y(D/Y)MH-WVRQAPGQGLEWMG WI(D/N)P(N/R)SG(G/D)T(N/R/S)Y(A/K)QKFQGRVTMTRDTSISTAYMEL(H/S)RL(R/T)SDDTAVYYC(A/T)(G/R) (SEQ ID NO:16). In some embodiments, the light chain V-segment shares at least 90%, 93%, 95%, 96%, 97%, 98%, 99% or 100% sequence identity to the amino acid sequence D(I/V)VMTQ(S/T)PLS(L/S)PVTLGQPASISCRSSQSL(L/V)HS(D/N)GNTYL(N/S)W(L/Y) QQ(K/R/T)PGQPPRLLIYKISNRFSGVPDRFSGS-GAGTDFTLKISRVEAEDVGVYYC (SEQ ID NO:24).

In some embodiments, the heavy chain V-segment shares at least 90%, 93%, 95%, 96%, 97%, 98%, 99% or 100% sequence identity to an amino acid sequence selected from the group consisting of SEQ ID NO:12, SEQ ID NO:13, SEQ ID NO:14 or SEQ ID NO:15.

In some embodiments, the light chain V-segment shares at least 90%, 93%, 95%, 96%, 97%, 98%, 99% or 100% sequence identity to an amino acid sequence selected from the group consisting of SEQ ID NO:17, SEQ ID NO:18, SEQ ID NO:19, SEQ ID NO:20. SEQ ID NO:21, SEQ ID NO:22 or SEQ ID NO:23.

In some embodiments:
i) the heavy chain CDR3 comprises amino acid sequence motif V(T/V)(S/T/R/N)WFAY (SEQ ID NO:34); and
ii) the light chain CDR3 comprises amino acid sequence motif (S/M)QGT(H/A)(E/V/I)PYT (SEQ ID NO:42).

In some embodiments:
i) the heavy chain CDR3 comprises an amino acid sequence selected from the group consisting of VTTWFAY (SEQ ID NO:32) and VTSWFAY (SEQ ID NO:33); and
ii) the light chain CDR3 comprises an amino acid sequence selected from the group consisting of MQGTHEPYT (SEQ ID NO:40) and MQGTHVPYT (SEQ ID NO:41).

In some embodiments, the antibodies of the invention comprise a heavy chain variable region comprising a CDR1 comprising an amino acid sequence (A/G)Y(D/Y)MH (SEQ ID NO:27); a CDR2 comprising an amino acid sequence WI(D/N)P(N/R)SG(G/D)T(N/R/S)Y(A/K)QKFQG (SEQ ID NO:31); and a CDR3 comprising an amino acid sequence of V(T/V)(S/T/R/N)WFAY (SEQ ID NO:34).

In some embodiments, the antibodies of the invention comprise a light chain variable region comprising a CDR1 comprising an amino acid sequence RSSQSL(L/V)HSNGNTYL(N/S) (SEQ ID NO:38); a CDR2 comprising an amino acid sequence KISNRFS (SEQ ID NO:39); and a CDR3 comprising an amino acid sequence of (S/M)QGT(H/A)(E/V/I)PYT (SEQ ID NO:42).

In some embodiments, the heavy chain variable region comprises a FR1 comprising the amino acid sequence of SEQ ID NO:43; a FR2 comprising the amino acid sequence of SEQ ID NO:44; a FR3 comprising the amino acid sequence of SEQ ID NO:49; and a FR4 comprising the amino acid sequence of SEQ ID NO:50. The identified amino acid sequences may have one or more substituted amino acids (e.g., from affinity maturation) or one or two conservatively substituted amino acids.

In some embodiments, the light chain variable region comprises a FR1 comprising an amino acid sequence of SEQ ID NO:55; a FR2 comprising the amino acid sequence of SEQ ID NO:59; a FR3 comprising the amino acid sequence of SEQ ID NO:60; and a FR4 comprising the amino acid sequence of SEQ ID NO:61. The identified amino acid sequences may have one or more substituted amino acids (e.g., from affinity maturation) or one or two conservatively substituted amino acids.

Over their full length, the variable regions of the anti-TrkB antibodies of the present invention generally will have an overall variable region (e.g., FR1-CDR1-FR2-CDR2-FR3-CDR3-FR4) amino acid sequence identity of at least about 90%, for example, at least about 91%, 92%, 93%, 94%, 95%, 96%, 97%, 98%, 99% or 100% to the corresponding human germline variable region amino acid sequence. For example, the heavy chain of the anti-TrkB antibodies can share at least about 91%, 92%, 93%, 94%, 95%, 96%, 97%, 98%, 99% or 100% amino acid sequence identity to the human germline variable region Vh1-02/JH4. The light chain of the anti-TrkB antibodies can share at least about 91%, 92%, 93%, 94%, 95%, 96%, 97%, 98%, 99% or 100% amino acid sequence identity to the human germline variable region VKII A23/Jk2. In some embodiments, only amino acids within the framework regions are added, deleted or substituted. In some embodiments, the sequence identity comparison excludes the CD3.

In some embodiments, the anti-TrkB antibodies of the invention comprise a heavy chain variable region having at least 90%, 91%, 92%, 93%, 94%, 95%, 96%, 97%, 98%, 99% or 100% amino acid sequence identity to a heavy chain variable region of SEQ ID NO:4 and comprise a light chain variable region having at least 90%, 91%, 92%, 93%, 94%, 95%, 96%, 97%, 98%, 99% or 100% amino acid sequence identity to a light chain variable region of SEQ ID NO:11.

In some embodiments, the anti-TrkB antibodies of the invention comprise a heavy chain variable region having at least 90%, 91%, 92%, 93%, 94%, 95%, 96%, 97%, 98%, 99% or 100% amino acid sequence identity to a heavy chain variable region selected from the group consisting of SEQ ID NO:1, SEQ ID NO:2 and SEQ ID NO:3, and comprise a light chain variable region having at least 90%, 91%, 92%, 93%, 94%, 95%, 96%, 97%, 98%, 99% or 100% amino acid sequence identity to a light chain variable region selected from the group consisting of SEQ ID NO:5, SEQ ID NO:6, SEQ ID NO:7, SEQ ID NO:8, SEQ ID NO:9 and SEQ ID NO:10.

In some embodiments, the anti-TrkB antibodies of the invention comprise a heavy chain variable region having at least 90%, 91%, 92%, 93%, 94%, 95%, 96%, 97%, 98%, 99% or 100% amino acid sequence identity to a heavy chain variable region of SEQ ID NO:1 and comprise a light chain variable region having at least 90%, 91%, 92%, 93%, 94%, 95%, 96%, 97%, 98%, 99% or 100% amino acid sequence identity to a light chain variable region of SEQ ID NO:8 (i.e., clone LFC325).

In some embodiments, the anti-TrkB antibodies of the invention comprise a heavy chain variable region having at least 90%, 91%, 92%, 93%, 94%, 95%, 96%, 97%, 98%, 99% or 100% amino acid sequence identity to a heavy chain variable region of SEQ ID NO:1 and comprise a light chain variable region having at least 90%, 91%, 92%, 93%, 94%, 95%, 96%, 97%, 98%, 99% or 100% amino acid sequence identity to a light chain variable region of SEQ ID NO:9 (i.e., clone LFC327).

In some embodiments, the anti-TrkB antibodies of the invention comprise a heavy chain variable region having at least 90%, 91%, 92%, 93%, 94%, 95%, 96%, 97%, 98%, 99% or 100% amino acid sequence identity to a heavy chain variable region of SEQ ID NO:1 and comprise a light chain variable region having at least 90%, 91%, 92%, 93%, 94%, 95%, 96%, 97%, 98%, 99% or 100% amino acid sequence identity to a light chain variable region of SEQ ID NO:10 (i.e., clone LFD253).

In some embodiments, the anti-TrkB antibodies of the invention comprise a heavy chain variable region having at least 90%, 91%, 92%, 93%, 94%, 95%, 96%, 97%, 98%, 99% or 100% amino acid sequence identity to a heavy chain variable region of SEQ ID NO:3 and comprise a light chain variable region having at least 90%, 91%, 92%, 93%, 94%, 95%, 96%, 97%, 98%, 99% or 100% amino acid sequence identity to a light chain variable region of SEQ ID NO:8 (i.e., clone LFD254).

For identified amino acid sequences less than 20 amino acids in length, one or two conservative amino acid residue substitutions can be tolerated while still retaining the desired specific binding and/or antagonist activity.

The anti-TrkB antibodies of the present invention generally will bind TrkB with an equilibrium dissociation constant ($K_D$) of less than about $10^{-8}$ M or $10^{-9}$ M, for example, less than about $10^{-10}$ M or $10^{-11}$ M, in some embodiments less than about $10^{-12}$ M or $10^{-13}$ M.

3. Assays for Identifying TrkB Agonist Antibodies

Agonist antibodies can be identified by generating anti-TrkB antibodies and then testing each antibody for the ability trigger TrkB mediated events, e.g., initiating differentiation and/or dendrification of SH-SY5Y cells, measuring rescue from anoikis (apoptosis resulting from loss of cell-matrix interactions) in response to treatment of cells with potential TrkB agonist, or using a BaF3/TrkB cell proliferation assay.

SH-SY5Y assays involve plating out SH-SY5Y cells and treating the cells with retinoic acid with or without potential agonist antibodies and/or BDNF and subsequently measure neurite outgrowth. Generally, retinoic acid alone will induce a small amount of neurite outgrowth. BDNF alone should not induce significant neurite outgrowth and antibody alone should not induce significant neurite outgrowth. However, cells treated with retinoic acid, BDNF, and antibody should exhibit extensive neurite outgrowth. An exemplary SH-SY5Y assay is described in Kaplan D R, et al., *Neuron* 11:321-331 (1993). In assays testing for anti-TrkB agonist antibodies, BDNF is replaced with the test antibody. Positive control cells are exposed to BDNF.

BaF3 hematopoietic cells/TrkB cell proliferation assays involve measuring proliferation of cells stimulated by agonism of the TrkB receptor. For example, BaF3 cells are grown in complete RPMI medium with IL-3 and infected with a retrovirus that expresses TrkB. Cells are washed in the absence of IL-3 and plated. Potential agonist antibodies and cell survival is measured (e.g., using luminescent cell viability detection reagent such as Cell-Titer Glo™) after an appropriate incubation. Positive control cells are incubated with BDNF.

Anoikis assays involve resuspending rat intestinal epithelial (RIE)/TrkB cells (e.g., in DMEM medium) and contacting cells, optionally in multi-well containers, with a potential antibody agonist (e.g., $2.5 \times 10^4$ cells 10 µl of 10 µg/ml antibody). The mixtures are incubated in the presence or absence of a BDNF control and then measured for cell viability (e.g., using luminescent cell viability detection reagent such as Cell-Titer Glo™). An exemplary anoikis assay is described in Douma et al., *Nature* 430:1034-1039 (2004).

TrkB agonists can also be evaluated on SH-SY5Y cells for their ability to protect cells from vinblastine and cisplatin toxicity. This assays has been described in, e.g., Scala et al., *Cancer Res.* 56(16):3737-42 (1996); and Jaboin et al., *Cancer Res.* 62(22):6756-63 (2002).

4. Methods of Using Anti-TrkB Agonist Antibodies

The anti-TrkB agonist antibodies of the invention can be used to treat or ameliorate any diseases or conditions that benefit from increased TrkB activity, including respiratory disorders and diseases, particularly those resulting from insufficient TrkB signaling; disorders and diseases resulting from BDNF insufficiency; and lower intestinal gut motility diseases resulting from insufficient TrkB signaling (e.g., inflammatory bowel syndrome).

TrkB agonizing antibodies of the invention interact with TrkB and are thereby capable of modulating TrkB functions. The TrkB agonizing antibodies of the invention can modulate (e.g., promote) one or more biological functions of TrkB. For example, a TrkB agonist antibody can modulate dimerization of TrkB, and subsequent autophosphorylation of specific tyrosine residues on the TrkB intracellular domain. By way of further example, a TrkB agonist antibody can initiate TrkB-related intracellular signaling cascades (e.g., the mitogen-activated protein kinase, phosphatidylinositol 3-kinase, and PLO), pathways) that lead to the suppression of neuron death, the promotion of neurite outgrowth, and other effects of the neurotrophins In some embodiments, the TrkB agonist antibodies described herein act as a BDNF mimetic, and can be used to recapitulate the trophic activities of BDNF and other TrkB agonist ligands, thereby exerting neuroprotective and neurotrophic effects. The anti-TrkB agonist antibodies of the present methods can compete with BDNF for binding to TrkB, and thereby activate, enhance, or perpetuate TrkB pathway activation and signaling. In some embodiments, said TrkB agonist antibodies bind to the TrkB Ligand Binding Domain, thereby competing with BDNF for binding to TrkB.

Accordingly, the TrkB agonizing antibodies can be used to facilitate TrkB pathway signaling in vitro and in vivo. The TrkB agonizing antibodies of the invention find use to e.g., diagnose, inhibit, prevent, ameliorate the symptoms of, protect against, and treat disorders associated with aberrantly low levels of TrkB pathway signaling (e.g., due to a BDNF insufficiency or insufficiency of another TrkB agonist ligand in an afflicted subject). Non-limiting examples of disorders associated with aberrant downregulation of TrkB signaling, e.g., include Rett Syndrome (RTT), which is characterized by mutations in the gene encoding MeCP2 (which binds directly to BDNF); severe obesity and developmental delay, due to a TrkB loss-of-function mutation. (Giles, S., et al. (2004) Nature Neuroscience 7:1187-9), Wilms' tumor, aniridia, genitourinary anomalies and mental retardation (WAGR) syndrome (Han, et al., *N Engl J Med* (2008) 359(9):918-27), obesity resulting from melanocortin receptor MC4R deficiency (Farooqi and O'Rahilly, *Endocrine Rev* (2006) 27(7): 710-18), cachexia/muscle wasting syndromes (Lin, et al., *PloS,* 3(4):e1900; WO 2007/088476).

The present invention therefore provides methods of treating, diagnosing, preventing, and/or ameliorating disorders and diseases resulting from BDNF deficiency (e.g., Rett Syndrome (RTT), WAGR Syndrome, obesity resulting from melanocortin receptor MC4R deficiency, cachexia/muscle wasting syndromes) comprising administering pharmaceutical compositions comprising a therapeutically or prophylactically effective amount of the TrkB agonizing antibodies described herein; and a pharmaceutical carrier. In some embodiments, the anti-TrkB antibodies described herein are administered systemically or peripherally, e.g., orally, inhalationally, intravenously, or intraperitoneally.

The anti-TrkB antibodies described herein also find use in treating, diagnosing, preventing, and/or ameliorating respiratory diseases and disorders, particularly those resulting from insufficient TrkB activity. Exemplary respiratory disorders include Rett Syndrome, sleep apnea, Pickwickian Syndrome and others described herein.

In some embodiments, the pharmaceutical composition further comprises a separate and independent agent for use in treating, diagnosing, preventing, and/or ameliorating symptoms of respiratory distress (e.g., breathing difficulties), such as small molecule activators of the norepinephrine and/or serotonin pathways (examples include without limitation the tricyclic antidepressant desipramine (DMI), the serotonin 1A receptor partial agonist, buspirone, and the more selective antidepressants Fluoxetine and Reboxetine), an activator of glutamatergic AMPA receptors, e.g., AMPAkine CX546, prostaglandin, progesterone, or potentiators of TrkB activity (e.g., protein tyrosine phosphatase inhibitors).

In some embodiments, a therapeutically and/or prophylactically effective amount of a second agent effective in treating, diagnosing, preventing, and/or ameliorating respiratory disorders or symptoms of respiratory distress is administered to the individual in combination with the antibody agonist of TrkB (or pharmaceutical composition containing the same). In some embodiments, the second agent and the antibody agonist of TrkB (or pharmaceutical composition containing the same) are administered as a mixture. In some embodiments, the second agent is selected from the group consisting of small molecule activators of the norepinephrine and/or serotonin pathways (examples include the tricyclic antidepressant desipramine (DMI), the serotonin 1A receptor partial agonist, buspirone, and the more selective antidepressants Fluoxetine and Reboxetine), an activator of glutamatergic AMPA receptors, e.g., AMPAkine CX546, prostaglandin, progesterone, or potentiators of TrkB activity (e.g., protein tyrosine phosphatase inhibitors).

The present invention also provides methods of treating, diagnosing, preventing, and/or ameliorating symptoms of respiratory distress or respiratory disorders resulting from deficient intracellular signaling from TrkB, comprising administering an anti-TrkB agonizing antibody or pharmaceutical composition comprising the same. Said symptoms include but are not limited to breathing difficulties (e.g., stridor or wheezing, breath holding, shallow breathing, hyperventilation, prolonged apneas), poor or decreased oxygenation of the blood (e.g., cyanosis, e.g., due to impaired absorption of oxygen, inadequate perfusion of the lungs with blood, etc.), reduced norepinephrine (NE) content, decrease of tyrosine hydroxylase (TH) expressing neurons in the medulla, and chest pain. In some embodiments, said methods comprise administering a therapeutically or prophylactically effective amount of an antibody agonist of Tyrosine Kinase Receptor B (TrkB), as described herein, to the individual. In some embodiments, said methods comprise administering a pharmaceutical composition comprising a therapeutically or prophylactically effective amount of TrkB agonizing antibody and a pharmaceutical carrier to the individual. In some embodiments, the individual has Rett Syndrome and/or is experiencing one or more symptoms of respiratory distress. In some embodiments, the individual is predisposed to symptoms of respiratory distress.

In some embodiments, the TrkB agonist antibodies of the invention are used to treat or alleviate hyperglycemia and/or diabetes or symptoms thereof in an individual. Alternatively, or in combination, the antibodies of the invention can be used to reduce weight in an individual in need thereof. In some embodiments, the antibodies are used to alleviate obesity. This can be particularly useful as obese individuals are more prone to insulin resistance and type II diabetes.

The present invention provides methods of suppressing neural cell death, comprising administering a TrkB agonizing antibody as described herein (or pharmaceutical compositions comprising the same). For example, the present invention also provides for methods of treatment or prevention of neurodegenerative or central nervous system (CNS) diseases by administration of the TrkB agonist antibodies of the invention to an individual in need thereof. Exemplary CNS diseases include, e g, Alzheimer's, Parkinson's, Huntington's or ALS diseases.

Increasing TrkB activation has also been implicated in alleviation of substance abuse. See, e.g., U.S. Patent Publication No. 2005/0203011. Accordingly, the present invention provides for methods of alleviating substance (e.g., alcohol, nicotine and/or narcotics) abuse and dependence by administering the TrkB agonist antibodies of the invention to an individual in need thereof.

In some embodiments, the antibody is a humanized antibody. In some embodiments, the antibody is a single chain antibody. In some embodiments, the antibody does not bind to Tyrosine Kinase Receptor A or Tyrosine Kinase Receptor C. In some embodiments, the antibody does not bind to neurotrophin receptor p75NR. In some embodiments, the antibody specifically binds to human TrkB, with minimal or no binding to the TrkB of other species (e.g., non-human primate or mouse TrkB). In some embodiments, the antibody specifically binds to human TrkB, and to the TrkB of other species as well (i.e., cross-reacts with TrkB of other species including mouse, rat, and/or non-human primate (e.g., a cynomolgus monkey, or a rhesus monkey).

5. Pharmaceutical Compositions

The invention provides pharmaceutical compositions comprising the anti-TrkB antibodies or antigen-binding molecules formulated together with a pharmaceutically acceptable carrier. The compositions can additionally contain other therapeutic agents that are suitable for treating or preventing a given disorder. Pharmaceutically carriers enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, intranasal, inhalational, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

The antibodies, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

In some embodiments, the composition is sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. Pharmaceutically acceptable carriers are determined in part by the particular composition being administered, as well as by the particular method used to administer the composition. Accordingly, there is a wide variety of suitable formulations of pharmaceutical compositions of the present invention. Applicable methods for formulating the antibodies and determining appropriate dosing and scheduling can be found, for example, in *Remington: The Science and Practice of Pharmacy*, $21^{st}$ Ed., 2005, Lippencott Williams & Wilkins (2006); and in *Martindale: The Complete Drug Reference*, Sweetman, 2005, London: Pharmaceutical Press., and in Martindale, *Martindale: The Extra Pharmacopoeia,* 31st Edition., 1996, Amer Pharmaceutical Assn, and Sustained and Controlled Release Drug Delivery Systems, J. R. Robinson, ed., Marcel Dekker, Inc., New York, 1978, each of which are hereby incorporated herein by reference. Pharmaceutical compositions are preferably manufactured under GMP conditions. Typically, a therapeutically effective dose or efficacious dose of the anti-TrkB antibody is employed in the pharmaceutical compositions of the invention. The anti-TrkB antibodies are formulated into pharmaceutically acceptable dosage forms by conventional methods known to those of skill in the art. Dosage regimens are adjusted to provide the desired response (e.g., a therapeutic response). In determining a therapeutically or prophylactically effective dose, a low dose can be administered and then incrementally increased until a desired response is achieved with minimal or no undesired side effects. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies of the invention employed in the pharmaceutical composition at levels lower than that required to achieve the desired therapeutic effect and gradually increase the dosage until the desired effect is achieved. In general, effective doses of the compositions of the present invention vary depending upon many different factors, including the specific disease or condition to be treated, means of administration, target site, physiological state of the patient, whether the patient is human or an animal, other medications administered, and whether treatment is prophylactic or therapeutic. Treatment dosages need to be titrated to optimize safety and efficacy. For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months.

In embodiments where the agent is a nucleic acid, typical dosages can range from about 0.1 mg/kg body weight up to and including about 100 mg/kg body weight, e.g., between about 1 mg/kg body weight to about 50 mg/kg body weight. In some embodiments, about 1, 2, 3, 4, 5, 10, 15, 20, 30, 40 or 50 mg/kg body weight.

The antibody can be administered in single or divided doses. Antibody is usually administered on multiple occasions. Intervals between single dosages can be weekly, monthly or yearly. Intervals can also be irregular as indicated by measuring blood levels of anti-TrkB antibody in the patient. In some methods, dosage is adjusted to achieve a plasma antibody concentration of 1-1000 µg/ml and in some methods 25-300 µg/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The TrkB antibody agonist can be used in combination with agents known to be beneficial for reducing weight, reducing blood glucose levels, treat diabetes or alleviate diabetic symptoms, treating neurodegenerative diseases or reducing substance abuse. Exemplary agents used to treat diabetes include, e.g., insulin; sulfonylureas (e.g., Glipizide and Amaryl) and insulinotropic agents (e.g., nateglinide and repaglinide); metformin; PPARgamma agonists (e.g., rosiglitizone and pioglitazone) as well as PPARalpha, PPARdelta, PPARalpha/gamma dual agonists and PPARalpha/gamma/delta pan agonists; alpha-glucosidase inhibitors (e.g., Acarbose); DPP-IV inhibitors (e.g., vildagliptin); and GLP-1/GLP-1 analogs (e.g., exenatide). Exemplary agents used to treat obesity include, e.g., lipase inhibitors (e.g., orlistat); sibutramine; CB-1 inhibitors (e.g., rimonabant); topiramate; amylin/amylin analogs (e.g., pramlintide), leptin, PYY/PYY analogs; and GLP-1/GLP-1 analogs (e.g., exenatide).

Active agents that can be administered together in a mixture with the TrkB agonist antibody or each can be administered separately. The antibody agent and the other active agent can, but need not, be administered concurrently.

EXAMPLES

The following examples are offered to illustrate, but not to limit the claimed invention.

Example 1

The following example provides the construction and screening of anti-TrkB antibodies with substantial amino acid sequence identity to human germline V-region sequences.
Methods
Sub-Cloning of V-Regions The V-regions were sub-cloned from the originating monoclonal antibody A 10F18.2. PCR was used to amplify the V-genes of the V-heavy and V-kappa regions and incorporate restriction enzyme sites suitable for cloning into expression vectors. V-regions were cloned as Fab fragments and expressed in *E. coli* from expression vectors. The reference Fab was tested for TrkB-antigen binding and is referred to as TR3-1.

The V-regions were also cloned into IgG expression vectors. Using PCR amplification and primers with appended restriction sites, the Vh regions were amplified and cloned into an expression vector containing the human IgG1 constant region and conferring ampicillan and neomycin resistance. Using PCR amplification and primers with appended restriction sites, the Vk regions were amplified and cloned into an expression vector containing the human kappa constant region and confering ampicillan and hygromycin resistance. These vectors were tested in various combinations to produce panels of full IgG for functional analysis.
Antibody Purification Fab fragments were expressed by secretion from *E. coli* using expression vectors. Cells were grown in 2xYT medium to an OD600 of 0.6. Expression was induced using IPTG for 3 hours at 33° C. Assembled Fab was obtained from periplasmic fractions and purified by affinity chromatography using Streptococcal Protein G (HiTrap Protein G HP columns; GE Healthcare) according to standard methods. Fabs were eluted in pH 2.0 buffer, immediately adjusted to pH 7.0 and dialyzed against PBS pH 7.4 (PBS is without calcium and magnesium).

IgGs were prepared from the media (serum-free) of transiently transfected CHO cells. The IgGs were purified by affinity chromatography using Protein A (HiTrap Protein A HP columns; GE Healthcare) according to standard methods. Fabs were eluted in pH 2.7 buffer, immediately adjusted to pH 7.0 and dialyzed against PBS pH 7.4 (PBS is without calcium and magnesium).

General ELISA 100 ng of recombinant Fc-TrkB antigen was bound to a 96 well microtiter plate by overnight incubation at 4° C. The plate was blocked with a solution of 5% milk in PBS-Tween ("PBST") for one hour at 33° C. The purified Fabs were diluted in PBS and 50 µl was added to each well. After one hour incubation at 33° C., the plate was rinsed three times with PB ST. 50 µl of anti-human-kappa chain HRP conjugate (Sigma; diluted to 0.1 ng/ml in PBST) was added to each well and the plate was incubated for 40 min at 33° C. The plate was washed three times with PBST and once with PBS. 100 µl of 3,3',5,5'-tetramethylbenzidine ("TMB") substrate (Sigma) was added to each well and the plate was incubated for ~5 min at room temperature. To stop the reaction, 100 µl of 0.2 N $H_2SO_4$ was added to each well. The plate was read at 450 nm in a spectrophotometer.

Blocking ELISA

ELISA plates were coated with 100 ng Fc-TrkB antigen. A 2-fold dilution series of A10F18.2 IgG was incubated with antigen for 1 hr at room temperature. The unbound IgG was rinsed off and a 50 nM solution of Fab was added to each well and incubated for 1 hr at RT. The unbound Fab was rinsed off and the bound Fab was detected with an anti-human kappa-HRP conjugate.

Colony Lift Binding Assay ("CLBA")

Screening of libraries of Fab fragments was carried out essentially as described (U.S. Patent Publication Nos. 2005/0255552 and 2006/0134098) using Antigen Fc-TrkB-coated nitrocellulose filters.

Affinity Measurements Using ForteBio

The binding kinetics of IgGs and Fab fragments were analyzed using a ForteBio Octet biosensor. Recombinant Fc-TrkB antigen was biotinylated using the EZ-link biotinylation kit (Pierce) according to the manufacturer's methods. The antigen was then coupled to streptavidin-coated sensors (ForteBio). Fab binding was monitored in real time using bio-layer interferometry analysis and software provided by the manufacturer. Affinities were calculated from the determined association and dissociation constants.

Affinity Measurements Using Biacore

All Biacore reagents were purchased from Biacore, a division of GE Healthcare (Piscataway, N.J.). Determination of kinetic binding parameters was done by surface plasmon resonance measurements using the optical biosensor Biacore S51. This technology allows the label-free determination of the microscopic rate constants for binding (ka) and dissociation (kd) of a ligand to a receptor. It is therefore especially suited for characterizing antibody-antigen interactions.

Binding studies on the improved antibodies were performed by immobilizing Fc-hTrkB onto a Series S CM-5 Biacore sensor chip (certified) (Biacore #BR-1005-30). Covalent binding of the Fc-fusion protein was done with the 'Amine Coupling Kit' (Biacore #BR-1000-50). The Fc-Fusion protein was attached to the EDC-activated dextran surface at 5 µg/ml in 10 mM sodium acetate, pH 4.5 (Biacore #BR-1003-50) at a flow rate of 10 µL/min A range of concentrations of improved antibodies were flowed over the Fc-TrkB captured chip in PBS plus 100 mM NaCl, 0.005% P20 (Biacore #BR-1000-54). The resulting sensorgrams were analyzed using the Biacore S51 Evaluation Software. Data from all concentrations was fitted globally to a 1:1 Langmuir model.

Anoikis Assay

Rat intestinal epithelial (RIE)-TrkB cells were used in the anoikis assays. RIE/TrkB cells were detached using Accutase (Innovative Cell Technologies Inc., San Diego, Calif.) and resuspended in complete DMEM medium. The cells were washed three times with serum-free DMEM, and resuspended in serum-free DMEM containing 0.1% BSA (Cell-culture grade, #A8806-5G Sigma) diluted from a stock of 2% BSA in PBS. The cells were then plated 60 ml/well at $4.2 \times 10^5$ cells/mL (=$2.5 \times 10^4$ cells/well) into 96-well Corning Costar ultra low cluster plates (Costar #3474). 10 ml of TrkB agonist antibody (stock in PBS) was added into test wells to a final concentration of between 1-20 µg/mL. The cells were incubated at 37° C. for 1 h. 10 ml of human BDNF (R&D, stock 20 mg/mL in 0.1% BSA/PBS) was added into control well to a final concentration of between 10-50 ng/mL. The BDNF was diluted with DMEM(SF)/0.1% BSA. The cells were then incubated for an additional 24-48 h. 80 ml/well of Cell-Titer Glo (Promega, Madison, Wis.) was added and the plate subjected to gentle shaking. After 15 minutes, the liquid was transferred into a 96-well white, clear bottom plate and the luminescence read.

Results

Cloning and Expression of V-Regions

The Fab TR3-1 has intact V-regions from the originating antibody, A10F18.2, fused with human constant regions and was purified from *E. coli*. In a dilution ELISA test of TrkB antigen binding the cloned Fab produced binding curves that were dependent on antibody concentration (data not shown).

Library Construction and V-Region Cassettes

Epitope-focused libraries were constructed from human V-segment library sequences linked to the unique CDR3-FR4 region from the originating antibody containing the binding specificity determinant ("BSD") and human germ-line J-segment sequences. These "full-length" libraries were used as a base for construction of "cassette" libraries in which only part of the V-segment in the originating antibody is initially replaced by a library of human sequences. Two types of cassettes were constructed. Cassettes for both V-heavy and V-kappa chains were made by bridge PCR with overlapping common sequences within the framework 2 region. In this way "front-end" and "middle" human cassette libraries were constructed for human V-heavy 1 and V-kappa II isotypes. Human cassettes which supported binding to TrkB antigen were identified by colony-lift binding assay and ranked according to affinity in ELISA and Forte analysis. Pools of the highest affinity cassettes were then recombined in a second library screen to generate completely human V-segments.

After the identification of a pool of high affinity Fabs with human V-segments, affinity maturation libraries were built. The common BSD sequences of a panel of Fab clones with human V-segments were mutated using degenerate PCR primers to generate libraries. These mutagenic libraries were screened using colony lift binding assay. The selected Fabs were ranked for affinity with ELISA and Forte analysis. Mutations that supported similar or improved affinity for antigen when compared to the reference TR3-1 Fab were identified.

Additionally, a point mutation to human germ-line was made in the CDR3 of the light chain for each Fab with human V-segments. Position 89 (Chothia numbering) was changed from S to M, the amino acid coded for by all human germ-line VkII segments at that position.

Figure 3:
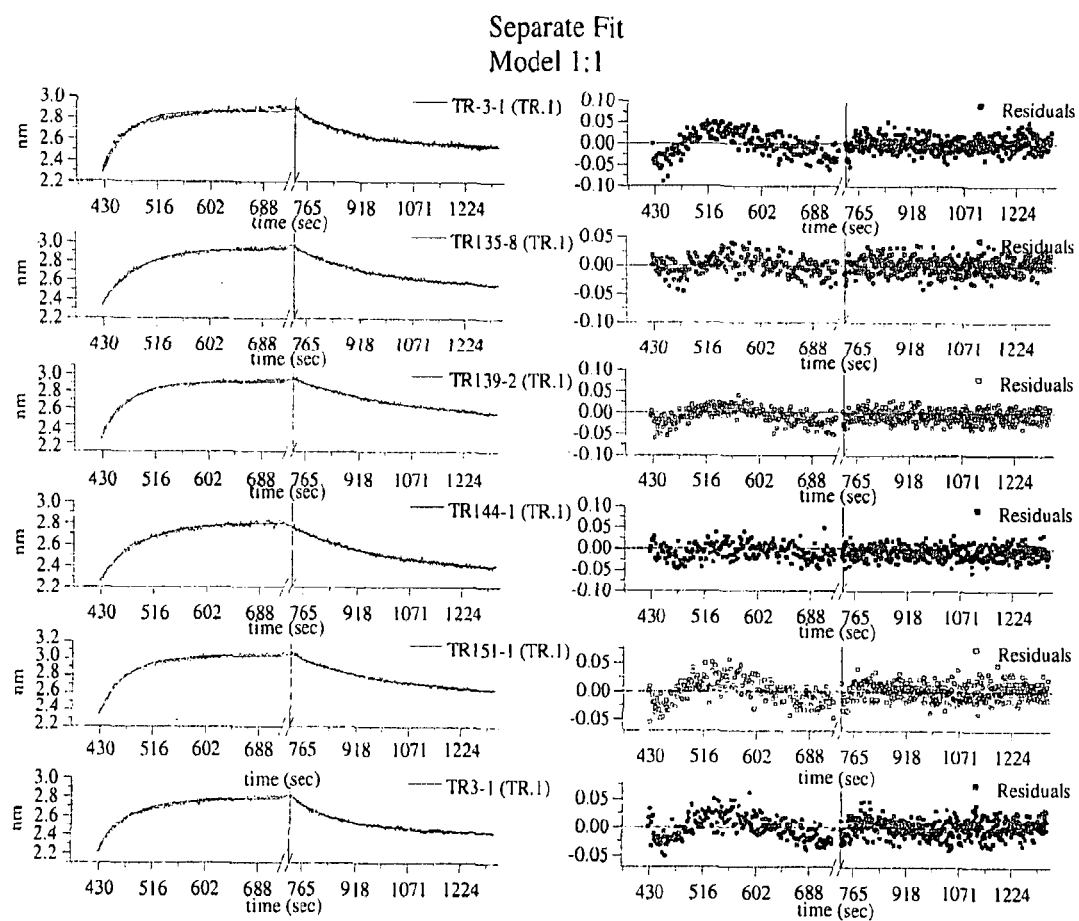
FIG. 3 illustrates an analysis of Fab binding to recombinant TrkB antigen by bio-layer interferometry using ForteBio Octet biosensor technology. The numerical data for these curves is shown in Tables 1 and 2.

Affinity of Fabs and IgGs with Human V-Segments for Human TrkB Antigen using Forte Octet Analysis Fabs with human V-segments were isolated from colony-lift binding assays and confirmed by antigen-binding ELISA. The Fab clones showing strong positive signals in antigen-binding ELISA were purified and further characterized by kinetic comparison with the reference Fab TR3-1. Binding kinetics were analyzed using a ForteBio Octet system for real-time label-free monitoring of protein-protein interactions. Representative kinetic analyses are shown in FIG. 3. Calculated association and dissociation constants are shown in Tables 1 and 2.

TABLE 1

| Fab | Molar Conc [M] | Kd [1/s] | Ka [1/Ms] | KD [M] |
|---|---|---|---|---|
| TR-3-1 | 1E−7 | 6.61E−3 | 1.96E5 | 3.37E−8 |
| TR135-8 (SEQ ID NOs: 1 and 6) | 1E−7 | 4.39E−3 | 1.36E5 | 3.23E−8 |
| TR139-2 (SEQ ID NOs: 1 and 7) | 1E−7 | 3.17E−3 | 2.11E5 | 1.51E−8 |
| TR144-1 (SEQ ID NOs: 3 and 6) | 1E−7 | 3.92E−3 | 1.26E5 | 3.11E−8 |
| TR151-1 (SEQ ID NOs: 2 and 7) | 1E−7 | 3.95E−3 | 2.13E5 | 1.86E−8 |
| TR3-1 | 1E−7 | 6.90E−3 | 1.41E5 | 4.89E−8 |

Table 1 summarizes analysis of Fab binding to recombinant TrkB antigen by bio-layer interferometry using ForteBio Octet biosensor technology, showing association constant (Ka), dissociation constant (Kd) and calculated affinity (KD).

TABLE 2

| Fab | MolarConc [M] | Kd [1/s] | Ka [1/Ms] | KD [M] |
|---|---|---|---|---|
| TR3 | 1E−7 | 7.88E−3 | 2.80E5 | 2.82E−8 |
| TR134-4 (SEQ ID NOs: 1 and 5) | 1E−7 | 4.22E−3 | 1.18E5 | 3.56E−8 |
| TR135-8 (SEQ ID NOs: 1 and 6) | 1E−7 | 4.58E−3 | 1.44E5 | 3.19E−8 |
| TR139-2 (SEQ ID NOs: 1 and 7) | 1E−7 | 3.34E−3 | 2.35E5 | 1.42E−8 |
| TR144-1 (SEQ ID NOs: 3 and 6) | 1E−7 | 3.66E−3 | 1.23E5 | 2.97E−8 |

Table 2 summarizes analysis of Fab binding to recombinant TrkB antigen by bio-layer interferometry using ForteBio Octet biosensor technology, showing association constant (Ka), dissociation constant (Kd) and calculated affinity (KD).

Kinetic analysis of the Fab clones TR134-4, TR135-8, TR139-2, TR151-1 and TR144-1 and the reference clone TR3-1 all showed low nanomolar affinities for TrkB antigen. Clones TR139-2 and TR151-1 consistently had an improved off-rate (Kd) and a higher overall affinity when compared to the reference control. TR144-1, TR135-8 and TR134-4 consistently had about the same overall affinity when compared to the reference control.

Figure 4:
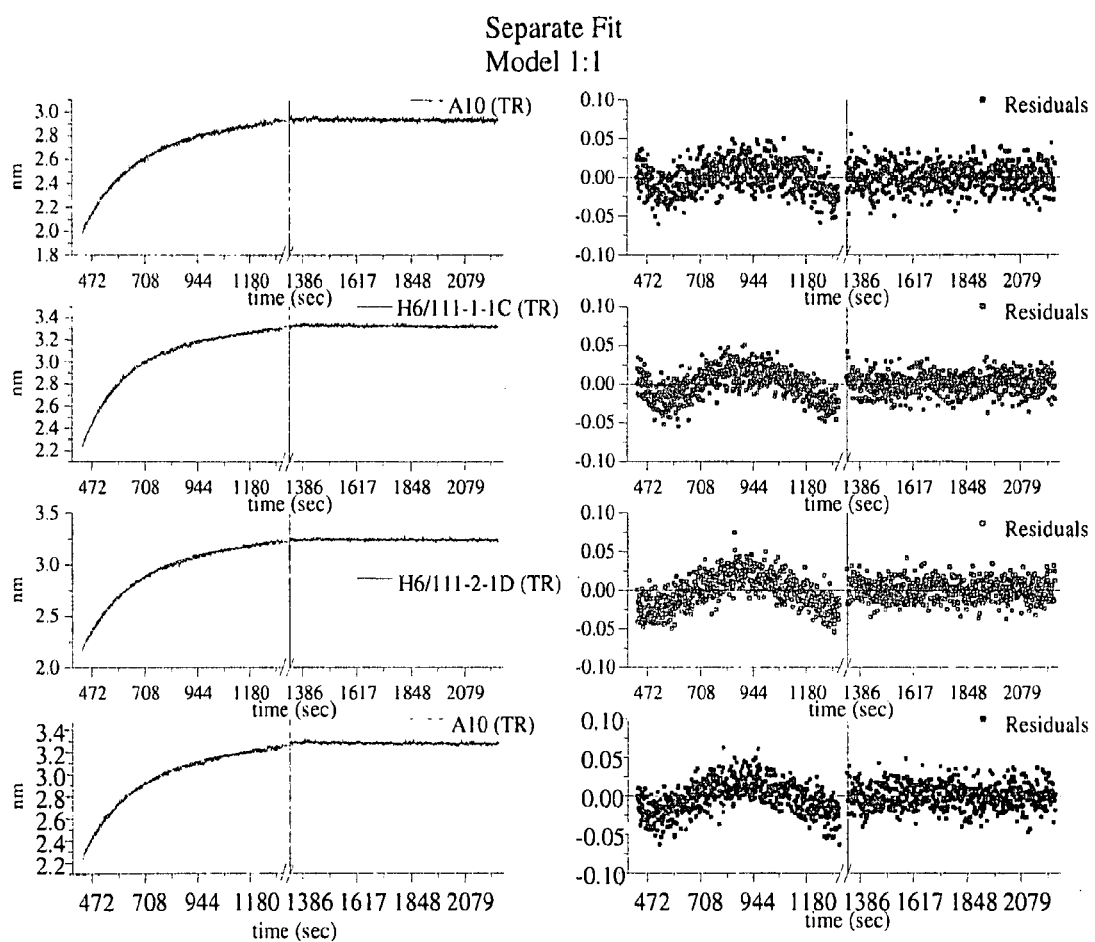
FIG. 4 illustrates an analysis of IgG binding to recombinant TrkB antigen by bio-layer interferometry using ForteBio Octet biosensor technology. The numerical data for these curves is shown in Table 3.
Figure 12:
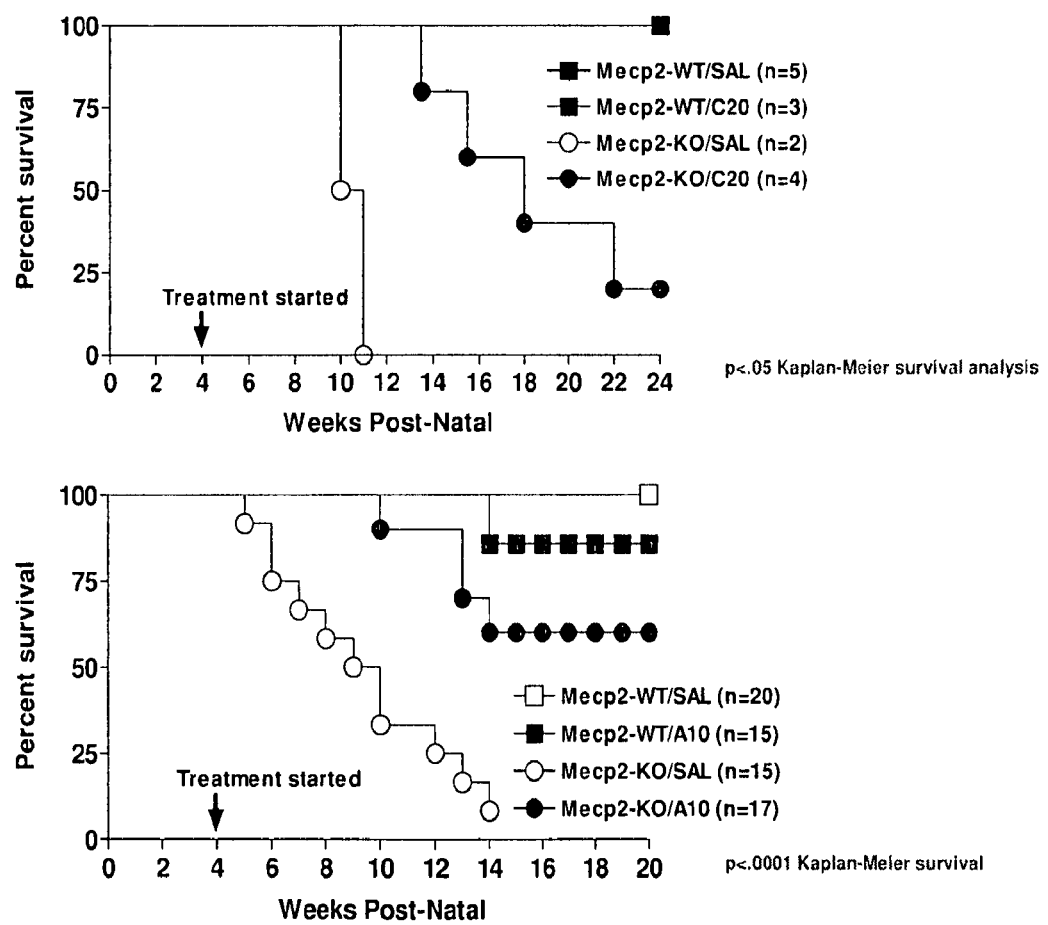
FIG. 12 illustrates that prolonged treatment with anti-TrkB agonist mAbs extends the lifespan of Mecp2-Bird mice. Mecp2tm1.1Bird null mice recapitulate many of the core respiratory dysfunctions of subjects suffering from Rett Syndrome, including: increased variability in the duration of the respiratory cycle, alternating periods of fast and slow breathing frequencies, occurrence of apneas, increased mean breathing frequency (and minute ventilation). The mice eventually die from fatal respiratory failure. Antibody A10 refers to the parental mouse monoclonal antibody which shares complementary binding determinant regions (CDRs) and minimal binding determinants with the improved anti-TrkB antibody agonists described herein
Figure 13:
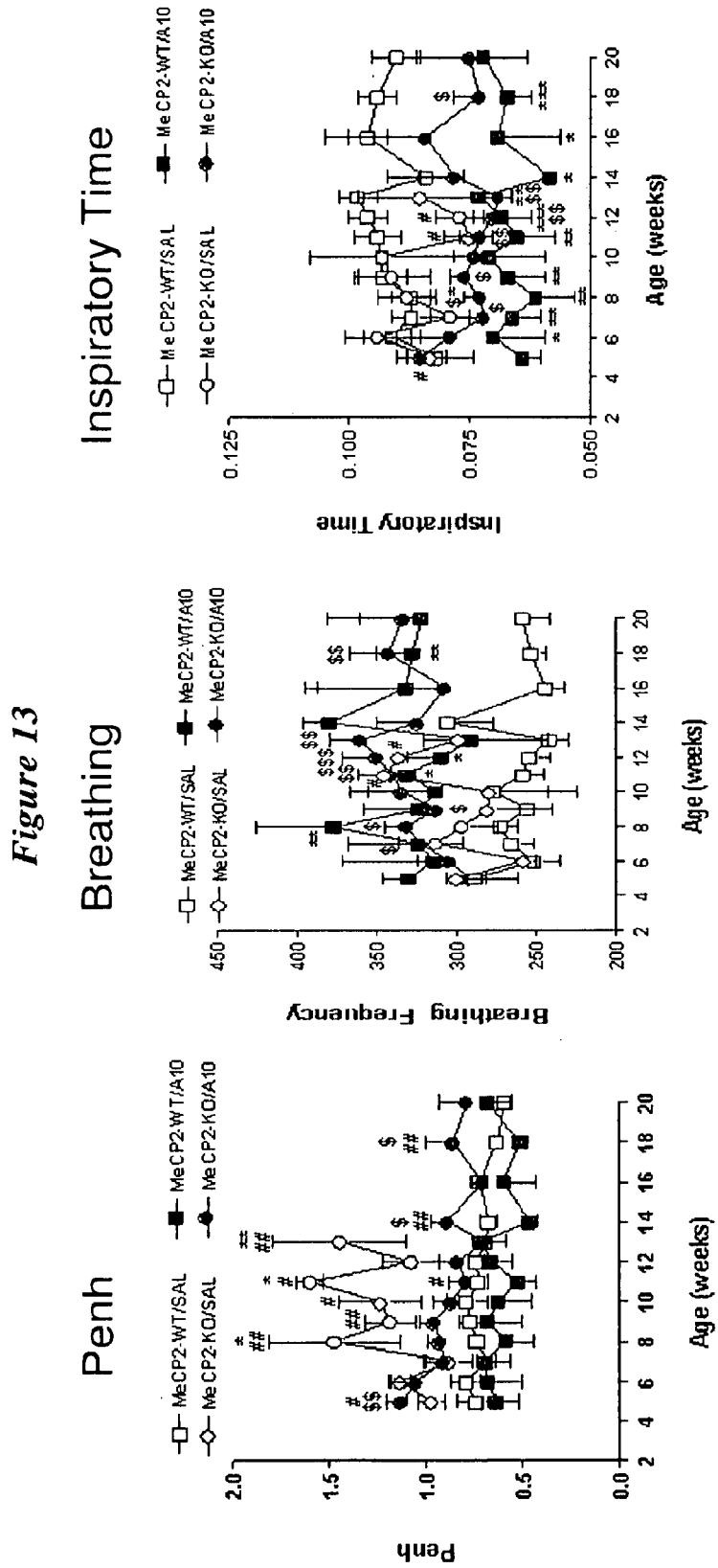
FIG. 13 illustrates improvement in respiratory function in Mecp2-Bird mice treated with anti-TrkB agonist mAbs. The respiratory parameters of Mecp2 mice following treatment with anti-TrkB agonist mAb treatment were evaluated by whole body plethysmography. Untreated Mecp2 mice showed an age-dependent increase in enhanced respiratory pause (Penh) which was reduced in mAb treated animals. The age-dependent Penh may be indicative of increased airway resistance, could phenocopy valsalva maneuver complications in RTT patients. Increased breathing frequency and decreased inspiration time were observed in both wild-type and Mecp2 mice following mAb treatment. *$p<0.05$, **$p<0.01$ vs same genotype, opposite treatment; # $p<0.05$, ## $p<0.01$, ### $p<0.001$ vs opposite genotype, same treatment; \$ $p<0.05$, \$\$ $p<0.01$, \$\$\$ $p<0.001$ MeCP2-KO/A10 vs MeCP2-WT/SAL. One-way ANOVA followed by Student's t-test.
Figure 14:
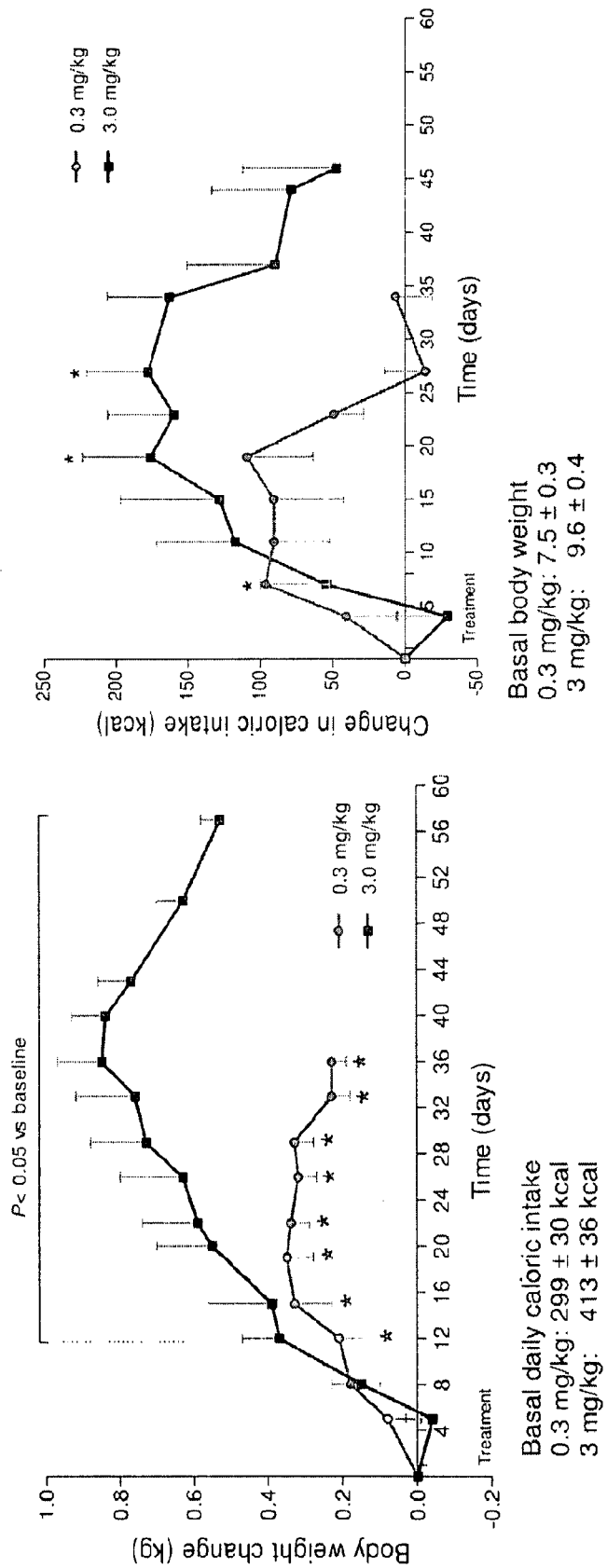
FIG. 14 illustrates the effect on food intake and body weight following intravenous administration of the anti-TrkB agonist mAb LFI987 to Cynomolgus monkeys. Antibody clone LFD253 was converted to LFI987 by transferring the HC variable regions into a silent IgG1 backbone. Animals were dosed with 0.3 and 3.0 mg/kg LFI987 i.v. 3 times, on days 1, 5 and 8. Data are means±SE; n=4-6. *$P<0.05$ vs. baseline by Anova for repeated measures followed by Dunnett's test LFI987 significantly increased food intake and body weight in a dose-dependent manner.

IgGs with human V-segments were also prepared from transient transfections of CHO cells. IgG preparations were purified and further characterized by kinetic comparison with the reference IgG A10F18.2. Binding kinetics for two of the IgGs with human V-segments were analyzed using a ForteBio Octet system for real-time label-free monitoring of protein-protein interactions. Representative kinetic analyses are shown in FIG. 4. Calculated association and dissociation constants are shown in Table 3. The results indicate that the IgGs with human V-segments bind antigen with an affinity equal to the reference A10F18.2 IgG.

TABLE 3

| IgG | MolarConc [M] | Kd [1/s] | Ka [1/Ms] | KD [M] |
|---|---|---|---|---|
| A10F18.2 IgG | 1E−8 | 1.44E−5 | 3.79E5 | 3.79E−11 |
| TR127 Vh & TR119 Vk (SEQ ID NOs: 1 and 8) | 1E−8 | 1.52E−5 | 4.53E5 | 3.35E−11 |
| TR127 Vh & TR129 Vk (SEQ ID NOs: 1 and 9) | 1E−8 | 7.90E−6 | 4.01E5 | 1.97E−11 |
| A10F18.2 IgG | 1E−8 | 1.89E−5 | 3.96E5 | 4.77E−11 |

Table 3 summarizes analysis of IgG binding to recombinant TrkB antigen by bio-layer interferometry using ForteBio Octet biosensor technology, showing association constant (Ka), dissociation constant (Kd) and calculated affinity (KD).

Percentage Identity to Human Germline Sequence

V-regions were PCR-amplified, digested with restriction enzymes and cloned into IgG expression vectors. The heavy chains from TR134-4, TR144-1 and TR144-1 were PCR-amplified and digested with SalI and NheI; the resulting fragments were cloned into an expression vector containing human IgG1 constant region to yield TR127, TR143 and TR154, respectively. The light chains from TR134-4, TR135-8 and TR139-2 were PCR-amplified and digested with BssHII and BsiWI; the resulting fragments were cloned into an expression vector containing human kappa constant region to yield TR119, TR129 and TR137, respectively. The identity and integrity of the inserts were confirmed by DNA sequencing.

TABLE 4

| IgG Vector Combinations | Fab Version | % identity to Vh1-02[a] | % identity to VkII A23 |
|---|---|---|---|
| TR127 Vh & TR119 Vk (LFC325) (SEQ ID NOs: 1 and 8) | TR134-4 (SEQ ID NOs: 1 and 5) | 94% | 94% |
| TR127 Vh & TR129 Vk (LFC327) (SEQ ID NOs: 1 and 9) | TR135-8 (SEQ ID NOs: 1 and 6) | 94% | 94% |
| TR127 Vh & TR137 Vk | TR139-2 | 94% | 98% |

TABLE 4-continued

| IgG Vector Combinations | Fab Version | % identity to Vh1-02[a] | % identity to VkII A23 |
|---|---|---|---|
| (LFD253) (SEQ ID NOs: 1 and 10) | (SEQ ID NOs: 1 and 7) | | |
| TR143 Vh & TR129 Vk (ND) (SEQ ID NOs: 3 and 9) | TR144-1 (SEQ ID NOs: 3 and 6) | 90% | 94% |
| TR154 Vh & TR137 Vk (ND) (SEQ ID NOs: 2 and 10) | TR151-1 (SEQ ID NOs: 2 and 7) | 94% | 98% |
| TR143 Vh & TR119 Vk (LFD254) (SEQ ID NOs: 3 and 8) | ND* | 90% | 94% |

*ND = Not done;
[a] % identity to human germ-line excludes CDR3

Table 4 illustrates percentage identity to human germline sequence for the V-regions contained within the IgG expression vectors: all percentages represent identity to a single human germline sequence across the V-region and exclude the CDR3BSD sequences. Each of the Vh-regions and Vk-regions of the Fabs are extremely close to the human germline amino acid sequence.

Blocking ELISA to Show Epitope Specificity

Blocking ELISAs were done with purified Fabs containing human V-segments as described in the Methods section. Results are shown in FIG. 7. The binding of all Fab clones is blocked by an increasing concentration of the originating monoclonal antibody A10F18.2 IgG, indicating that the Fabs bind the same epitope as the originating monoclonal IgG.

Antibody Binding to the TrkB Protein by ELISA

IgG antibodies NVP-LFD253, NVP-LFD254, NVP-LFC325 and NVP-LFC327 were generated by transient transfection, purified as described as described herein and evaluated for specific binding to Fc-TrkB. An ELISA was performed using human TrkB and a dilution series of the respective antibody: LFD253, LFD254, LFC325 or LFC327. The ELISA assays show that LFD253, LFD254, LFC325 and LFC327 bind human TrkB. See, FIG. 8.

IgG with human V-segments (e.g., NVP-LFD253, NVP-LFD254, NVP-LFC325, and NVP-LFC327) bind specifically to TrkB but not to TrkA or TrkC. Purified IgG antibodies at 2 µg/ml were evaluated for specificity by examining its interaction with three different Trk family members (TrkA, TrkB and TrkC). Secondary Ab are replicates that were blocked and treated with only the goat-anti-human Fab-HRP detection Ab. As shown in FIG. 9A-D, none of LFD253, LFD254, LFC325 or LFC327 bind to either of these related Trk family receptors.

Anoikis Assay: Functional Agonism

Purified IgG (e.g., LFD253, LFD254, LFC325 or LFC327) were evaluated in an anoikis assay using rat intestinal epithelial (RIE)-TrkB cells. These cells are susceptible to anoikis (detachment dependent apoptosis), but can be rescued with activation of the TrkB receptor. LFD253 treatment was able to rescue RIE-TrkB cells from Anoikis, as measured by cell viability, and this effect was dose dependent. See, FIG. 10A-D. The EC50 calculated from this data for LFD253 is 4.1 ng/ml (28 pM). The EC50 calculated from this data for LFD254 is 24.0 ng/ml (160 pM). The EC50 calculated from this data for LFC325 is 41.8 ng/ml (280 pM). The EC50 calculated from this data for LFC327 is 26.9 ng/ml (180 pM).

Antibody Affinity Determination by Biacore

The kinetic constants for the binding of NVP-LFD253, NVP-LFD254, NVP-LFC325 and NVP-327 to immobilized Fc-TrkB were determined FIG. 11A-D show the details of a representative set of kinetic traces for each IgG. FIG. 11A shows sensorgrams of a titration of LFD253 from 62.5 nM diluted two-fold down to 3.9. FIG. 11B shows sensorgrams of a titration of LFD254 from 31.25 nM diluted two-fold down to 1.9. FIG. 11C shows sensorgrams of a titration of LFC325 from 31.25 nM diluted two-fold down to 1.95. FIG. 11D shows sensorgrams of a titration of LFC327 from 31.25 nM diluted two-fold down to 1.95. Table 5 shows the summary of data obtained when experiment was fitted globally to the Langmuir model using the Biacore S51 Evaluation Software. Although this antibody is bivalent, the binding was treated as a 1:1 event.

TABLE 5

| | $K_D$ (nM) | $k_d$ (1/s) | ka (1/M*s) | chi$^2$ |
|---|---|---|---|---|
| NVP-LFD253 | 0.165 | $3.25 \times 10^{-5}$ | $1.97 \times 10^5$ | 10.0 |
| NVP-LFD254 | 0.117 | $1.94 \times 10^{-5}$ | $1.66 \times 10^5$ | 0.05 |
| NVP-LFC325 | 0.114 | $4.85 \times 10^{-5}$ | $1.97 \times 10^5$ | 3.04 |
| NVP-LFC327 | 01465 | $5.76 \times 10^{-5}$ | $3.934 \times 10^5$ | 2.24 |

Table 5 shows both the fast association and the slow dissociation kinetics of the antibody-receptor complex. The best fit was obtained when the sensorgrams were treated globally.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A purified antibody that specifically binds TrkB, wherein the antibody comprises a heavy chain variable region and a light chain variable region, wherein the heavy chain variable region and the light chain variable region each comprise the following three complementary determining regions (CDRs): CDR1, CDR2 and CDR3; wherein:
   i) the CDR1 of the heavy chain variable region comprises an amino acid sequence of SEQ ID NO:25;
   ii) the CDR2 of the heavy chain variable region comprises an amino acid sequence selected from the group consisting of SEQ ID NO:28, SEQ ID NO:29 and SEQ ID NO:30;
   iii) the CDR3 of the heavy chain variable region comprises an amino acid sequence selected from the group consisting of SEQ ID NO:32 and SEQ ID NO:33;
   iv) the CDR1 of the light chain variable region comprises an amino acid sequence selected from the group consisting of SEQ ID NO:35, SEQ ID NO:36 and SEQ ID NO:37;
   v) the CDR2 of the light chain variable region comprises an amino acid sequence of SEQ ID NO:39;
   vi) the CDR3 of the light chain variable region comprises an amino acid sequence selected from the group consisting of SEQ ID NO:40 and SEQ ID NO:41.

2. The antibody of claim 1, wherein the heavy chain V-segment of the heavy chain variable region shares at least 90% sequence identity to SEQ ID NO:16, and wherein the Tight chain V-segment of the light chain variable region shares at least 90% sequence identity to SEQ ID NO:24.

3. The antibody of claim 1, wherein the heavy chain V-segment of the heavy chain variable region shares at least 90% sequence identity to an amino acid selected from the group consisting of SEQ ID NO:12, SEQ ID NO:13, SEQ ID NO:14 and SEQ ID NO:15, and wherein the light chain V-segment of the light chain variable region shares at least 90% sequence identity to an amino acid selected from the group consisting of SEQ ID NO:17, SEQ ID NO:18, SEQ ID NO:19, SEQ ID NO:20, SEQ ID NO:21, SEQ ID NO:22 and SEQ ID NO:23.

4. The antibody of claim 1, wherein the heavy chain FR4 of the heavy chain variable region is a human germline FR4.

5. The antibody of claim 4, wherein the heavy chain FR4 is SEQ ID NO:50.

6. The antibody of claim 4, wherein the heavy chain J-segment of the heavy chain variable region comprises the human germline JH4 partial sequence WGQGTLVTVSS (SEQ ID NO:50).

7. The antibody of claim 1, wherein the light chain FR4 of the light chain variable region is a human germline FR4.

8. The antibody of claim 7, wherein the light chain FR4 is SEQ ID NO:61.

9. The antibody of claim 7, wherein the light chain J-segment of the light chain variable region comprises the human germline Jk2 partial sequence FGQGKLEIK (SEQ ID NO:61).

10. The antibody of claim 1, wherein
   i) the CDR1 comprises SEQ ID NO:25;
   ii) the CDR2 comprises SEQ ID NO:28;
   iii) the heavy chain CDR3 comprises SEQ ID NO:32;
   iv) the CDR1 comprises SEQ ID NO:35;
   v) the CDR2 comprises SEQ ID NO:39; and
   vi) the light chain CDR3 comprises SEQ ID NO:41.

11. The antibody of claim 1, wherein
   i) the CDR1 comprises SEQ ID NO:25;
   ii) the CDR2 comprises SEQ ID NO:28;
   iii) the heavy chain CDR3 comprises SEQ ID NO:32;
   iv) the CDR1 comprises SEQ ID NO:36;
   v) the CDR2 comprises SEQ ID NO:39; and
   vi) the light chain CDR3 comprises SEQ ID NO:40.

12. The antibody of claim 1, wherein
   i) the CDR1 comprises SEQ ID NO:25;
   ii) the CDR2 comprises SEQ ID NO:28;
   iii) the heavy chain CDR3 comprises SEQ ID NO:32;
   iv) the CDR1 comprises SEQ ID NO:37;
   v) the CDR2 comprises SEQ ID NO:39; and
   vi) the light chain CDR3 comprises SEQ ID NO:40.

13. The antibody of claim 1, wherein
   i) the CDR1 comprises SEQ ID NO:25;
   ii) the CDR2 comprises SEQ ID NO:29;
   iii) the heavy chain CDR3 comprises SEQ ID NO:32;
   iv) the CDR1 comprises SEQ ID NO:35;

v) the CDR2 comprises SEQ ID NO:39; and
vi) the light chain CDR3 comprises SEQ ID NO:41.

14. The antibody of claim 1, wherein the heavy chain variable region shares at least 90% amino acid sequence identity to the variable region of SEQ ID NO:4 and the light chain variable region shares at least 90% amino acid sequence identity to the variable region of SEQ ID NO:11.

15. The antibody of claim 1, wherein the heavy chain variable region shares at least 90% amino acid sequence identity to the variable region selected from the group consisting of SEQ ID NO:1, SEQ ID NO:2 and SEQ ID NO:3 and the light chain variable region shares at least 90% amino acid sequence identity to the variable region selected from the group consisting of SEQ ID NO:5, SEQ ID NO:6, SEQ ID NO:7, SEQ ID NO:8, SEQ ID NO:9 and SEQ ID NO:10.

16. The antibody of claim 1, wherein the heavy chain variable region shares at least 95% amino acid sequence identity to the variable region selected from the group consisting of SEQ ID NO:1, SEQ ID NO:2 and SEQ ID NO:3 and the light chain variable region shares at least 95% amino acid sequence identity to the variable region selected from the group consisting of SEQ ID NO:5, SEQ ID NO:6, SEQ ID NO:7, SEQ ID NO:8, SEQ ID NO:9 and SEQ ID NO:10.

17. The antibody of claim 1, wherein the heavy chain variable region comprises an amino acid sequence selected from the group consisting of SEQ ID NO:1, SEQ ID NO:2 and SEQ ID NO:3 and the light chain variable region comprises an amino acid sequence selected from the group consisting of SEQ ID NO:5, SEQ ID NO:6, SEQ ID NO:7, SEQ ID NO:8, SEQ ID NO:9 and SEQ ID NO:10.

18. The antibody of claim 1, wherein the antibody is a FAb' fragment.

19. The antibody of claim 1, wherein the antibody is an IgG.

20. The antibody of claim 1, wherein the antibody is a single chain antibody (scFv).

21. The antibody of claim 1, wherein the antibody comprises human constant regions.

22. The antibody of claim 1, wherein the antibody does not bind to Tyrosine Kinase Receptor A or Tyrosine Kinase Receptor C.

23. The antibody of claim 1, wherein the antibody binds to the Ligand Binding Domain (LBD) of TrkB.

24. The antibody of claim 1, wherein the antibody competes with the binding of Brain Derived Neurotrophic Factor (BDNF) to TrkB.

25. The antibody of claim 1, wherein the antibody comprises a heavy chain comprising SEQ ID NO:1 and a light chain comprising SEQ ID NO:8.

26. The antibody of claim 1, wherein the antibody comprises a heavy chain comprising SEQ ID NO:1 and a light chain comprising SEQ ID NO:9.

27. The antibody of claim 1, wherein the antibody comprises a heavy chain comprising SEQ ID NO:1 and a light chain comprising SEQ ID NO:10.

28. The antibody of claim 1, wherein the antibody comprises a heavy chain comprising SEQ ID NO:3 and a light chain comprising SEQ ID NO:8.

29. A pharmaceutically acceptable composition comprising an antibody of claim 1 and a physiologically compatible excipient.

30. The composition of claim 29, wherein the pharmaceutical composition further comprises an agent that reduces blood glucose levels in an individual.

31. The composition of claim 29, wherein the pharmaceutical composition further comprises an agent that reduces body weight in an individual.

* * * * *